US008859780B2

(12) United States Patent
Ehring et al.

(10) Patent No.: US 8,859,780 B2
(45) Date of Patent: Oct. 14, 2014

(54) BENZIMIDAZOLE DERIVATIVES AS SELECTIVE BLOCKERS OF PERSISTENT SODIUM CURRENT

(71) Applicant: Allergan, Inc., Irvine, CA (US)

(72) Inventors: George R. Ehring, Huntington Beach, CA (US); Ellen Chao, Irvine, CA (US); Herman Ng, Tustin, CA (US); Hau Ton, Buena Park, CA (US); Jia Chian Li, Irvine, CA (US); Joseph S. Adorante, Irvine, CA (US); Michael S. Garst, Newport Beach, CA (US); Howard B. Rind, Laguna Niguel, CA (US); Mark R. Hansen, San Diego, CA (US); Alfred Arthur Avey, Jr., Eugene, CA (US); Lloyd Jay Dolby, Eugene, OR (US); Shervin Esfandiari, Eugene, OR (US); Vivian R. MacKenzie, Eugene, OR (US); Jeremiah Andrew Marsden, Eugene, OR (US); David Charles Muchmore, Eugene, OR (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/727,860

(22) Filed: Dec. 27, 2012

(65) Prior Publication Data

US 2013/0172389 A1 Jul. 4, 2013

Related U.S. Application Data

(60) Provisional application No. 61/580,978, filed on Dec. 28, 2011.

(51) Int. Cl.
| | | |
|---|---|---|
| *A61K 31/4439* | (2006.01) | |
| *A61K 31/4184* | (2006.01) | |
| *C07D 401/12* | (2006.01) | |
| *C07D 403/06* | (2006.01) | |
| *C07D 403/12* | (2006.01) | |
| *C07D 235/12* | (2006.01) | |
| *C07D 235/14* | (2006.01) | |
| *C07D 235/06* | (2006.01) | |
| *C07D 235/08* | (2006.01) | |
| *C07D 235/20* | (2006.01) | |

(52) U.S. Cl.
CPC ............ *C07D 235/12* (2013.01); *C07D 235/06* (2013.01); *C07D 401/12* (2013.01); *C07D 235/08* (2013.01); *C07D 403/12* (2013.01); *C07D 235/20* (2013.01); *C07D 235/14* (2013.01); *C07D 403/06* (2013.01)
USPC .................. 548/310.1; 548/304.4; 548/305.4; 548/306.1; 548/309.7; 514/338; 514/394

(58) Field of Classification Search
USPC ........... 548/305.4, 306.1, 310.1, 309.7, 304.4
See application file for complete search history.

(56) References Cited

U.S. PATENT DOCUMENTS

| | | | |
|---|---|---|---|
| 3,256,288 A * | 6/1966 | Moyle et al. ................... | 546/199 |
| 3,536,809 A | 10/1970 | Applezweig | |
| 3,598,123 A | 8/1971 | Zaffaroni | |
| 3,630,200 A | 12/1971 | Higuchi | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,366,738 A | 11/1994 | Rork et al. | |
| 6,255,494 B1 * | 7/2001 | Britton et al. ............. | 548/310.1 |
| 6,991,910 B2 | 1/2006 | Adorante et al. | |
| 7,060,723 B2 | 6/2006 | Ehring et al. | |
| 7,125,908 B2 | 10/2006 | Ehring et al. | |
| 7,309,716 B2 | 12/2007 | Wilson et al. | |
| 7,361,478 B2 | 4/2008 | Adorante et al. | |
| 7,754,440 B2 | 7/2010 | Adorante | |
| 7,763,651 B2 | 7/2010 | Ehring | |
| 7,767,718 B2 | 8/2010 | Ehring | |
| 8,153,645 B2 | 4/2012 | Ehring et al. | |
| 2003/0119754 A1 * | 6/2003 | Lackey et al. ................... | 514/23 |
| 2010/0048564 A1 * | 2/2010 | Shimada et al. ............ | 514/234.5 |

FOREIGN PATENT DOCUMENTS

| | | |
|---|---|---|
| DE | 1079059 | 4/1960 |
| EP | 0252507 | 1/1988 |
| EP | 745600 A1 * | 12/1996 |
| WO | 01-38564 | 5/2001 |
| WO | WO-03/024937 A1 * | 3/2003 |
| WO | 2006-122546 | 11/2006 |
| WO | 2007-115077 | 10/2007 |

OTHER PUBLICATIONS

Chemical Abstracts Registry No. 663946-91-6, entered into the Registry file on STN CAS Online Mar. 17, 2004.*

(Continued)

*Primary Examiner* — Laura L. Stockton
(74) *Attorney, Agent, or Firm* — Krishna Banerjee

(57) ABSTRACT

The present invention is directed to a compound of Formula I

Formula I

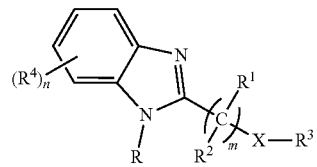

or a pharmaceutically acceptable salt thereof; wherein R, $R^1$, $R^2$, $R^3$, $R^4$, m, and n are as defined herein, to pharmaceutical compositions comprising said compound, and to methods of treating diseases or conditions mediated by elevated persistent sodium current, such as an ocular disorder, multiple sclerosis, seizure disorder, and chronic pain.

10 Claims, 11 Drawing Sheets

(56) References Cited

OTHER PUBLICATIONS

Reddy et al., Asian Journal of Research in Chemistry, (2009), 2(2), pp. 162-167.*

Chemical Abstracts Registry No. 1182754-53-5, entered into the Registry file on STN CAS Online Sep. 11, 2009.*

Anderson et al, The Practice of Medicinal Chemistry, 1996, 32 Pages, 3rd Edition, Contributor pages and Index pages only.

Berge, Stephen M., Pharmaceutical Salts, Journal of Pharmaceutical Sciences, Jan. 1977, 1-19, 66 (1).

Bingham, Ann et al, Over One Hundred Solvates of Sulfathiazole, Chem. Commun., 2001, 603-604.

Caira, Mino et al, Preparation and Crystal Characterization of a Polymorph, a Monohydrate, and an Ethyl Acetate Solvate of the Antifungal Fluconazole, Journal of Pharmaceutical Sciences, Mar. 2004, 601-611, 93(3).

Catterall, William, A 3D View of Sodium Channels, Nature, Feb. 2001, 988-991, 409.

Chaudhari, Raju et al, Synthesis and Antimicrobial Activities of Novel 8-(1-alkyl/alkylsulphonyl/alkoxycarbonyl-benzimidazol-2-ylmethoxy)-5-Chloroquinolines, J. Serb. Chem. Soc., 2011, 1199-1206, 76(9).

Dubey, P.K. et al, A Facile Solvent-Free Synthesis of 1-Alkyl/Aralkyl-2-(1-arylsulfonyl alkyl) Benzimidazoles Using "TBAB" as Surface Catalyst, Journal of Heterocyclic Chemistry, Nov. 2010, 1317-1322, 47(6).

Edward B. Roche, Bioreversible Carriers in Drug Design, Theory and Application, 1987, Chapter 4, p. 121-163., American Pharmaceutical Association and Pergamon Press.

Ehring, George et al, Diversity of Expression of Voltage-Gated Sodium Channels in the Rat Retina, ARVO Meeting Abstracts 53, May 9, 2012, 2 Pages, 478.

Goldin, Alan et al, Nomenclature of Voltage-Gated Sodium Channels, Neuron, Nov. 2000, 365-368, 28.

Gould, Philip, Salt Selection for Basic Drugs, International Journal of Pharmaceutics, 1986, 201-217, 33.

Greene, Theodora, Protective Groups in Organic Synthesis, 1991, 52 Pages, 3rd Edition, Content pages only.

Hamill, O.P. et al, Improved Patch-Clamp Techniques for High-Resolution Current Recording From Cells and Cell-Free Membrane Patches, Pflugers Arch, 1981, 85-100, 391.

Higuchi, T. et al, Pro-Drugs as Novel Drug Delivery Systems, 1975, 6 Pages, Title pages only.

Kamiya, Kazusaku et al, A Nonsense Mutation of the Sodium Channel Gene SCN2A in a Patient with Intractable Epilepsy and Mental Decline, The Journal of Neuroscience, Mar. 17, 2004, 2690-2698, 24(11).

O'Brien, Brendan et al, Tetrodotoxin-Resistant Voltage-Gated Sodium Channels Nav1.8 and Nav1.9 Are Expressed in the Retina, The Journal of Comparative Neurology, 2008, 940-951, 508.

Pereira, S. et al, Severe Epilepsy, Retardation, and Dysmorphic Features with a 2q Deletion Including SCN1A and SCN2A, Neurology, 2004, 191-192, 63.

Raymond, Christopher et al, Expression of Alternatively Spliced Sodium CHannel a-Subunit Genes, The Journal of Biological Chemistry, 2004, 46234-46241, 279(44).

Remington's, Emulsifying and Suspending Agents, Remington's Pharmaceutical Sciences, 1990, 1304-1308, 18 Edition.

Rhodes, Thomas et al, Noninactivating Voltage-Gated Sodium Channels in Severe Myoclonic Epilepsy of Infancy, Proc. Natl. Acad. Sci., 2004, 11147-11152, 101(30).

Sato, Chikara et al, The Voltage-Sensitive Sodium Channel is a Bell-Shaped Molecule With Several Cavities, Nature, Feb. 2001, 1047-1051, 409.

Srinivas, K. et al, Zinc-Mediated Tandem-One-Pot Facile Synthesis of 1-(arylsulfonyl) Aryl/Heteryl Methanes: A Case of C—S Bond Formation, Synthetic Communications, 2011, 1584-1592, 41.

Stahl, Heinrich et al, Handbook of Pharmaceutical Salts: Properties, Selection, and Use, 2002, 324-325, International Union of Pure and Applied Chemistry.

Van Tonder, Elsa et al, Preparation and Physicochemical Characterization of 5 Niclosamide Solvates and 1 Hemisolvate, AAPS PharmSciTech, 2004, 1-10, 5(1).

Yu, Frank et al, Sodium Channel B4, a New Disulfide-Linked Auxiliary Subunit with Simularity to B2, The Journal of Neuroscience, Aug. 2003, 7577-7585, 23(20).

Yu, Frank et al, The VGL-Chanome: A Protein Superfamily Specialized for Electrical Signaling and Ionic Homeostasis, Sci. STKE, 2004, 1-17.

Patent Cooperation Treaty, Notification of Transmittal of the International Search Report and the Written Opinion of the International Searching Authority, or the Declaration, Form PCT/ISA/220, Int. App. No. PCT/US2012/071784, Jul. 3, 2013.

* cited by examiner

BENZIMIDAZOLE DERIVATIVES AS SELECTIVE BLOCKERS OF PERSISTENT SODIUM CURRENT

CROSS REFERENCE TO RELATED APPLICATIONS

This application claims the benefit of U.S. Provisional Application Ser. No. 61/580,978 filed Dec. 28, 2011, which is incorporated by reference herein in its entirety.

FIELD OF THE INVENTION

The present invention is directed to benzimidazole derivative compounds, pharmaceutical compositions comprising the compounds and methods of using the compounds and the pharmaceutical compositions that selectively reduce persistent sodium current in a mammal and in treating diseases or conditions that involve elevated persistent sodium current in a mammal, such as chronic pain, epileptic seizure, and ocular/retinal diseases, as well as other diseases and conditions associated with elevated persistent sodium current.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., *Nature* (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., *Neuron* (2000), Vol. 28, pp. 365-368). Each alpha-subunit contains four homologous domains, I to IV, each with six predicted transmembrane segments. The alpha-subunit of the sodium channel, forming the ion-conducting pore and containing the voltage sensors regulating sodium ion conduction has a relative molecular mass of 260,000. Electrophysiological recording, biochemical purification, and molecular cloning have identified nine different sodium channel alpha subunits and four beta subunits (Yu, F. H., et al., *Sci. STKE* (2004), 253; and Yu, F. H., et al., *Neurosci.* (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., *Nature* (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favored by membrane hyperpolarization, before they can reopen. Different sodium channel subtypes vary in the voltage range over which they activate and inactivate as well as their activation and inactivation kinetics. Alterations in the gating mechanism of sodium channels can contribute to disease. A loss of the ability to inactivate results in a sustained influx of sodium into cells. This process is termed a persistent sodium current. Depending on the amplitude of this current changes in cell excitability or triggered cell death can occur.

The sodium channel family of proteins has been extensively studied and shown to be involved in a number of vital body functions. Research in this area has identified variants of the alpha subunits that result in major changes in channel function and activities, which can ultimately lead to major pathophysiological conditions. Implicit with function, this family of proteins is considered a prime point of therapeutic intervention. $Na_v1.1$ and $Na_v1.2$ are highly expressed in the brain (Raymond, C. K., et al., *J. Biol. Chem.* (2004), 279 (44):46234-41) and retina, and are vital to normal brain function. In humans, mutations in $Na_v1.1$ and $Na_v1.2$ result in severe epileptic states and in some cases mental decline (Rhodes, T. H., et al., *Proc. Natl. Acad. Sci. USA* (2004), 101(30):11147-52; Kamiya, K., et al., *J. Biol. Chem.* (2004), 24(11):2690-8; Pereira, S., et al., *Neurology* (2004), 63(1): 191-2). As such both channels have been considered as validated targets for the treatment of epilepsy (see PCT Published Patent Publication No. WO 01/38564).

Voltage-gated sodium channels comprise a family of proteins designated from $Na_v1.3$ through $Na_v1.9$. The sodium channel isoforms show differential expression throughout the central and peripheral nervous system. (Catterall, W. A., *Nature* (2001), Vol. 409, pp. 988-990; Goldin et al., *Neuron* (2000), Vol. 28, pp. 365-368; Ehring, George R., et al. "Diversity of Expression of Voltage-Gated Sodium Channels in the Rat Retina." *ARVO Meeting Abstracts* 53.6 (2012): 5337; O'Brien, B. J., et al. "Tetrodotoxin-resistant voltage-gated sodium channels Na(v)1.8 and Na(v)1.9 are expressed in the retina." *J Comp Neurol* 508.6 (2008): 940-51).

U.S. Pat. No. 7,309,716 (assigned to Vertex Pharmaceuticals) discloses benzimidazole compounds that are useful as inhibitors of voltage-gated sodium channels.

U.S. Pat. Nos. 7,125,908, 7,763,651, 7,767,718, and 8,153,645 (all assigned to Allergan) disclose methods of treating chronic pain in a mammal by administering to the mammal an effective amount of a selective persistent sodium channel antagonist that has at least 20-fold selectivity for persistent sodium current relative to transient sodium current.

U.S. Pat. No. 7,754,440 (assigned to Allergan) discloses a method for identifying a selective persistent $Na^+$ channel blocker by measuring the ability of the blocker to reduce or inhibit a persistent $Na^+$ current to a greater degree than a transient $Na^+$ current. Aspects of the present method provide $Na^+$ depletion/repletion methods for identifying a selective blocker of a persistent $Na^+$ channel, hyperpolarization methods for identifying a blocker of a persistent $Na^+$ channel, and Na/K ATPase pump inhibitor methods for identifying a selective blocker of a persistent $Na^+$ channel.

SUMMARY OF THE INVENTION

The present invention is directed to a compound of Formula I

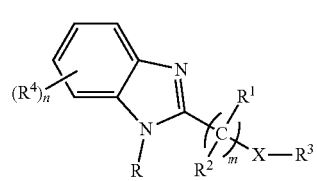

Formula I or a pharmaceutically acceptable salt thereof; wherein:
R is selected from the group consisting of $C_{1-6}$ alkyl which is unsubstituted or substituted with a substituent selected from the group consisting of —$N(C_{1-6}$ alkyl$)_2$, $C_{6-12}$ aryl, $C_{6-12}$ aryloxy and heteroaryl;
each $R^1$ and $R^2$ are independently H or $C_{1-6}$ alkyl;
$R^3$ is selected from the group consisting of $C_{6-12}$ aryl and heteroaryl;

each R⁴ independently is selected from the group consisting of $C_{1-6}$ alkyl, and $C_{1-6}$ alkoxy, wherein said $C_{1-6}$ alkyl and the alkyl portion of said $C_{1-6}$ alkoxy are independently unsubstituted or substituted with a substituent selected from the group consisting of hydroxyl, —C(=O)OH, —C(=O)O-$C_{1-6}$ alkyl, —C(=O)-heterocyclyl, and —N($C_{1-6}$ alkyl)₂;

R⁵ is H or $C_{1-6}$ alkyl;

X is selected from the group consisting of a covalent bond, O, NR⁵, —S(=O)—, and —S(=O)₂—;

m is 1 or 2; and n is 0 or 1;

with the proviso that when R is an unsubstituted $C_{1-6}$ alkyl, then either (1) X is other than a covalent bond, or (2) R⁴ is $C_{1-6}$ alkoxy, wherein the alkyl portion of said $C_{1-6}$ alkoxy is substituted with a —N($C_{1-6}$ alkyl)₂ substituent.

The present invention is also directed to a pharmaceutical composition comprising at least one compound of Formula I as set forth above, or a pharmaceutically acceptable salt thereof and a pharmaceutically acceptable carrier.

The present invention is also directed to a method of blocking persistent sodium current without affecting transient current in a mammal using a therapeutically effective amount of the compound of Formula I

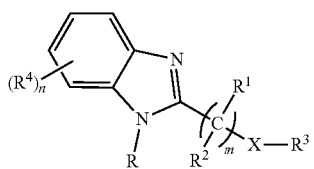

Formula I or a pharmaceutically acceptable salt thereof; wherein:

R is selected from the group consisting of $C_{1-6}$ alkyl which is unsubstituted or substituted with a substituent selected from the group consisting of —N($C_{1-6}$ alkyl)₂, $C_{2-6}$ alkenyl, $C_{6-12}$ aryl, $C_{6-12}$ aryloxy and heteroaryl;

each R¹ and R² are independently H or $C_{1-6}$ alkyl;

R³ is selected from the group consisting of $C_{6-12}$ aryl and heteroaryl;

each R⁴ independently is selected from the group consisting of $C_{1-6}$ alkyl, and $C_{1-6}$ alkoxy, wherein said $C_{1-6}$ alkyl and the alkyl portion of said $C_{1-6}$ alkoxy are independently unsubstituted or substituted with a substituent selected from the group consisting of hydroxyl, —C(=O)OH, —C(=O)O—$C_{1-6}$ alkyl, —C(=O)-heterocyclyl, and —N($C_{1-6}$ alkyl)₂;

R⁵ is H or $C_{1-6}$ alkyl;

X is selected from the group consisting of a covalent bond, O, S, NR⁵, —S(=O)—, and —S(=O)₂—;

m is 1 or 2; and n is 0 or 1.

The present invention is also directed to methods of using the compounds of Formula I and pharmaceutical compositions comprising the compounds of Formula I as set forth above for the treatment of diseases and conditions that are mediated by elevated persistent sodium current, such as pain (especially chronic pain) ocular and retinal disorders, seizure disorders and multiple sclerosis.

DETAILED DESCRIPTION OF THE INVENTION

Definitions

Figure 1:
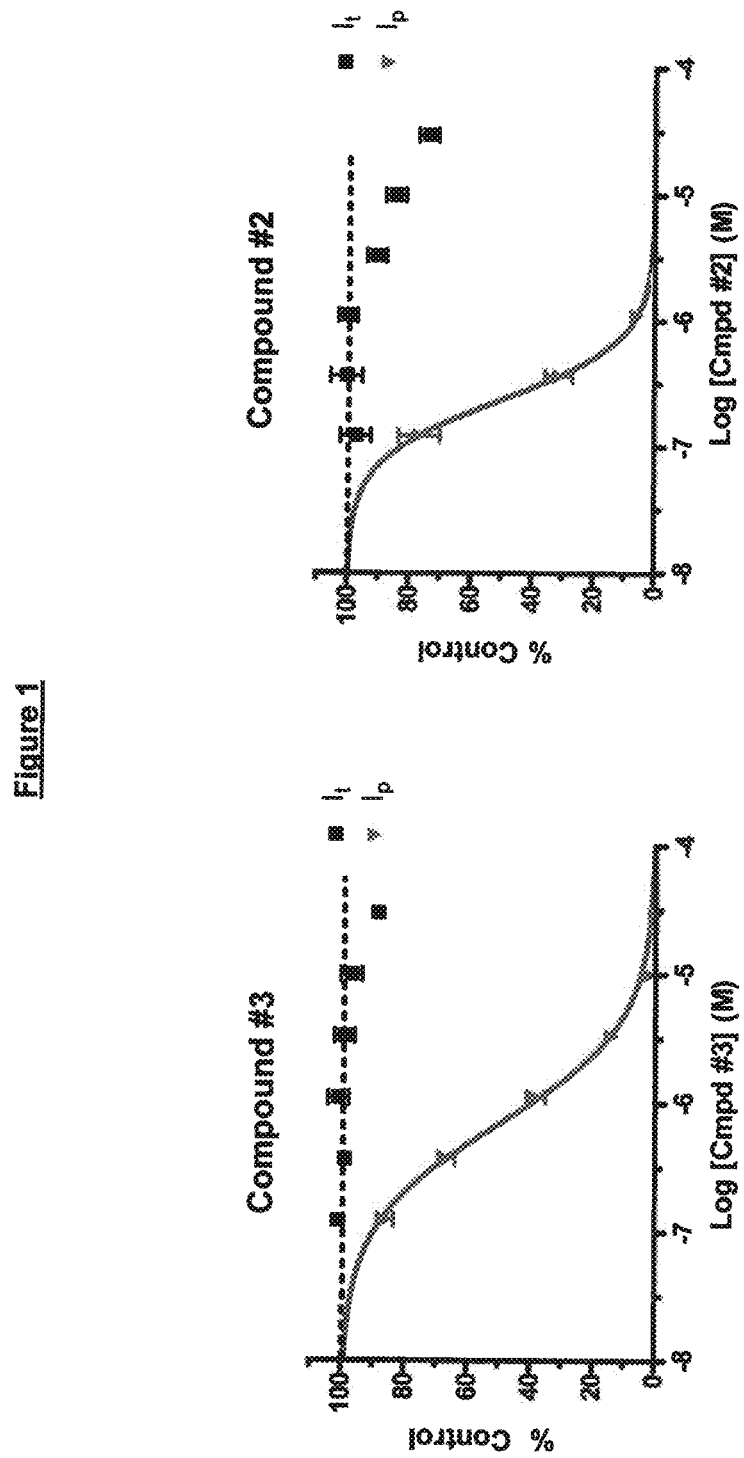
FIG. 1 shows show the in vitro electrophysiological data on $Na_v1.3$ for compound #s 2 and 3 with emphasis on the selectivity for the persistent ($I_p$) vs. transient ($I_t$) sodium currents.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, aryl, cycloalkyl, cyano, hydroxy, alkoxy, alkylthio, amino, oxime (e.g., =N—OH), —NH (alkyl), —NH(cycloalkyl), —N(alkyl)$_2$, —O—C(O)-alkyl, —O—C(O)-aryl, —O—C(O)-cycloalkyl, —SF$_5$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —SF$_5$, —OSF$_5$ (for aryl), —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), —NY$_1$Y$_2$, -alkyl-NY$_1$Y$_2$, —C(O)NY$_1$Y$_2$, —SO$_2$NY$_1$Y$_2$ and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

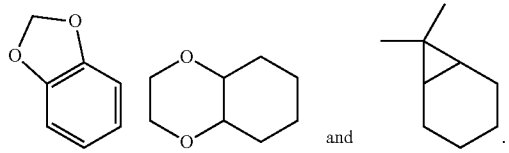

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. Example of such moiety is pyrrolidone:

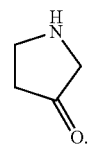

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. Example of such moiety is pyrrolidinone:

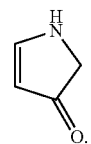

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

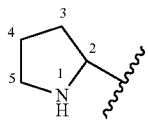

there is no —OH attached directly to carbons marked 2 and 5.

It should also be noted that tautomeric forms such as, for example, the moieties:

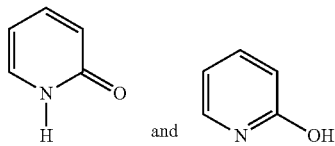 [SMILES: O=c1cccc[nH]1 ; Oc1ccccn1]

are considered equivalent in certain embodiments of this invention.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like) in sufficient purity to be characterizable by standard analytical techniques described herein or well known to the skilled artisan.

The present invention further includes the compound of formula I in all its isolated forms. Thus, for example, the compound of Formula I is intended to encompass all forms of the compound such as, for example, any solvates, hydrates, stereoisomers, tautomers etc.

The present invention further includes the compound of formula I in its purified form.

It should also be noted that any carbon as well as heteroatom with unsatisfied valences in the text, schemes, examples and Tables herein is assumed to have the sufficient number of hydrogen atom(s) to satisfy the valences. And any one or more of these hydrogen atoms can be deuterium.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93 (3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5 (1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula I, and of the salts, solvates, esters and prodrugs of the compounds of Formula I, are intended to be included in the present invention.

Embodiments of the Invention

In one embodiment of the present invention, in Formula I, as set forth in the Summary of the Invention, R is and unsubstituted straight chain or branched $C_{1-6}$ alkyl.

In another embodiment, in Formula I, R is $C_{1-6}$ alkyl which is substituted with a $C_{6-12}$ aryloxy group.

In another embodiment, in Formula I, R is $C_{1-6}$ alkyl which is substituted with a $C_{6-12}$ aryloxy group, wherein the "aryl" portion of said $C_{6-12}$ aryloxy group is unsubstituted or substituted with 1-2 $C_{1-6}$ alkyl or $C_{1-6}$ alkoxy substitutents.

In another embodiment, in Formula I, R is $C_{1-6}$ alkyl which is substituted with a heteroaryl substitutent, wherein said heteroaryl group is five- to six-membered ring containing 1-2 ring N atoms, and wherein when said five- to six-membered ring containing 1-2 ring N atoms has two substituents on adjacent carbon atoms, said substituents together with the carbon atoms to which they are attached can optionally form a phenyl ring, and wherein said six-membered ring containing 1-2 ring N atoms, optionally with said phenyl ring is optionally further substituted with a ring system substituent.

In another embodiment, in Formula I, In another embodiment, in formula I, R is $C_{1-6}$ alkyl which is substituted with a heteroaryl substitutent, wherein said heteroaryl group is five- to six-membered ring containing 1-2 ring N atoms, and wherein when said five- to six-membered ring containing 1-2 ring N atoms has two substituents on adjacent carbon atoms, said substituents together with the carbon atoms to which they are attached can optionally form a phenyl ring, and wherein said six-membered ring containing 1-2 ring N atoms, optionally with said phenyl ring is optionally further substituted with a ring system substituent, wherein said five- to six-membered ring containing 1-2 ring N atoms, optionally with said phenyl ring is selected from the group consisting of pyrzolyl, imidazolyl, pyrimidinyl, pyrazinyl, and benzimidazolyl.

In another embodiment, in Formula I, R is $C_{1-6}$ alkyl which is substituted with a heteroaryl substitutent, wherein said heteroaryl group is five- to six-membered ring containing 1-2 ring N atoms, and wherein when said five- to six-membered ring containing 1-2 ring N atoms has two substituents on adjacent carbon atoms, said substituents together with the carbon atoms to which they are attached can optionally form a phenyl ring, and wherein said six-membered ring containing 1-2 ring N atoms, optionally with said phenyl ring is optionally further substituted with a ring system substituent, wherein said five- to six-membered ring containing 1-2 ring N atoms, optionally with said phenyl ring is selected from the group consisting of imidazolyl, and benzimidazolyl.

In another embodiment, in Formula I, R is $C_{1-6}$ alkyl which is substituted with a —$N(C_{1-6}$ alkyl$)_2$ substituent.

In another embodiment, in Formula I, wherein R is selected from the group consisting of:

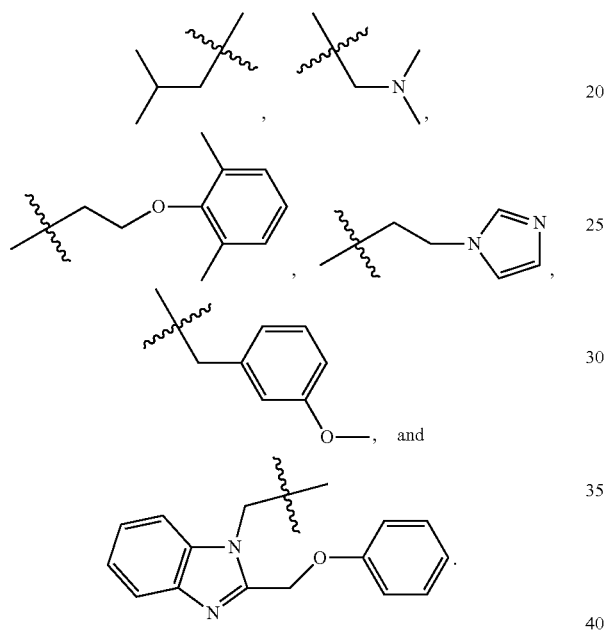

In another embodiment, in Formula I, $R^1$ and $R^2$ are both H.

In another embodiment, in Formula I, $R^1$ and $R^2$ are both H, and m is 1 or 2.

In another embodiment, in Formula I, $R^1$ and $R^2$ are both H, m is 1, and X is O.

In another embodiment, in Formula I, $R^1$ and $R^2$ are both H, m is 2, and X is a covalent bond.

In another embodiment, in Formula I, $R^1$ and $R^2$ are both H, m is 1, and X is —S(=O)—.

In another embodiment, in Formula I, $R^1$ and $R^2$ are both H, m is 1, and X is $NR^5$, wherein $R^5$ is H.

In another embodiment, in Formula I, $R^3$ is $C_{6-12}$ aryl, which is unsubstituted or substituted with 1-2 substituents selected from the group consisting of: $C_{1-6}$ alkoxy, halo, and haloalkyl.

In another embodiment, in Formula I, $R^3$ is $C_{6-12}$ aryl, which is unsubstituted or substituted with 1-2 substituents selected from the group consisting of: $C_{1-6}$ alkoxy, halo, and haloalkyl; wherein:

the $C_{1-6}$ alkoxy substituent is selected from the group consisting of methoxy, ethoxy, isobutoxy;

the halo substituent is selected from the group consisting of: fluoro and chloro; and the haloalkyl group is trifluoromethyl.

In another embodiment, in Formula I, $R^4$ is an unsubstituted or substituted $C_{1-6}$ alkoxy, which is selected from the group consisting of: ethoxy, —$OCH_2CH_2CH(CH_3)CH_3$, —O—$CH_2CH_2CH_3$, —O—$CH_2CH_2$—$N(CH_2CH_3)_2$, —O—$CH_2CH_2$-pyrazolyl, —O—$CH_2$—C(=O)-pyrrolidinyl, —O—$CH_2$—C(=O)—O—$CH_2CH_3$, and —O—$CH_2$—C(=O)—OH.

In another embodiment, in Formula I, $R^4$ is an unsubstituted or substituted $C_{1-6}$ alkyl which is propyl.

In another embodiment, the compound of Formula I is selected from the group consisting of:

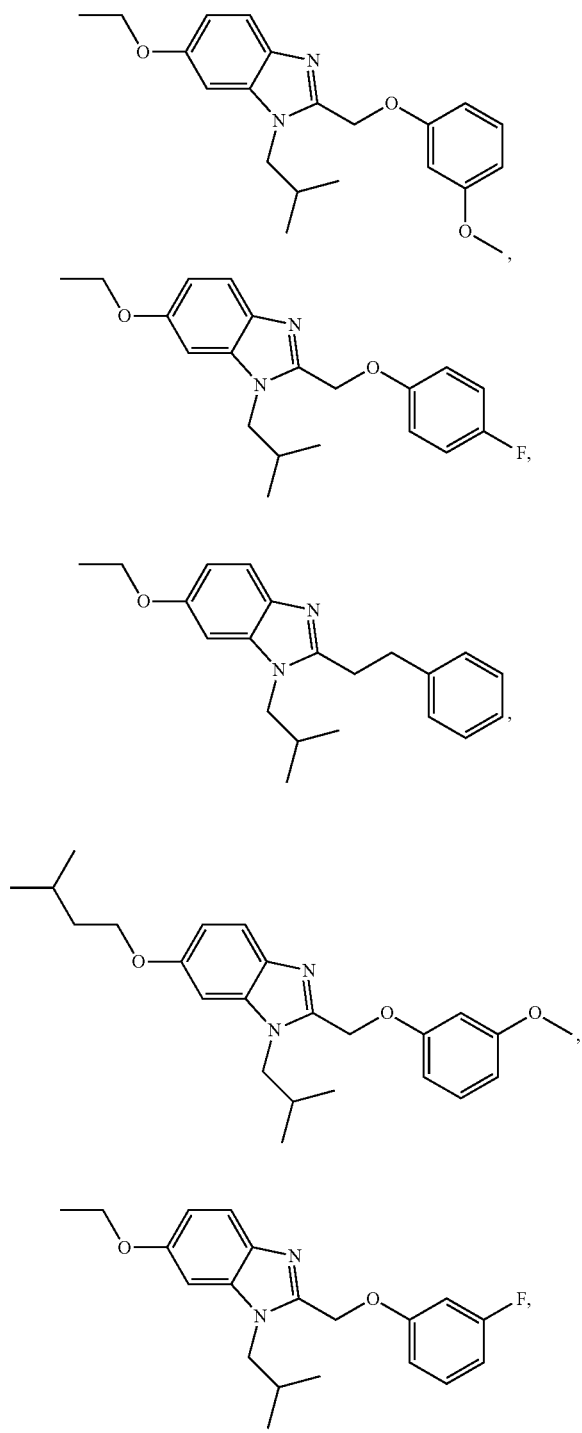

17
-continued
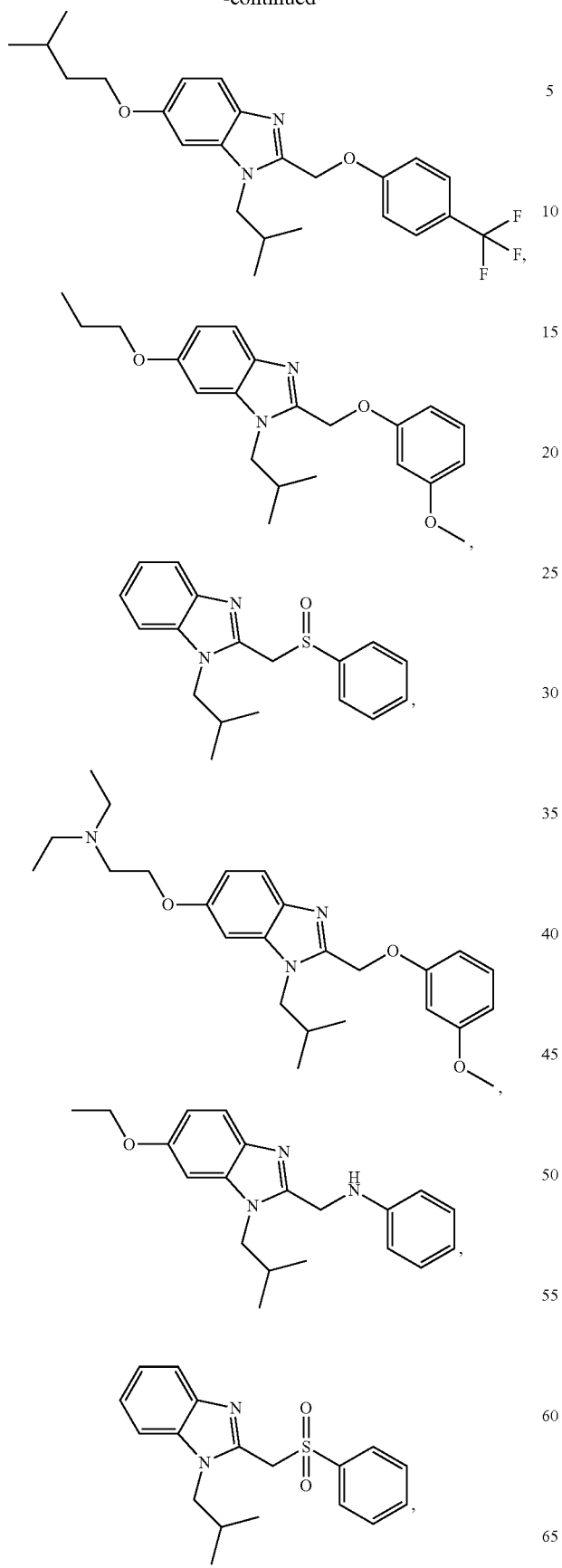
18
-continued
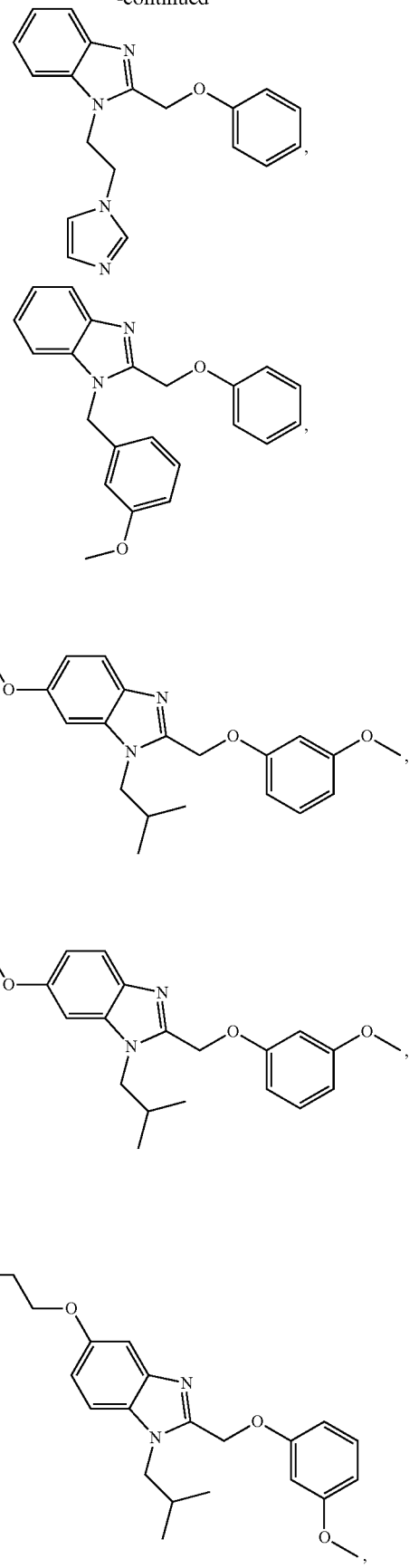

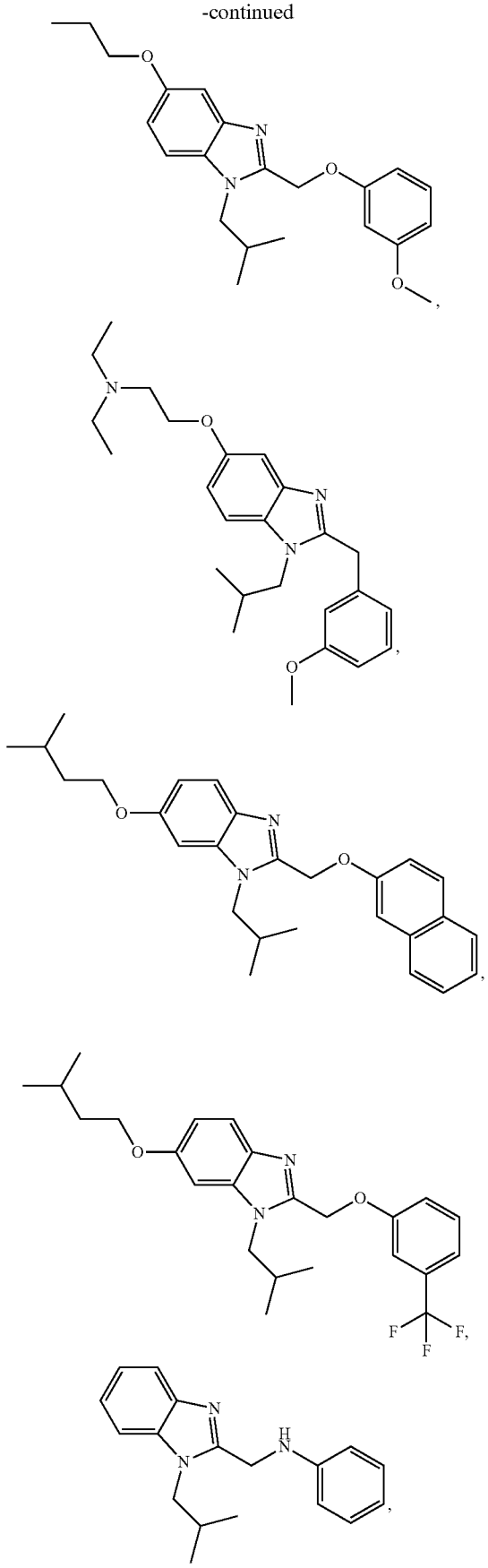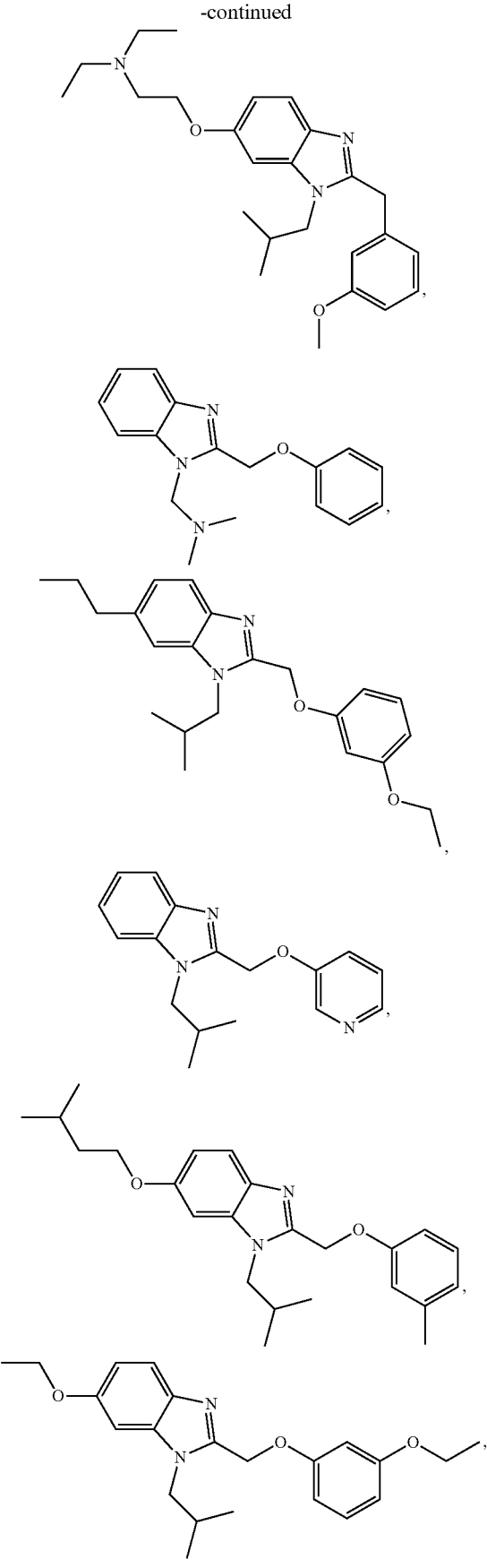

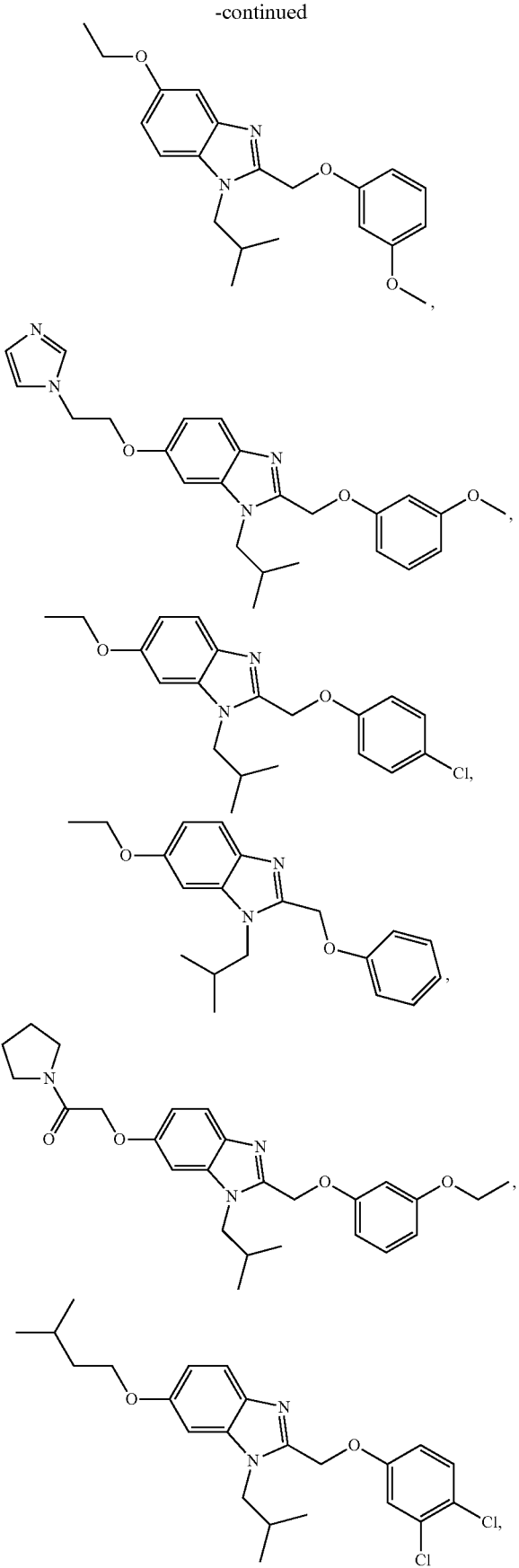
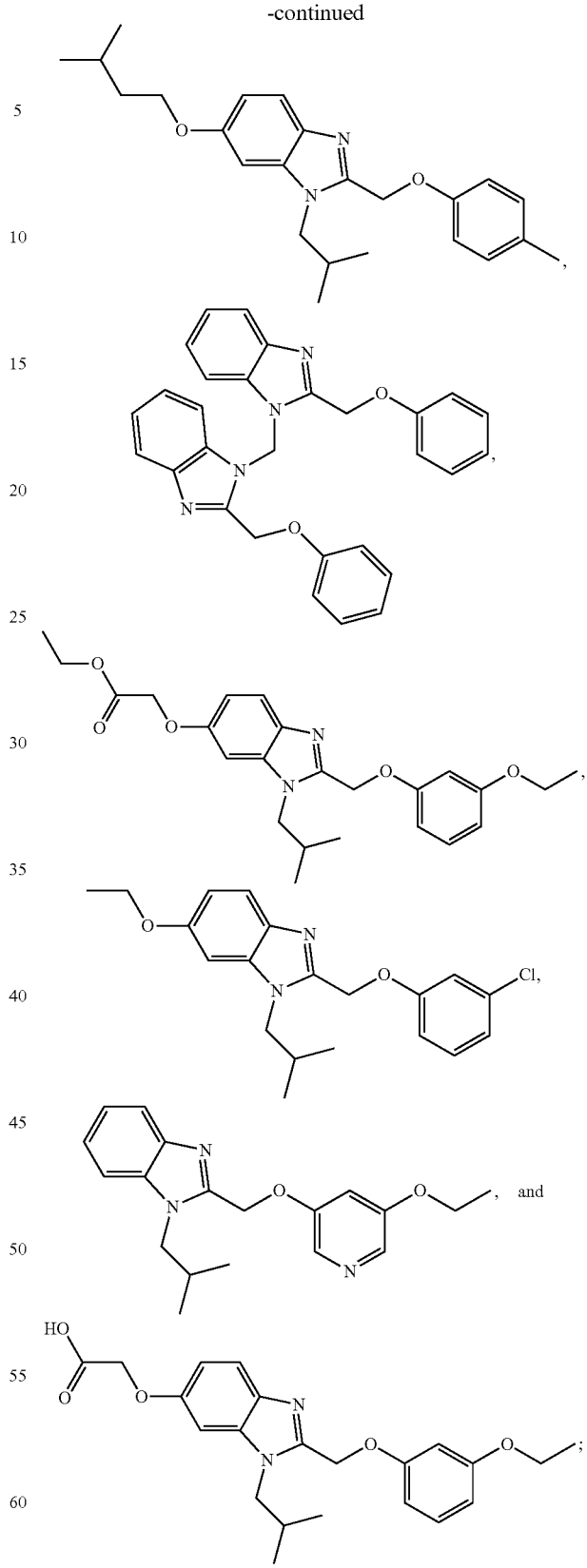
or a pharmaceutically acceptable salt thereof.
In another embodiment, the disease or condition that is mediated by elevated persistent sodium current is selected from the group consisting of pain (such as chronic pain), ocular disorder, multiple sclerosis, and seizure disorder.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g. musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

In another embodiment, the ocular disorder is selected from the group consisting of age related macular degeneration (AMD) (including wet and dry AMD), geographic atrophy, retinitis pigmentosa, Stargardt's disease cone dystrophy, and pattern dystrophy of the retinal pigmented epithelium, macular edema, retinal detachment, retinal trauma, retinal tumors and retinal diseases associated with said tumors, congenital hypertrophy of the retinal pigmented epithelium, acute posterior multifocal placoid pigment epitheliopathy, optic neuritis, acute retinal pigment epithelitis, optic neuropathies and glaucoma.

In another embodiment, the ocular disorder is selected from the group consisting of age related macular degeneration and geographic atrophy.

In another embodiment, the ocular disorder is optic neuritis.

In another embodiment, the disease or condition that is mediated by elevated persistent sodium current is chronic pain selected from the group consisting of neuropathic pain, inflammatory pain, visceral pain, post-operative pain, pain resulting from cancer or cancer treatment, headache pain, irritable bowel syndrome pain, fibromyalgia pain, and pain resulting from diabetic neuropathy.

In another embodiment, the disease or condition that is mediated by elevated persistent sodium current is multiple sclerosis.

In another embodiment, the disease or condition that is mediated by elevated persistent sodium current is a central nervous system disorder, such as seizure disorder selected from the group consisting of epilepsy and chemically-induced seizure disorder (e.g., neurotoxins that elevate persistent currents), anxiety, depression and bipolar diseases.

In another embodiment, the compound of Formula I useful in treatment methods of the present invention is selected from the group consisting of:

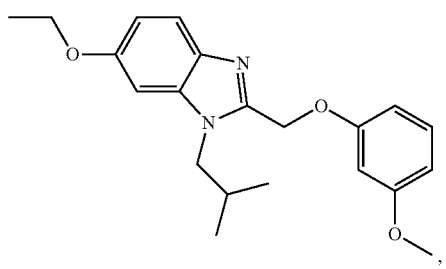

-continued

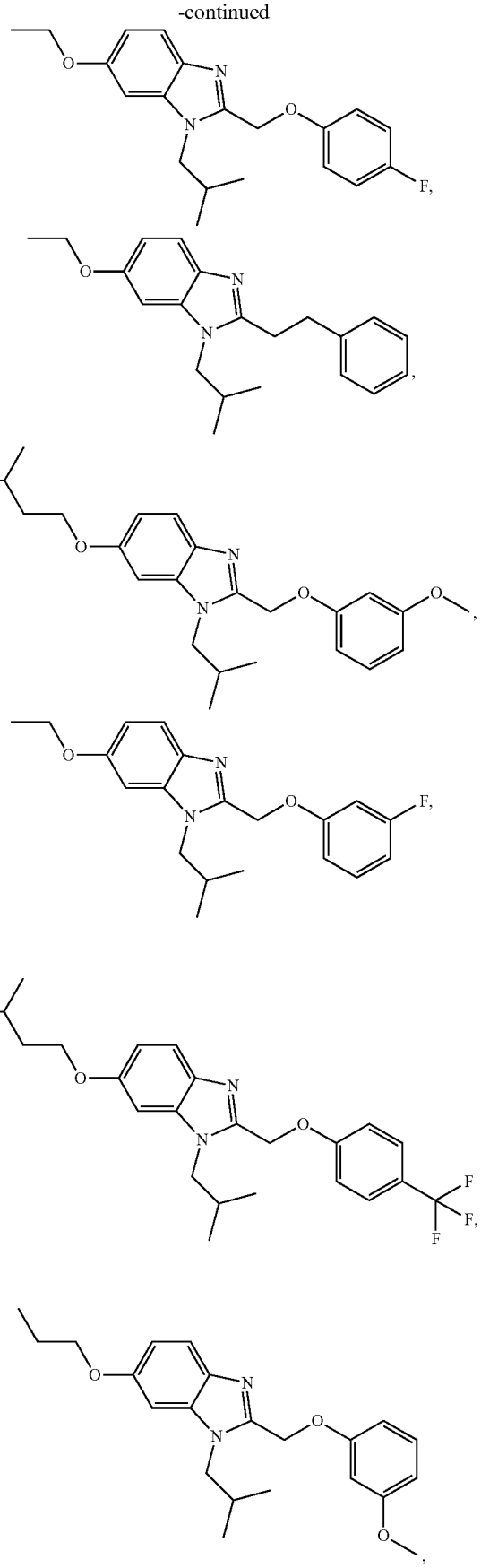

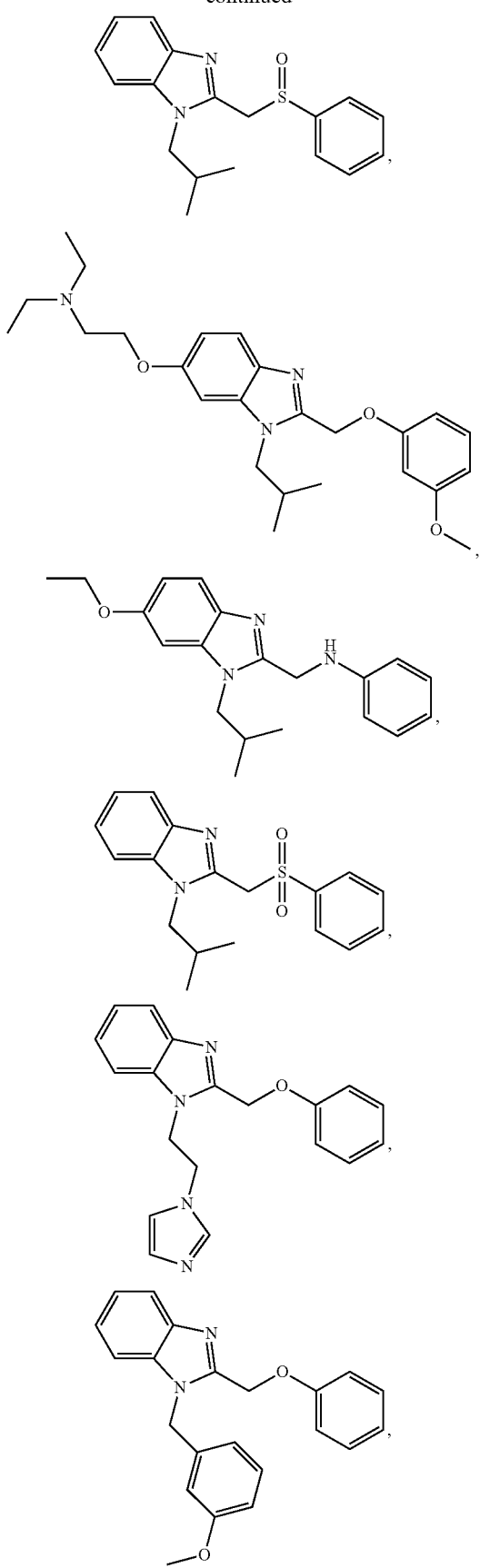

27
-continued
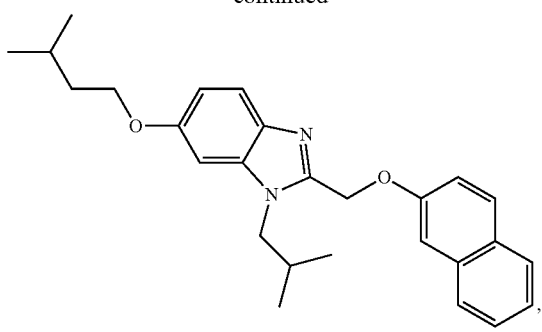
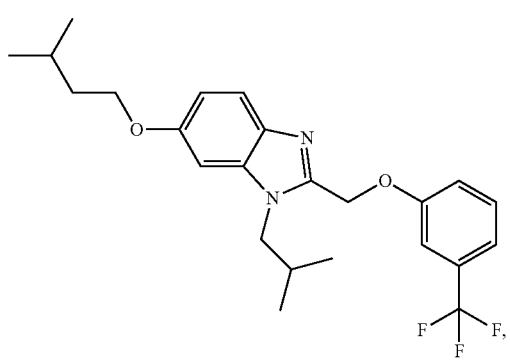
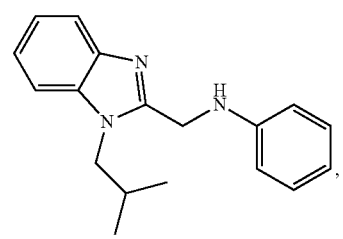
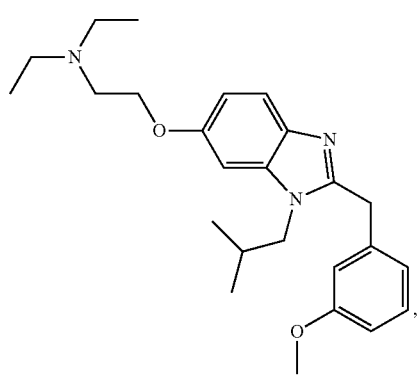
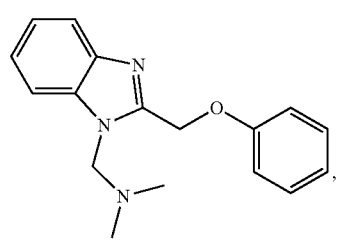
28
-continued
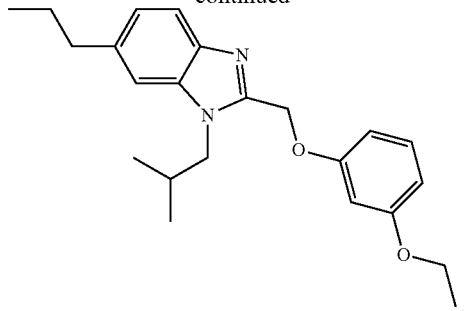
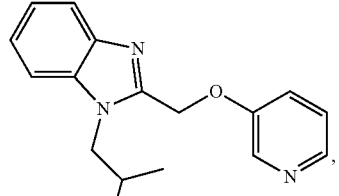
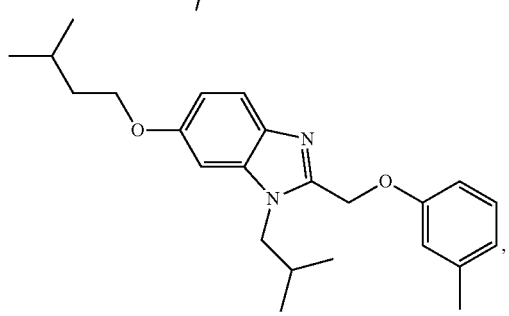
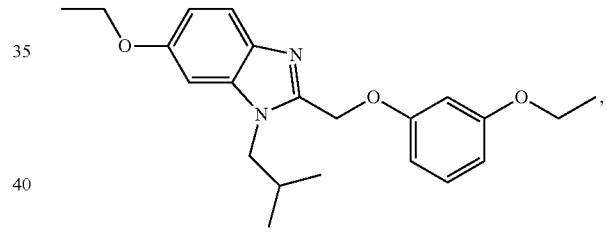
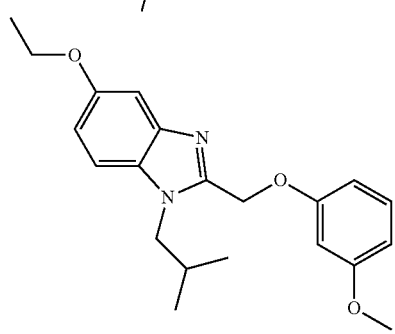
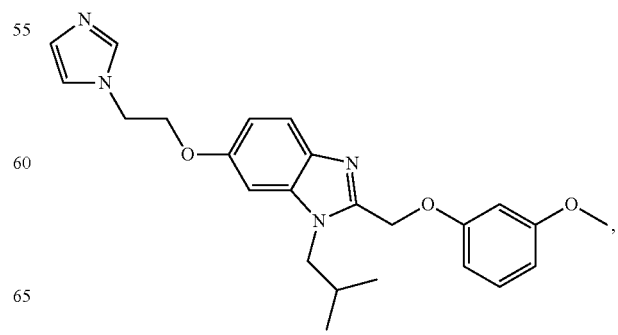

29
-continued
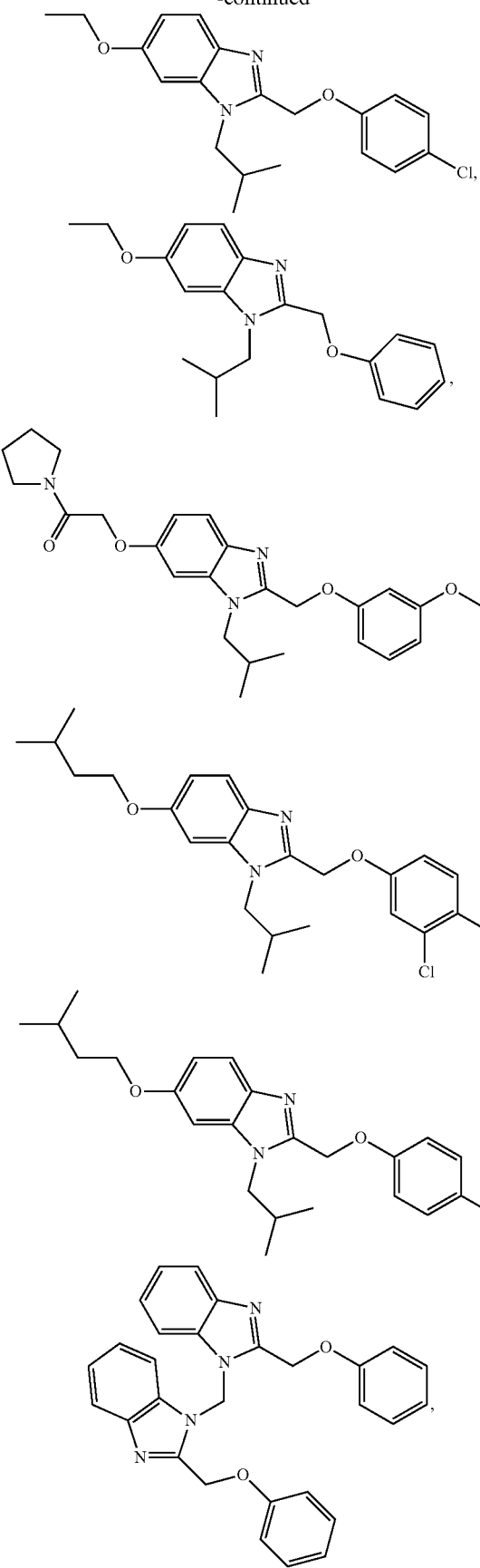
30
-continued
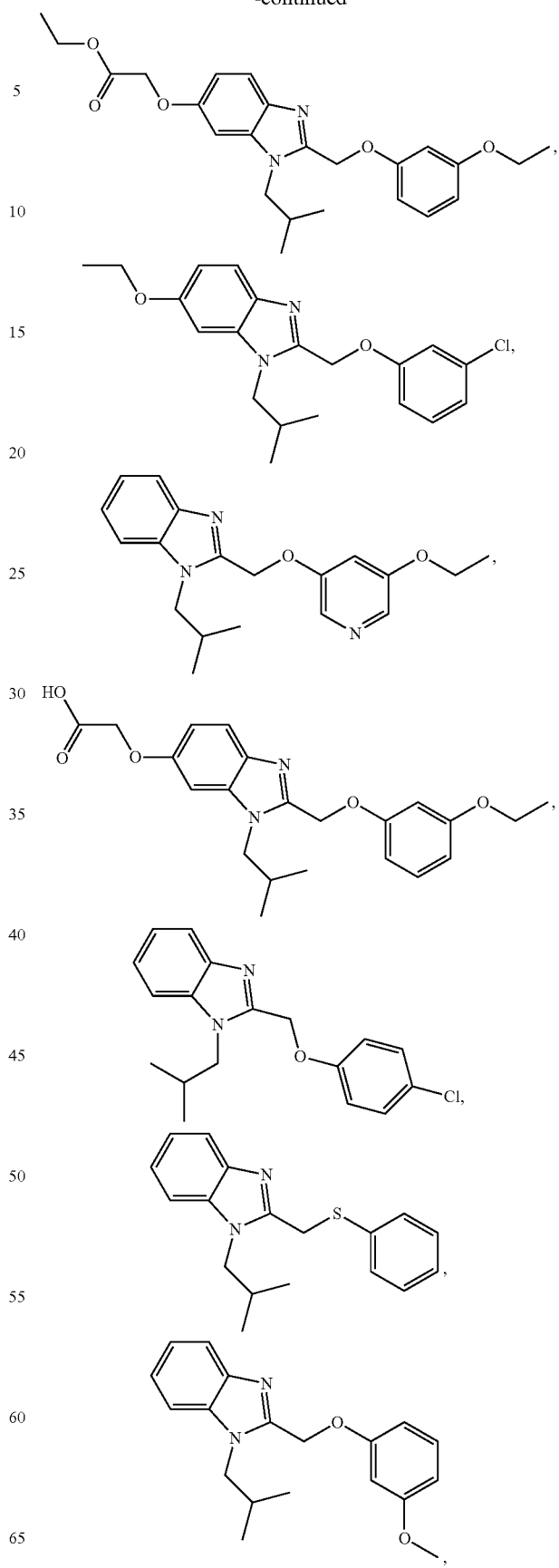

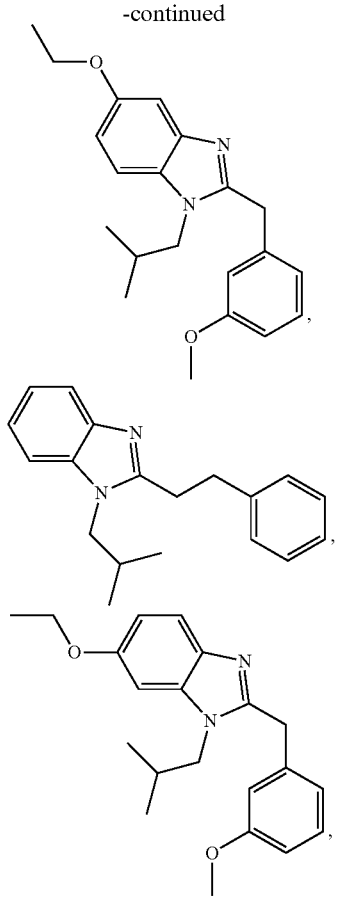

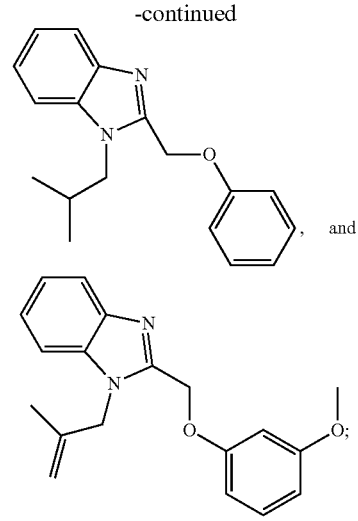

or a pharmaceutically acceptable salt thereof.

General Experimental:

Proton NMR spectra were measured at 60 MHz on a Varian T-60A spectrometer or at 300 MHz on a Varian Inova 300 spectrometer. Chemical shifts are expressed in ppm. High pressure liquid chromatography analyses were performed using an Agilent series 1100 HPLC instrument with an Alltech Alltima $C_{18}$ 5μ, 250×4.6 mm, flow: 1 mL/min at 40° C. Elution was isocratic using a mixture of $H_2O$, A1 (made up of 700 mL $H_2O$, 300 mL MeOH, 3 mL $Et_3N$, and enough phosphoric acid to give a pH of 3.4), and MeOH.

Compound #s 1 and 2

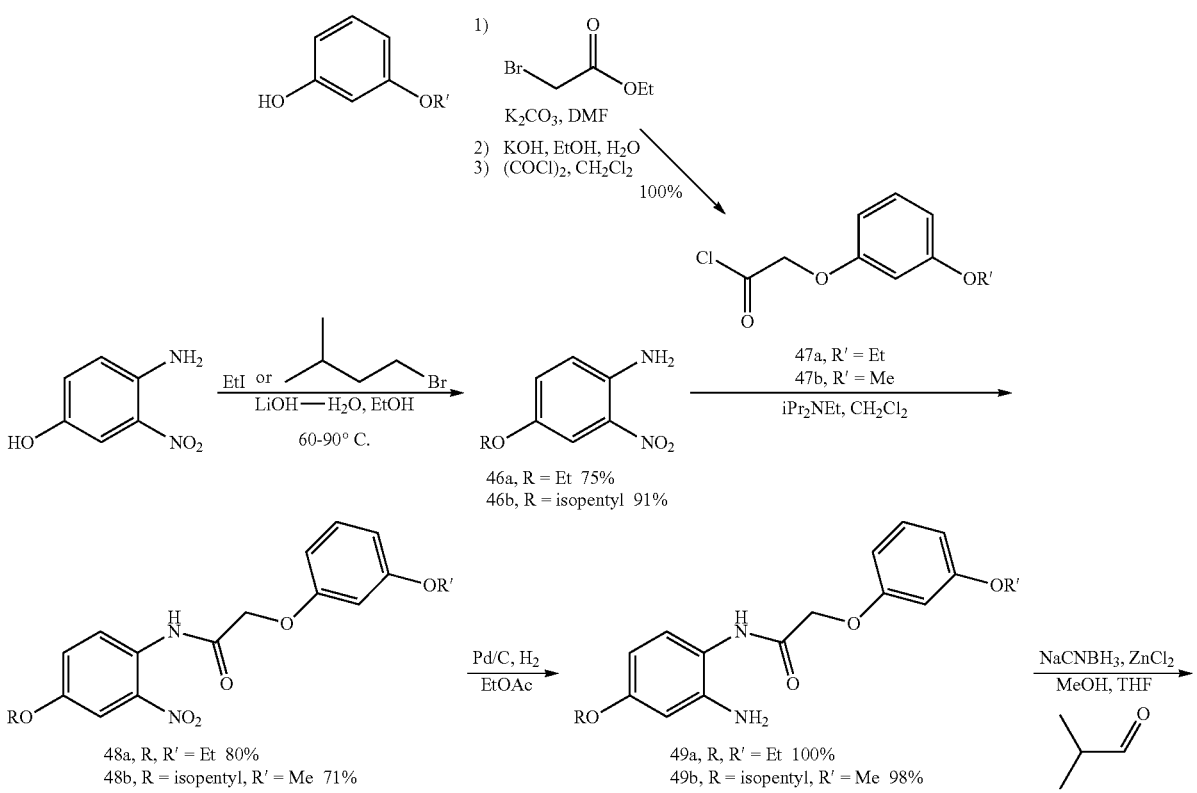

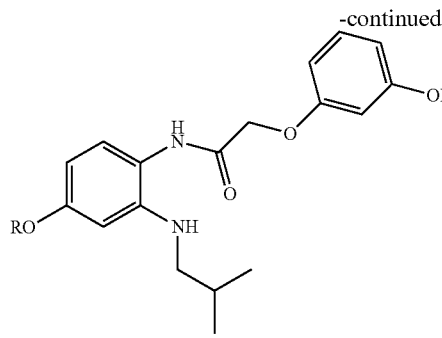 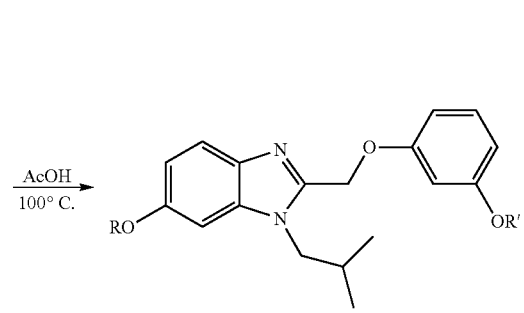

50a, R, R' = Et 100%  
50b, R = isopentyl, R' = Me 94%

Compound #1; R, R' = Et 83%  
Compound #2; R = isopentyl, R' = Me 87%

2-(3-Ethoxyphenoxy)acetyl chloride (47a)

A 500 mL flask fitted with a stir-bar and septum with an Ar inlet was charged with 3-ethoxyphenol (20.4 g, 148 mmol), $K_2CO_3$ (28.5 g, 222 mmol), and DMF (250 mL). To the resultant solution was added ethyl bromoacetate (27.1 g, 18.0 mL, 162 mmol) and the mixture stirred overnight. The solids were filtered off and rinsed with EtOAc (500 mL). The filtrate was washed with saturated aqueous $NH_4Cl$ (2×250 mL), $H_2O$ (2×250 mL), and brine (200 mL), filtered through phase separation paper, and concentrated in vacuo to give 33.6 g of ethyl 3-ethoxyphenoxyacetate as a colorless oil (100%). $^1$H NMR (60 MHz, $CDCl_3$): δ 7.2-6.9 (m, 1H), 6.6-6.3 (m, 3H), 4.6 (s, 2H), 4.2 (qt, 2H), 4.0 (qt, 2H), 1.4 (t, 3H), 1.3 (t, 3H) ppm. HPLC analysis (0:10:90 $H_2O$:A1:MeOH) showed a purity of 98% with a retention time of 5.3 min.

A 1 L flask fitted with a stir-bar was charged with the ethyl ester from above (33.2 g, 148 mmol) and EtOH (400 mL). To the resultant solution was added KOH (16.6 g, 296 mmol) in $H_2O$ (60 mL) forming a thick suspension of crystals. The mixture was stirred for 45 min, then 1M HCl (300 mL) was added to give a solution with a pH of ~1. The mixture was concentrated in vacuo to ~300 mL. The resultant crystals were filtered, pressed with rubber dam, and rinsed with $H_2O$ (3×40 mL). The crystals were dried to give 29.0 g of 3-ethoxyphenoxyacetic acid as a white, crystalline solid (100%). $^1$H NMR (60 MHz, $CDCl_3$): δ 7.2-6.9 (m, 2H), 6.6-6.3 (m, 2H), 4.6 (s, 2H), 4.0 (qt, 2H), 1.5 (t, 3H) ppm. HPLC analysis (0:10:90 $H_2O$:A1:MeOH) showed a purity of greater than 99% with a retention time of 3.3 min.

A 250 mL flask fitted with a stir-bar, addition funnel, and an Ar inlet was charged with 3-ethoxyphenoxyacetic acid (13.0 g, 66.3 mmol) from above, $CH_2Cl_2$ (80 mL), and DMF (0.2 mL). To the resultant solution was added oxalyl chloride (2M in $CH_2Cl_2$, 41.4 mL, 82.8 mmol) over 30 min. The solution was stirred overnight then concentrated in vacuo to give 14.4 g of 47a as an oil/solid mix (100%). HPLC analysis (15:10:75 $H_2O$:A1:MeOH) showed a purity of 95% with a retention time of 4.5 min.

4-Ethoxy-2-nitroaniline (46a)

A 500 mL 3-neck flask fitted with a stir-bar, condenser, and an Ar inlet was charged with 4-amino-3-nitrophenol (12.0 g, 77.9 mmol), ethyl iodide (15.2 g, 8.00 mL, 97.3 mmol), $LiOH \cdot H_2O$ (6.55 g, 156 mmol), and EtOH (120 mL). The resultant solution was heated at 60° C. overnight. Another 3 mL of ethyl iodide and 1 g of $LiOH \cdot H_2O$ were added, and the mixture was stirred at 60° C. overnight again. The solution was cooled and partitioned with EtOAc (250 mL) and $H_2O$ (200 mL). The organic phase was washed with 1% aqueous LiOH (2×200 mL), $H_2O$ (200 mL), and brine (200 mL), filtered through phase separation paper, and concentrated in vacuo to a dark red solid. The crude solid was triturated with hexanes:EtOAc 8:1 (50 mL). The solid was filtered, pressed with rubber dam, and rinsed with hexanes (3×10 mL). The material was dried to give 10.7 g of 46a as a red solid (75%). $^1$H NMR (60 MHz, $CDCl_3$): δ 7.5 (d, 1H), 7.0 (dd, 1H), 6.7 (d, 1H), 5.9 (bs, 2H), 4.0 (qt, 2H), 1.4 (t, 3H) ppm. HPLC analysis (15:10:75 $H_2O$:A1:MeOH) showed a purity of 96% with a retention time of 4.2 min.

N-(4-Ethoxy-2-nitrophenyl)-2-(3-ethoxyphenoxy) acetamide (48a)

A 1 L 3-neck flask fitted with a stir-bar, addition funnel, and an Ar inlet was charged with aniline 46a (9.57 g, 52.6 mmol) and $CH_2Cl_2$ (200 mL). The resultant solution was cooled in an ice bath and $iPr_2NEt$ (20.4 g, 27.5 mL, 158 mmol) was added followed by acid chloride 47a (14.1 g, 65.7 mmol) in $CH_2Cl_2$ (120 mL) over 30 min. The mixture stirred at rt overnight. The red solution was diluted with $CH_2Cl_2$ (250 mL) and was washed with saturated aqueous $NH_4Cl$ (200 mL), saturated $NaHCO_3$ (200 mL), and brine (200 mL). The organic phase was filtered through phase separation paper and concentrated in vacuo to an orange solid. The solid was triturated with EtOH (75 mL), filtered, pressed with a rubber dam, and rinsed with EtOH (3×20 mL). The solid dried to give 14.3 g of 48a as a yellow solid (80%). $^1$H NMR (300 MHz, $CDCl_3$): δ 11.36 (s, 1H), 8.78 (d, 1H), 7.72 (d, 1H), 7.30-7.20 (m, 2H), 6.67-6.59 (m, 3H), 4.66 (s, 2H), 4.09 (qt, 2H), 4.07 (qt, 2H), 1.44 (t, 3H), 1.42 (t, 3H) ppm. HPLC analysis (0:10:90 $H_2O$:A1:MeOH) showed a purity of 98% with a retention time of 4.8 min.

N-(2-Amino-4-ethoxyphenyl)-2-(3-ethoxyphenoxy) acetamide (49a)

A 350 mL hydrogenation vessel was charged with nitroarene 48a (14.2 g, 39.4 mmol) and EtOAc (150 mL). To the resultant suspension was added 10% Pd/C (1.5 g). The mixture was hydrogenated on a Parr shaker at 58 psi overnight. The catalyst was filtered off on glass fiber paper and rinsed with EtOAc (75 mL). The filtrate was concentrated in vacuo to give 13.1 g of 49a as a white solid (100%). $^1$H NMR (300 MHz, $CDCl_3$): δ 8.01 (s, 1H), 7.27 (d, 1H), 7.24 (d, 1H), 7.08 (d, 1H), 6.63-6.55 (m, 3H), 6.40-3.32 (m, 2H), 4.64 (s, 2H), 4.04 (qt, 2H), 3.99 (qt, 2H), 3.82 (bs, 2H), 1.44 (t, 3H), 1.41 (t, 3H) ppm. HPLC analysis (10:10:80 H$_2$O:A1:MeOH) showed a purity of 98% with a retention time of 3.7 min.

N-[4-Ethoxy-2-(isobutylamino)phenyl]-2-(3-ethoxyphenoxy)acetamide (50a)

A 1 L 3-neck flask fitted with a stir-bar, addition funnel, and an Ar inlet was charged with aniline 49a (11.0 g, 33.3 mmol), THF (110 mL), and MeOH (30 mL). To the resultant solution was added isobutyraldehyde (3.36 g, 4.25 mL, 46.6 mmol), and the mixture was stirred for 15 min at rt. Meanwhile, in a 250 mL flask fitted with a stir-bar and septum with an Ar inlet, NaCNBH$_3$ (1M in THF, 47 mL, 46.6 mmol) was added to MeOH (100 mL) followed by ZnCl$_2$ (1M in Et$_2$O, 23 mL, 23.3 mmol) forming a cloudy mixture. After stirring 20 min, this mixture was added to the above aniline solution. The mixture stirred overnight at rt. Another 4.25 mL isobutyraldehyde was added, followed by a second addition of the same volume of the NaCNBH$_3$/ZnCl$_2$ mixture as made previously. The mixture stirred at rt overnight. Another 2 mL of isobutyraldehyde was then added, and the mixture stirred overnight again. The cloudy solution was diluted with EtOAc (500 mL) and washed with saturated NaHCO$_3$ (2×400 mL) and brine (250 mL). The solution was filtered through phase separation paper and concentrated in vacuo to give 15.1 g of a white solid. The solid was collected with hexanes (20 mL) and rinsed with hexanes (2×10 mL). The material was dried to give 13.1 g of 50a as a white solid (100%). $^1$H NMR (300 MHz, CDCl$_3$): δ 7.80 (s, 1H), 7.25 (d, 1H), 7.15 (d, 1H), 6.63-6.55 (m, 3H), 6.32-6.24 (m, 2H), 4.70 (s, 2H), 4.04 (qt, 2H), 4.03 (qt, 2H), 3.76 (bt, 1H), 2.84 (t, 2H), 1.82 (nonet, 1H), 1.43 (t, 3H), 1.41 (t, 3H), 0.84 (d, 6H) ppm. HPLC analysis (5:10:85 H$_2$O:A1:MeOH) showed a purity of 99% with a retention time of 5.0 min.

6-Ethoxy-2-(3-ethoxy-phenoxymethyl)-1-isobutyl-1H-benzimidazole (Compound #1)

A 250 mL flask fitted with a stir-bar, condenser, and an Ar inlet was charged with amine 50a (12.5 g, 32.3 mmol) and AcOH (120 mL). The resultant solution was heated in a 100° C. bath for 3 hr. The mixture was cooled and concentrated in vacuo to a pale, orange solid. The solid was partitioned with EtOAc (150 mL) and saturated NaHCO$_3$ (100 mL). The organic phase was washed with brine (100 mL), filtered through phase separation paper, and concentrated in vacuo to an orange oil. The oil was crystallized with hexanes (25 mL), filtered, and rinsed with hexanes (2×15 mL). The material dried to give 9.9 g of Compound #1 as an off-white solid (83%). $^1$H NMR (300 MHz, CDCl$_3$): δ 7.66 (d, 1H), 7.21 (t, 1H), 6.94 (dd, 1H), 6.82 (d, 1H), 6.71-6.62 (m, 2H), 6.56 (dd, 1H), 5.33 (s, 2H), 4.10 (qt, 2H), 4.05 (t, 2H), 4.03 (qt, 2H), 2.35 (nonet, 1H), 1.48 (t, 3H), 1.43 (t, 3H), 0.98 (d, 6H) ppm. HPLC analysis (0:10:90 H$_2$O:A1:MeOH) showed a purity of 99% with a retention time of 4.6 min.

2-(3-Methoxyphenoxy)acetyl chloride (47b)

A 500 mL flask fitted with a stir-bar, addition funnel, and an Ar inlet was charged with 3-methoxyphenoxyacetic acid (20.0 g, 110 mmol), CH$_2$Cl$_2$ (120 mL), and DMF (0.2 mL). Oxalyl chloride (2M in CH$_2$Cl$_2$, 69 mL, 137 mmol) was added to the resultant solution over 45 min forming an orange solution. The solution stirred overnight at rt. The solution was concentrated in vacuo to give 22.7 g of 47b as an orange oil (100%). HPLC analysis (15:10:75 H$_2$O:A1:MeOH) showed a purity of 93% with a retention time of 3.9 min.

4-(3-Methylbutoxy)-2-nitroaniline (46b)

A 500 mL 3-neck flask fitted with a stir-bar, condenser, and an Ar inlet was charged with 4-amino-3-nitrophenol (12.0 g, 77.9 mmol), 1-bromo-3-methylbutane (14.7 g, 97.3 mmol), LiOH.H$_2$O (6.55 g, 156 mmol), and EtOH (120 mL). The resultant solution was heated at reflux overnight. Another 3 mL of 1-bromo-3-methylbutane and 1 g of LiOH.H$_2$O were added, and the mixture was heated at reflux overnight again. The solution was cooled and partitioned with EtOAc (250 mL) and H$_2$O (200 mL). The organic phase was washed with 1% aqueous LiOH (2×200 mL), H$_2$O (200 mL), and brine (200 mL), filtered through phase separation paper, and concentrated to a dark red solid. The material was dried to give 15.9 g of 46b as a red solid (91%). $^1$H NMR (60 MHz, CDCl$_3$): δ 7.2 (d, 1H), 7.0 (dd, 1H), 6.7 (d, 1H), 6.0 (bs, 2H), 3.9 (t, 2H), 1.8-1.4 (m, 3H), 1.0 (d, 6H) ppm. HPLC analysis (15:10:75 H$_2$O:A1:MeOH) showed a purity of 94% with a retention time of 8.6 min.

N-[4-(3-Methylbutoxy)-2-nitrophenyl]-2-(3-methoxyphenoxy)acetamide (48b)

A 1 L 3-neck flask fitted with a stir-bar, addition funnel, and an Ar inlet was charged with aniline 46b (12.0 g, 53.5 mmol) and CH$_2$Cl$_2$ (200 mL). The resultant solution was cooled in an ice bath and iPr$_2$NEt (20.7 g, 28 mL, 161 mmol) was added followed by acid chloride 47b (12.9 g, 64.2 mmol) in CH$_2$Cl$_2$ (120 mL) over 10 min. The mixture was stirred at rt overnight. The red solution was diluted with CH$_2$Cl$_2$ (250 mL) and washed with saturated aqueous NH$_4$Cl (200 mL), saturated NaHCO$_3$ (200 mL), and brine (200 mL). The solution was filtered through phase separation paper and concentrated in vacuo to a red-brown solid. The solid was collected with EtOH (30 mL), pressed with rubber dam, and rinsed with EtOH (3×15 mL). The solid dried to give 15.0 g of 48b as a yellow solid (71%). $^1$H NMR (300 MHz, CDCl$_3$): δ 9.78 (d, 1H), 7.73 (d, 1H), 7.29-7.22 (m, 2H), 6.68-6.60 (m, 3H), 4.65 (s, 2H), 4.05 (t, 2H), 3.86 (s, 3H), 1.86 (nonet, 1H), 1.72 (qt, 2H), 1.00 (d, 6H) ppm. HPLC analysis (0:10:90 H$_2$O:A1:MeOH) showed a purity of 97% with a retention time of 6.2 min.

N-[2-Amino-4-(3-methylbutoxy)phenyl]-2-(3-methoxyphenoxy)acetamide (49b)

A 350 mL hydrogenation vessel was charge with nitroarene 48b (15.0 g, 38.6 mmol) and EtOH (150 mL). To the resultant suspension was added 10% Pd/C (1.4 g). The mixture was hydrogenated on a Parr shaker at 58 psi overnight. The reduction was incomplete as analyzed by HPLC and contained a large amount of ppt mixed with the catalyst. The catalyst was filtered on glass fiber paper and rinsed with EtOAc (100 mL). The filtrate was concentrated in vacuo to a yellow solid and taken up in EtOAc (150 mL). To the resultant solution was added 10% Pd/C (0.5 g). The mixture was further hydrogenated at 55 psi overnight. The catalyst was filtered off on glass fiber paper and rinsed with EtOAc (75 mL). The filtrate was concentrated in vacuo to give 13.0 g of 49b as an off-white solid (98%). $^1$H NMR (300 MHz, CDCl$_3$): δ 7.99 (s, 1H), 7.32-7.23 (m, 1H), 7.10 (d, 1H), 6.67-6.55 (m, 3H), 6.43-6.35 (m, 2H), 4.65 (s, 2H), 3.96 (t, 2H), 3.83 (s, 3H), 3.83 (bs, 2H), 1.83 (nonet, 1H), 1.67 (qt, 2H), 0.96 (d, 6H) ppm. HPLC analysis (10:10:80 H$_2$O:A1:MeOH) showed a purity of 98% with a retention time of 4.8 min.

N-[2-(Isobutylamino)-4-(3-methylbutoxy)phenyl]-2-(3-methoxyphenoxy)acetamide (50b)

A 1 L 3-neck flask fitted with a stir-bar, addition funnel, and an Ar inlet was charged with aniline 49b (11.0 g, 30.7 mmol), THF (110 mL), and MeOH (30 mL). To the resultant solution was added isobutyraldehyde (3.10 g, 3.92 mL, 43.0 mmol), and the mixture stirred 15 min at rt. Meanwhile, in a 250 mL flask fitted with a stir-bar and septum with an Ar inlet, NaCNBH$_3$ (1M in THF, 43 mL, 43.0 mmol) was added to MeOH (100 mL) followed by ZnCl$_2$ (1M in Et$_2$O, 21.5 mL, 21.5 mmol) forming a cloudy mixture. After stirring 20 min, this mixture was added to the above aniline solution. The mixture was stirred overnight at rt. Another 4.0 mL isobutyraldehyde was added, followed by a second addition of the same volume of the NaCNBH$_3$/ZnCl$_2$ mixture as made previously. The mixture stirred at rt overnight. Another 2 mL of isobutyraldehyde was then added, and the mixture stirred overnight again. The cloudy solution was diluted with EtOAc (500 mL) and washed with saturated NaHCO$_3$ (2×400 mL) and brine (250 mL). The solution was filtered through phase separation paper and concentrated in vacuo to a waxy, orange solid. The solid was collected with hexanes (20 mL) and rinsed with hexanes (2×10 mL). The material dried to give 10.7 g of 50b as a pale orange solid. A second crop of 1.20 g was collected (94%). $^1$H NMR (300 MHz, CDCl$_3$): δ 7.85 (s, 1H), 7.31-7.23 (m, 1H), 7.16 (d, 1H), 6.65-6.56 (m, 3H), 6.33-6.24 (m, 2H), 4.70 (s, 2H), 3.96 (t, 2H), 3.82 (s, 3H), 3.75 (bt, 1H), 2.84 (t, 2H), 1.83 (nonet, 2H), 1.67 (qt, 2H), 0.97 (d, 6H), 0.95 (d, 6H) ppm. HPLC analysis (5:10:85 H$_2$O:A1:MeOH) showed a purity of 98% with a retention time of 6.9 min.

1-Isobutyl-2-(3-methoxy-phenoxymethyl)-6-(3-methyl-butoxy)-1H-benzimidazole (Compound #2)

A 250 mL flask fitted with a stir-bar, condenser, and an Ar inlet was charged with amine 50b (10.7 g, 25.8 mmol) and AcOH (110 mL). The resultant solution was heated in a 100° C. bath for 3 hr. The mixture was cooled and concentrated in vacuo to an orange solid. The solid was partitioned with EtOAc (150 mL) and saturated NaHCO$_3$ (100 mL). The organic phase was then washed with brine (100 mL), filtered through phase separation paper, and concentrated in vacuo to 10.6 g of a red oil. The oil was chromatographed on silica gel eluting the product with 10-15% EtOAc in hexanes. The product fractions were concentrated in vacuo to give 8.9 g of Compound #2 as an orange oil, which slowly crystallized (87%). $^1$H NMR (300 MHz, CDCl$_3$): δ 7.66 (d, 1H), 7.22 (t, 1H), 7.27 (t, 1H), 6.93 (dd, 1H), 6.82 (d, 1H), 6.69 (dd, 1H), 6.63 (t, 1H), 6.57 (dd, 1H), 5.32 (s, 2H), 4.06 (t, 2H), 4.04 (d, 2H), 3.81 (s, 3H), 2.36 (nonet, 1H), 1.90 (nonet, 1H), 1.74 (qt, 2H), 1.00 (d, 6H), 0.97 (d, 6H) ppm. HPLC analysis (0:10:90 H$_2$O:A1:MeOH) showed a purity of 98% with a retention time of 5.8 min.

Compound #s 3 and 4

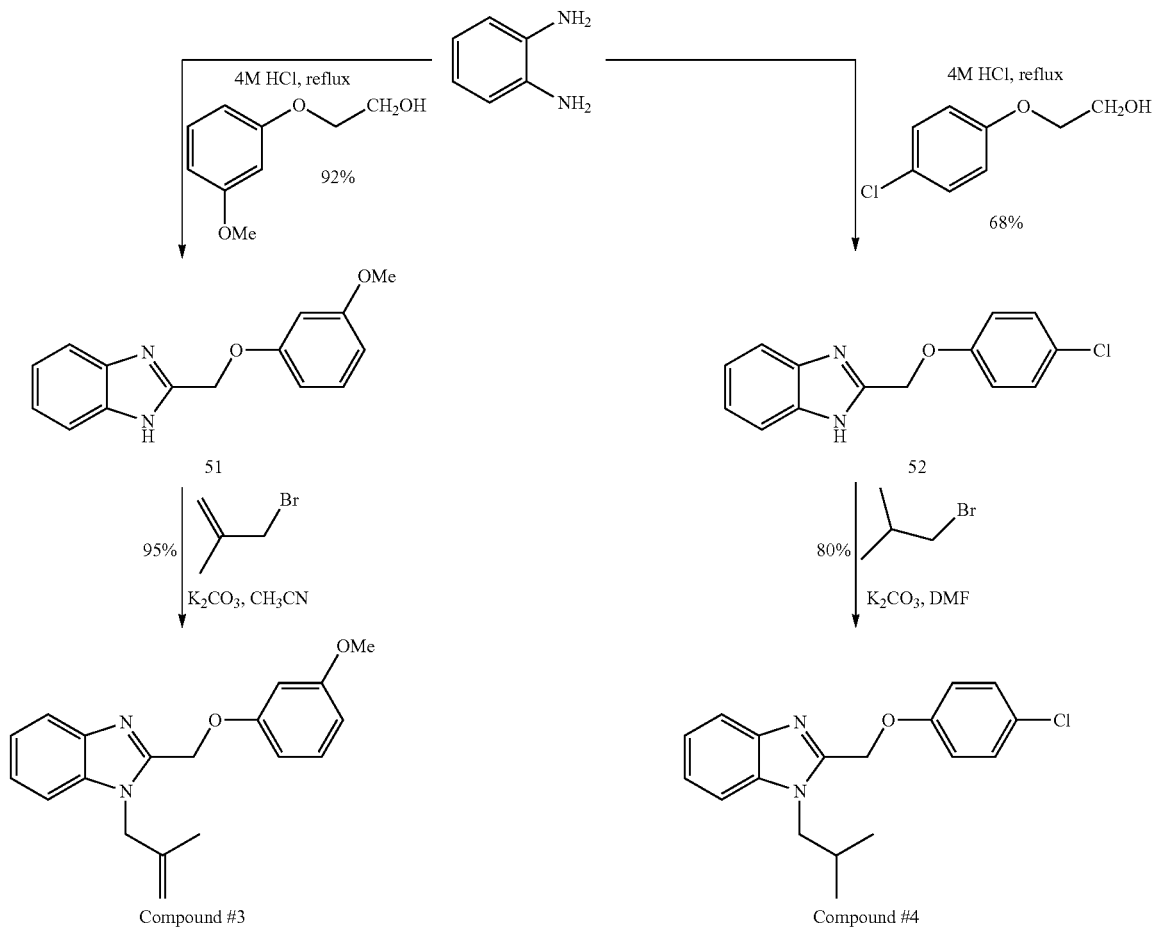

Compound #3

Compound #4

1-(Benzimidazol-2-ylmethoxy)-3-methoxybenzene (51)

A suspension of phenylenediamine (15.12 g, 0.14 mol) and 3-methoxyphenoxyacetic acid (25.5 g, 0.14 mol) in 4M HCl (150 mL) was refluxed overnight under Ar. The reaction mixture was cooled in an ice bath. The solid was collected and washed with cold $H_2O$ (200 mL). To the solid was added $CH_2Cl_2$ (150 mL) and saturated $NaHCO_3$ (150 mL). After stirring for 1 hr, the organic phase was separated, washed with brine (75 mL), filtered through phase separation filter paper and concentrated in vacuo to give 32.7 g (92%) of 51 as an oil which solidified. The HPLC analysis showed a purity of 98%. $^1$H NMR (60 MHz, $CDCl_3$): δ 10.0 (br s, 1H), 6.3-7.9 (m, 8H), 5.0 (s, 2H), 3.7 (s, 3H) ppm.

1-[1-(2-methylprop-2-enyl)benzimidazol-2-ylmethoxy]-3-methoxybenzene (Compound #3)

To a solution of 51 (16.51 g, 0.065 mol) in $CH_3CN$ (150 mL) was added $K_2CO_3$ (17.94 g, 0.13 mol) followed by addition of 3-bromo-2-methylpropene (8.78 g, 0.065 mol) under Ar. The resulting mixture was stirred at rt overnight. The reaction mixture was filtered, and the filter cake was washed with $CH_3CN$ (100 mL). The filtrate was concentrated in vacuo to give an oil. The oil was chromatographed on 150 g of silica gel with 30 g of anhydrous $Na_2SO_4$ on top packed with hexanes. The column was eluted with 150 mL portions of 10% EtOAc in hexanes for fractions 1-5, 20% EtOAc in hexanes for fractions 6-14 and 25% EtOAc for fraction 15-16. The product was eluted in fractions 7-16 (TLC solvent: 50% EtOAc in hexanes) to give 19 g (95%) of Compound #3 as a viscous oil. HPLC analysis showed a purity of 99%. $^1$H NMR for HCl salt (300 MHz, $CD_3OD$): δ 7.9 (m, 2H), 7.7 (m, 2H), 7.3 (t, 1H), 6.65-6.8 (m, 3H), 5.7 (s, 2H), 5.2 (s, 2H), 5.1 (s, 1H), 4.9 (s, 1H), 4.7 (s, 1H), 3.8 (s, 3H), 1.85 (s, 3H).

1-(Benzimidazol-2-ylmethoxy)-4-chlorobenzene (52)

A suspension of phenylene diamine (10.8 g, 0.1 mol) and 4-chlorophenoxyacetic acid (18.66 g, 0.1 mol) in 4M HCl (150 mL) was refluxed overnight under Ar. The reaction mixture was then cooled in an ice bath. The solid was collected and washed with $H_2O$ (150 mL). To the solid was added MeOH (100 mL), $CH_2Cl_2$ (400 mL) and 20% aqueous NaOH (300 mL). After stirring for 30 min, the organic phase was separated, filtered through phase separation filter paper, and concentrated in vacuo to give a solid. This solid was triturated with hexanes (150 mL), collected, washed with hexanes (100 mL), and dried to give 17.5 g (68%) of 52 as a pink solid. The HPLC analysis showed a purity of 100%. $^1$H NMR (60 MHz, $d_6$-DMSO): δ 11.5 (br s, 1H), 6.9-7.5 (m, 8H), 5.3 (s, 2H).

1-[1-(2-methylpropyl)benzimidazol-2-ylmethoxy]-4-Chlorobenzene (Compound #4)

To a solution of 52 (5.17 g, 0.02 mol) in DMF (50 mL) was added $K_2CO_3$ (5.53 g, 0.04 mol) followed by addition of 2-methylpropyl bromide (5.2 g, 0.038 mol) under Ar. The resulting mixture was stirred at rt for 48 hr. HPLC analysis showed that the reaction was not complete. The reaction mixture was further heated at 90° C. for 8 hr, at which point HPLC analysis showed the reaction was complete. The reaction mixture was cooled to rt and filtered. The filter cake was washed with EtOAc (100 mL). The filtrate was washed with $H_2O$ (2×75 mL) and brine (100 mL), filtered through phase separation filter paper, and concentrated in vacuo to give an oil (6 g) which solidified. The solid was triturated with hexanes (50 mL), filtered, washed with hexanes (25 mL), and dried to give 4.25 g (80%) of Compound #4. HPLC analysis showed a purity of 100%. $^1$H NMR (300 MHz, $CDCl_3$): δ 7.85 (m, 1H), 7.45-7.25 (m, 5H), 7.05 (m. 2H), 5.4 (s, 2H), 4.1 (d, 2H), 2.35 (m, 1H), 1.0 (d, 6H) ppm.

Compound #s 5 through 9

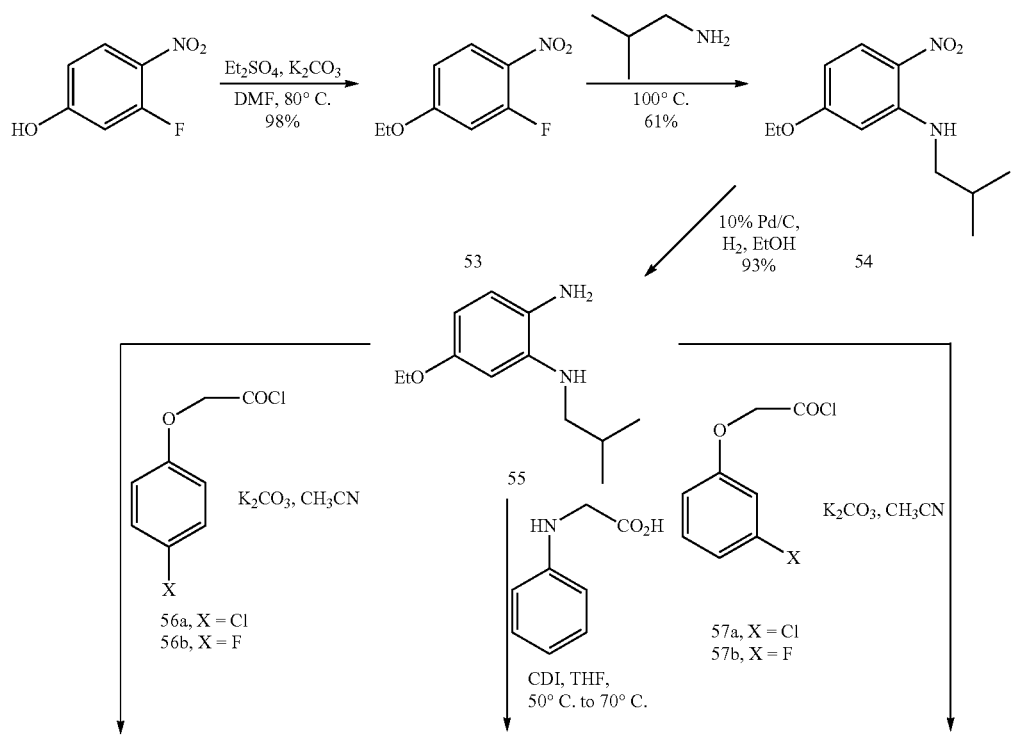

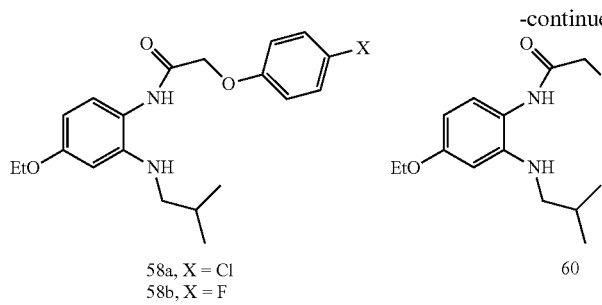
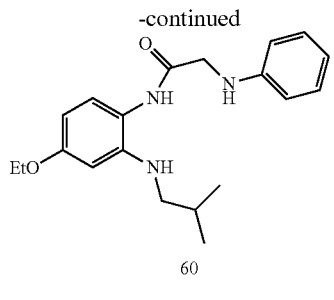
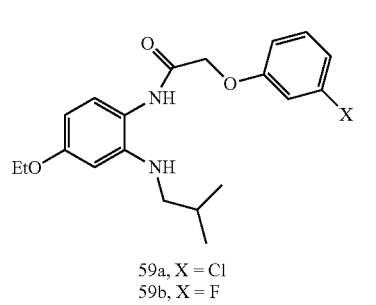

58a, X = Cl
58b, X = F

60

59a, X = Cl
59b, X = F

↓ HOAc, 100° C.

↓ HOAc, 100° C.

↓ HOAc, 100° C.

Compound #7, X = Cl, 70%
Compound #8, X = F, 37%

Compound #9, 25%

Compound #5, X = Cl, 30%
Compound #6, X = F, 62%

4-Ethoxy-2-fluoro-1-nitrobenzene (53)

To a solution of 3-fluoro-4-nitrophenol (9.9 g, 0.063 mol) and diethyl sulfate (12.17 g, 0.079 mol) in DMF (100 mL) was added $K_2CO_3$ (17.39 g, 0.126 mol). The resulting mixture was stirred at 80° C. for 90 min and then cooled to rt. The reaction mixture was diluted with $H_2O$ (200 mL) and extracted with 25% EtOAc in hexanes (2×100 mL). The combined organic phases were washed with brine (100 mL), filtered through phase separation filter paper, and concentrated in vacuo to give 11.5 g (98%) of 53 as an orange-yellow solid. $^1$H NMR (60 MHz, $CDCl_3$): δ 8.8-7.7 (m, 1H), 6.6-6.2 (m, 2H), 4.0 (q, 2H), 1.4 (t, 3H) ppm.

(5-Ethoxy-2-nitrophenol)(2-methylpropyl)amine (54)

A 1 L pressure vessel was charged with 53 (10.9 g, 0.059 mol) and isobutylamine (150 mL). The vessel was sealed and heated on steam-bath for 1 hr. After cooling to rt, the mixture was diluted with $CH_2Cl_2$ and washed with $H_2O$ (2×100 mL) and brine (100 mL). The organic phase was filtered through phase separation filter paper and concentrated in vacuo to give an oil which solidified. The oil was triturated with hexanes (25 mL) and filtered. The solid was collected and dried to give 8.6 g (61%) of 54 as orange-yellow solid. HPLC analysis showed a purity of 99%. $^1$H NMR (60 MHz, $CDCl_3$): δ 8.2 (bs, 1H), 7.9-7.7 (m, 1H), 6.2-6.0 (m, 2H), 4.0 (q, 2H), 3.0 (t, 3H), 2.3-1.6 (m, 1H), 1.4 (t, 3H), 1.0 (d, 6H) ppm.

(2-Amino-5-ethoxyphenyl)(2-methylpropyl)amine (55)

A 500 mL hydrogenation vessel was charged with 54 (10.7 g, 0.045 mol) and warm EtOH (100 mL). 10% Pd/C (2 g) was added and the mixture was hydrogenated on a Parr shaker. The catalyst was filtered and rinsed with EtOH (50 mL). The filtrate was concentrated in vacuo to give 8.7 g (93%) of 55 as dark purple oil. HPLC analysis showed a purity of 98%. $^1$H NMR (60 MHz, $CDCl_3$): δ 6.4 (d, 1H), 6.2 (m, 2H), 3.9 (q, 2H), 3.4-2.4 (m, 5H), 2.1-1.6 (m, 1H), 1.4 (t, 3H), 1.0 (d, 6H) ppm.

2-(4-Chlorophenoxy)acetyl chloride (56a)

To a suspension of 4-chlorophenoxy acetic acid (9.32 g, 0.05 mol) in $CH_2Cl_2$ (150 mL) was added oxalyl chloride (32.5 mL, of 2M in $CH_2Cl_2$) and DMF (0.2 mL). The resulting mixture was stirred at rt overnight under Ar. The mixture was concentrated in vacuo to give 10.3 g (100%) of 56a as colorless oil. $^1$H NMR (60 MHz, $CDCl_3$): δ 7.0-6.7 (m, 4H), 4.8 (s, 2H) ppm.

2-(4-Fluorophenoxy)acetyl chloride (56b)

The compound was prepared as above in 100% yield. $^1$H NMR (60 MHz, $CDCl_3$): δ 7.0-6.8 (m, 4H), 4.7 (s, 2H) ppm.

2-(3-Chlorophenoxy)acetyl chloride (57a)

The compound was prepared as above in 100% yield. $^1$H NMR (60 MHz, $CDCl_3$): δ 7.3-6.7 (m, 4H), 4.9 (s, 2H) ppm.

2-(3-Fluorophenoxy)acetyl chloride (57b)

The compound was prepared as above in 100% yield. $^1$H NMR (60 MHz, $CDCl_3$): δ 7.3-6.4 (m, 4H), 4.7 (s, 2H) ppm.

2-(4-Chlorophenoxy)-N-{4-ethoxy-2-[(2-methylpropyl)amino]phenyl}acetamide (58a)

To a mixture of 55 (2.08 g, 0.01 mol) and $K_2CO_3$ (3.45 g, 0.025 mol) in $CH_3CN$ (25 mL) was added a solution of 56a (2.46 g, 0.012 mol) in $CH_3CN$ (25 mL) over 45 min at rt under Ar. After stirring at rt for 3 hr, EtOAc (100 mL) and saturated $NaHCO_3$ (100 mL) where added. The resulting mixture was stirred at rt for 10 min. The organic phase was washed with saturated $NaHCO_3$ (1×75 mL) and brine (1×100 mL), filtered through phase separation filter paper, and concentrated in vacuo to give a solid. The solid was triturated with hexanes (100 mL), filtered, and dried to give 3.5 g (93%) of 58a as a purple solid. HPLC analysis showed a purity of 91%. $^1$H NMR (60 MHz, $CDCl_3$): δ 7.6 (brs, 1H), 7.3-6.7 (m, 5H), 6.2

(m, 2H), 4.6 (s, 2H), 4.0 (q, 2H), 3.6 (brs, 1H), 2.8 (brs, 2H), 2.0-1.6 (m, 1H), 1.4 (t, 3H), 1.0 (d, 6H) ppm.

2-(4-Fluorophenoxy)-N-{4-ethoxy-2-[(2-methylpropyl)amino]phenyl}acetamide (58b)

The compound was prepared as above. HPLC analysis showed a purity of 95%. $^1$H NMR (60 MHz, CDCl$_3$): δ 7.7 (brs, 1H), 7.1-6.7 (m, 5H), 6.2 (m, 2H), 4.6 (s, 2H), 3.9 (q, 2H), 3.7 (brs, 1H), 2.8 (brd, 2H), 2.1-1.6 (m, 1H), 1.4 (t, 3H), 1.0 (d, 6H) ppm.

2-(3-Chlorophenoxy)-N-{4-ethoxy-2-[(2-methylpropyl)amino]phenyl}acetamide (59a)

The compound was prepared as above and used in the next step without further purification.

2-(3-Fluorophenoxy)-N-{4-ethoxy-2-[(2-methylpropyl)amino]phenyl}acetamide (56b)

The compound was prepared as above and used in the next step without further purification.

4-Chloro-1-{[6-ethoxy-1-(2-methylpropyl)benzimidazole-2-yl]methoxy}benzene. (Compound #7)

A solution of 58a (3.5 g, 0.0093 mol) in AcOH (50 mL) was heated at 100° C. for 1 hr. The reaction mixture was concentrated in vacuo, and to the residue was added CH$_2$Cl$_2$ (100 mL) and 37% aqueous ammonia (15 mL). The organic phase was washed with saturated NaHCO$_3$ (2×75 mL) and brine (1×75 mL), filtered through phase separation filter paper, and concentrated in vacuo to give 3.0 g of a pink solid. The solid was chromatographed on 50 g of silica gel with 10 g anhydrous sodium sulfate on top packed with hexanes. The column was eluted with 25 mL portions of hexanes for fractions 1-4, 25% EtOAc in hexanes for fractions 5-8, and 35% EtOAc in hexanes for fractions 9-20. The product eluted in fractions 11-20 to give 2.5 g (70%) of Compound #7 as a tan solid. HPLC analysis showed a purity of 97%. $^1$H NMR (300 MHz, CDCl$_3$): δ 7.7 (d, 1H), 7.3-6.8 (m, 6H), 5.35 (s, 2H), 4.1 (m, 4H), 2.3 (m, 1H), 1.45 (t, 3H), 1.0 (d, 6H) ppm.

4-Fluoro-1-{[6-ethoxy-1-(2-methylpropyl)benzimidazole-2-yl]methoxy}benzene (Compound #8)

The compound was prepared as above in 37% yield. HPLC analysis showed a purity of 99%. $^1$H NMR (300 MHz, CDCl$_3$): δ 7.7 (d, 1H), 7.2-6.7 (m, 6H), 5.2 (s, 2H), 4.1 (m, 4H), 2.2 (m, 1H), 1.5 (t, 3H), 1.0 (d, 6H) ppm.

3-Chloro-1-{[6-ethoxy-1-(2-methylpropyl)benzimidazole-2-yl]methoxy}benzene (Compound #5)

The compound was prepared as above in 30% yield. HPLC analysis showed a purity of 96%. $^1$H NMR (300 MHz, CDCl$_3$); δ 7.7 (d, 1H), 7.3-6.8 (m, 6H), 5.35 (s, 2H), 4.15 (q, 2H), 4.0 (d, 2H), 2.35 (m, 1H), 1.5 (t, 3H), 1.0 (d, 6H) ppm.

3-Fluoro-1-{[6-ethoxy-1-(2-methylpropyl)benzimidazole-2-yl]methoxy}benzene (Compound #6)

The compound was prepared as above in 62% yield. HPLC analysis showed a purity of 100%. $^1$H NMR (300 MHz, CDCl$_3$): δ 7.7 (d, 1H), 7.3 (m, 1H), 6.95-6.7 (m, 5H), 5.3 (s, 2H), 4.1 (q, 2H), 4.0 (d, 2H), 2.3 (m, 1H), 1.5 (t, 3H), 1.0 (d, 6H) ppm.

N-{4-ethoxy-2-[(2-methylpropyl)amino]phenyl}-2(phenylamino)acetamide (60)

A solution of N-phenylglycine (1.51 g, 0.01 mol) and N,N'-carbonyldiimidazole (1.62 g, 0.01 mol) in THF (25 mL) was heated at 50° C. for 30 min under Ar. A solution of 55 (2.08 g, 0.01 mol) in THF (50 mL) was then added over 30 min, and the resulting mixture was heated at 70° C. overnight. The reaction mixture was concentrated in vacuo, and the residue was dissolved in EtOAc (100 mL) and washed with saturated NaHCO$_3$ (2×100 mL) and brine (100 mL). The organic phase was filtered through phase separation filter paper and concentrated in vacuo to give 3.0 g of a red oil which was used in the next step without further purification.

{[6-Ethoxy-1-(2-methylpropyl)benzimidazole-2-yl]methyl}phenylamine (Compound #9)

A solution of 60 (3.0 g, 0.0088 mol) in AcOH (50 mL) was heated at 100° C. for 3 hr. The mixture was then concentrated in vacuo. To the residue was added EtOAc (100 mL) and 37% aqueous ammonia (15 mL). The organic phase was washed with saturated NaHCO$_3$ (2×75 mL) and brine (75 mL), filtered through phase separation filter paper, and concentrated in vacuo to give 3.0 g of a red oil. The oil was chromatographed on 30 g of silica gel with 10 g of anhydrous sodium sulfate on top packed with hexanes. The column was eluted with 25 mL portions of 10% CH$_2$Cl$_2$ in hexanes for fractions 1-4, 10% EtOAc in hexanes for fractions 5-8, 15% EtOAc in hexanes for fractions 9-12, 20% EtOAc in hexanes for fractions 13-16, 25% EtOAc in hexanes for fractions 17-20, 30% EtOAc in hexanes for fractions 21-24 and 35% EtOAc in hexanes for fractions 25-28. The product was eluted in fractions 21-27 to give 0.7 g (25%) of compound #9 as a brown oil. HPLC analysis showed a purity of 96%. $^1$H NMR (300 MHz, CDCl$_3$): δ 7.65 (d, 1H), 7.3 (m, 2H), 6.95-6.75 (m, 5H), 4.7 (brs, 1H), 4.5 (s, 2H), 4.1 (q, 2H), 3.95 (d, 2H), 2.3 (m, 1H), 1.5 (t, 3H), 1.0 (d, 6H) ppm.

Compound #10

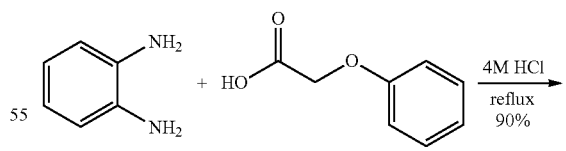

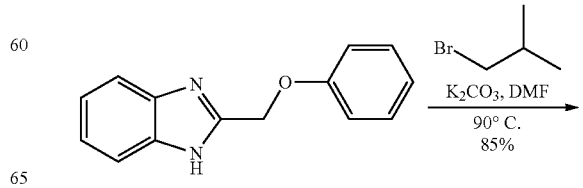

61

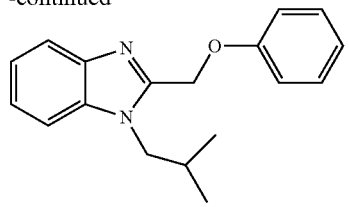

Compound #10

2-(Phenoxymethyl)-1H-benzimidazole (61)

A 100 mL flask fitted with a stir-bar and condenser was charged with 1,2-phenylenediamine (9.94 g, 92.1 mmol), phenoxyacetic acid (14.0 g, 92.1 mmol), and 4M HCl (140 mL). The suspension was heated in a 130° C. bath forming a green solution. After 18 hr, the reaction had gone to completion as monitored by HPLC. The mixture was cooled in an ice bath forming a solid. The solid was filtered, pressed with rubber dam, and rinsed with $H_2O$ (2×15 mL). The residue was partitioned with EtOAc (300 mL) and saturated $NaHCO_3$ (125 mL). The organic phase was washed with brine (100 mL), filtered through phase separation paper, and concentrated in vacuo to give 18.5 g of 61 as an off-white solid (90%). $^1$H NMR (300 MHz, $CDCl_3$): δ 10.08 (bs, 1H), 7.82-7.40 (bm, 2H), 7.35-7.26 (m, 4H), 7.08-6.95 (m, 3H), 5.40 (s, 2H) ppm. HPLC analysis (15:10:75 $H_2O$:A1:MeOH) showed a purity of greater than 99% with a retention time of 4.2 min.

1-Isobutyl-2-(phenoxymethyl)-1H-benzimidazole (Compound #10)

A 500 mL flask fitted with a stir-bar, addition funnel, and Ar inlet was charged with 2-(phenoxymethyl)-1H-benzimidazole (61) (10.0 g, 44.6 mmol) and $K_2CO_3$ (12.3 g, 89.2 mmol). DMF (120 mL) was added followed by 1-bromo-2-methylpropane (9.17 g, 66.9 mmol). The suspension was heated in a 90° C. bath for 18 hr. Another 900 mg of 1-bromo-2-methylpropane were then added, and the mixture stirred another 3 hr until the starting material was down to 2% as measured by HPLC. The mixture was cooled to rt, and the solids were filtered off and rinsed with EtOAc (250 mL). The filtrate was then washed with saturated $NH_4Cl$ (2×200 mL), $H_2O$ (2×200 mL), and brine (100 mL), filtered through phase separation paper, and concentrated in vacuo to a yellow oil. Upon standing the oil crystallized, and was subsequently triturated with hexanes:EtOAc 20:1 (30 mL). The crystals were filtered and rinsed with hexanes (2×10 mL). Upon drying, 10.2 g of Compound #10 were obtained as an off-white, crystalline solid (84%). $^1$H NMR (300 MHz, $CDCl_3$): δ 7.82 (m, 1H), 7.42-7.28 (m, 5H), 7.12 (d, 2H), 7.02 (t, 1H), 5.40 (s, 2H), 4.14 (d, 2H), 2.35 (sept, 1H), 0.98 (d, 6H) ppm. HPLC analysis (5:10:85 $H_2O$:A1:MeOH) showed a purity of 98% with a retention time of 4.9 min and 2% starting material with a retention time of 3.4 min. Extension of the reaction time should reduce the percentage of starting material.

Compound #11

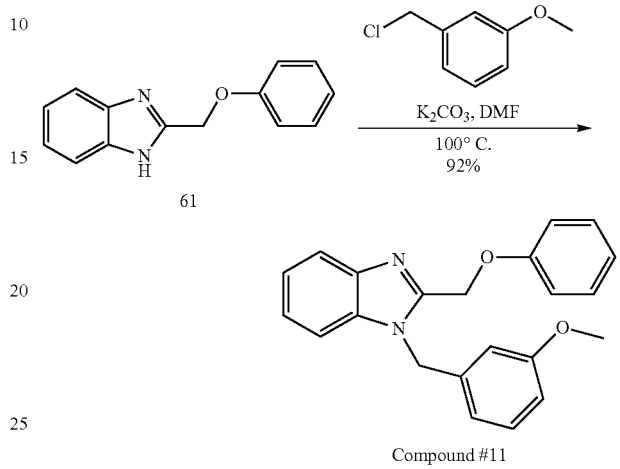

Compound #11

1-(3-Methoxybenzyl)-2-(phenoxymethyl)-1H-benzimidazole (Compound #11)

A 50 mL flask fitted with a stir-bar and a septum with an Ar inlet was charged with 2-(phenoxymethyl)-1 H-benzimidazole (61) (1.00 g, 4.46 mmol), $K_2CO_3$ (1.23 g, 8.92 mmol), and DMF (12 mL). 3-Methoxybenzyl chloride (769 mg, 4.91 mmol) was added, and the suspension was heated in a 100° C. bath for 2 hr. The mixture was cooled, and the solids were filtered off and rinsed with EtOAc (50 mL). The filtrate was then washed with sat'd $NH_4Cl$ (2×30 mL), $H_2O$ (2×30 mL), and brine (20 mL), filtered through phase separation paper, and concentrated in vacuo to a yellow oil. Upon standing the oil crystallized, and was subsequently collected with hexanes:EtOAc 30:1 (15 mL). Upon drying, 1.41 g of Compound #11 were obtained as an off-white crystalline solid (92%). $^1$H NMR (300 MHz, $CDCl_3$): δ 7.84 (m, 1H), 7.36-7.25 (m, 5H), 7.21 (t, 1H), 6.82 (dd, 1H), 6.68 (d, 1H), 6.62 (m, 1H), 5.52 (s, 2H), 5.36 (s, 2H), 3.64 (s, 3H) ppm. HPLC analysis (5:10:85 $H_2O$:A1:MeOH) showed a purity of greater than 99% with a retention time of 4.8 min.

Compound #s 12 and 13

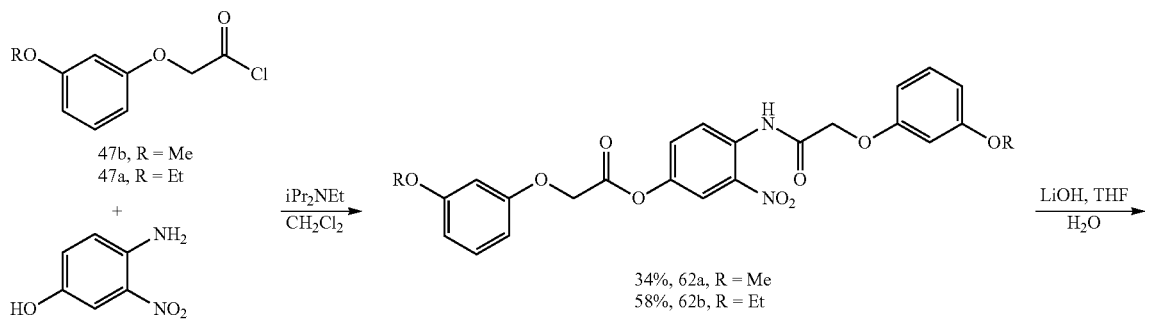

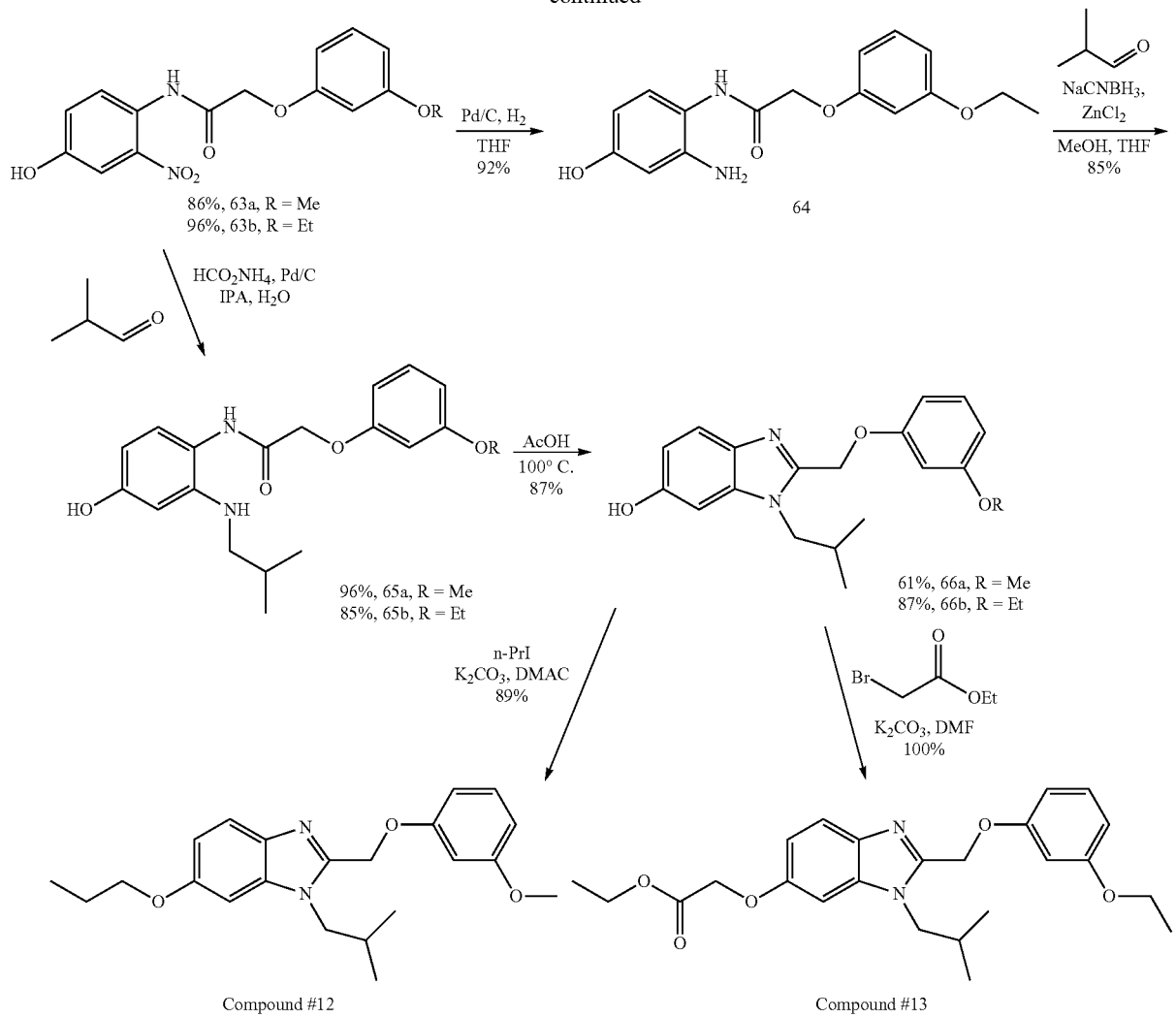

Compound #12

4-[2-(3-Methoxyphenoxy)acetylamino]-3-nitrophenyl 2-(3-methoxyphenoxy) acetate (62a)

To a solution of 4-amino-3-nitrophenol (7.7 g, 0.05 mol) and N,N-diisopropylethylamine (25.8 g, 0.2 mol) in $CH_2Cl_2$ (200 mL) was added a solution of 47b (25.0 g, 0.125 mol) in $CH_2Cl_2$ (200 mL) over 1 hr at 0° C. under Ar. The resulting mixture was stirred at rt for 48 hr. The reaction mixture was then washed with saturated $NaHCO_3$ (2×200 mL) and brine (200 mL), filtered through phase separation filter paper, and concentrated in vacuo to give a dark brown oil. The oil was chromatographed on 265 g silica gel with 70 g of anhydrous sodium sulfate on top packed with hexanes. The column was eluted with 200 mL portions of hexanes for fractions 1-2, 10% EtOAc in hexanes for fractions 3-4, 20% EtOAc in hexanes for fractions 5-8, 30% EtOAc in hexanes for fractions 9-12, 40% EtOAc in hexanes for fractions 13-20 and 50% EtOAc in hexanes for fractions 21-32. The pure product was eluted in fractions 11-18 to give 5.3 g of 59a as a yellow solid. Remaining fractions of impure product were combined and concentrated in vacuo to give a yellow solid. The solid was triturated with 100 mL of 25% EtOAc in hexanes. The impurity of insoluble solid was filtered off. The filtrate was then concentrated in vacuo, and the residue was chromatographed on 125 g silica gel with 25 g of anhydrous sodium sulfate on top packed with hexanes. The column was eluted with 100 mL portions of 15% EtOAc in hexanes for fractions 1-4, 25% EtOAc in hexanes for fractions 5-8, 30% EtOAc in hexanes for fractions 9-10 and 40% EtOAc in hexanes for fractions 11-22. The pure product was eluted in fractions 10-14 (HPLC analysis) to give 3.0 g of 62a as yellow solid. The total weight of 62a amounted to 8.3 g (34%). HPLC analysis showed a purity of 97%. $^1H$ NMR (60 MHz, $CDCl_3$): δ 11.6 (s, 1H), 9.0 (d, 1H), 8.1 (s, 1H), 7.5 (m, 1H), 7.3 (m, 2H), 6.6 (m, 6H), 4.9 (s, 2H), 4.7 (s, 2H), 3.8 (d, 6H) ppm.

N-(4-Hydroxy-2-nitrophenol)-2-(3-methoxyphenoxy)acetamide (63a)

To a suspension of 62a (6.75 g, 0.014 mol) in THF (75 mL) was added a solution of $LiOH \cdot H_2O$ (0.65 g, 0.0154 mol) in $H_2O$ (8 mL) at rt. After 2 hr, HPLC analysis showed the reaction was complete. The reaction mixture was acidified with 3M HCl and partitioned with EtOAc (75 mL). The organic phase was washed with saturated $NaHCO_3$ (2×50 mL), $H_2O$ (50 mL), and brine (75 mL), filtered through phase separation filter paper, and concentrated in vacuo to give a solid residue. The solid was triturated with hexanes (50 mL), then filtered to give 3.7 g (86%) of 63a as a yellow solid. HPLC analysis showed a purity of 99%. $^1$H NMR (60 MHz, d$_6$-DMSO): δ 7.8 (m, 1H), 7.4-7.0 (m, 3H), 6.7-6.4 (m, 3H), 4.7 (s, 2H), 4.0 (brs, 1H), 3.8 (s, 3H), 3.6 (brs, 1H) ppm.

N-{4-Hydroxy-2-[(2-methylpropyl)amino]phenyl}-2-(3-methoxyphenoxy) acetamide (65a)

To a suspension of 10% Pd/C (4.5 g, 50% H$_2$O wet paste) in isopropanol (250 mL) was added a solution of ammonium formate (10.71 g, 0.17 mol) in H$_2$O (20 mL). The suspension was stirred for 5 min and then 63a (5.23 g, 0.017 mol) was added as a solid in one portion. After stirring for 45 min, isobutyraldehyde (4.9 g, 0.068 mol) was added in three portions in 15 min intervals. After 45 min, the reaction mixture was filtered and the filter cake was washed with isopropanol (150 mL). The filtrate was concentrated in vacuo. The resultant residue was taken up in CH$_2$Cl$_2$ (150 mL) and washed with H$_2$O (75 mL) and brine (75 mL), filtered through phase separation filter paper, and concentrated in vacuo to give 5.6 g (96%) of 65a as a glass. HPLC analysis showed a purity of 88%. $^1$H NMR (60 MHz, CDCl$_3$): δ 7.8 (brs, 1H), 7.4-6.0 (m, 8H), 5.7 (brs, 1H), 4.6 (s, 2H), 3.7 (s, 3H), 2.7 (brd, 2H), 2.1-1.3 (m, 1H), 1.0 (d, 6H) ppm.

2-[(3-Methoxyphenoxy)methyl]-1-(2-methylpropyl)-6-hydroxybenzimidazole (66a)

A solution of 65a (5.5 g, 0.016 mol) in AcOH (50 mL) was heated at 100° C. for 1 hr. The reaction mixture was then concentrated in vacuo. The residue was dissolved in CH$_2$Cl$_2$ (100 mL), washed with saturated NaHCO$_3$ (2×75 mL) and brine (75 mL), filtered through phase separation filter paper, and concentrated in vacuo to give a solid. The solid was triturated with EtOAc (35 mL), collected, and dried to give 3.7 g (71%) of 66a. HPLC analysis showed a purity of 80%. The solid was chromatographed on 75 g silica gel with 25 g of anhydrous sodium sulfate on top packed with hexanes. The column was eluted with 50 mL portions of 10% EtOAc in hexanes for fractions 1-4, 25% EtOAc in hexanes for fractions 5-8, and 50% EtOAc in hexanes for fractions 9-28. The pure product was eluted in fractions 15-20 (HPLC analysis) to give 3.2 g (61%) of 66a as a white solid. HPLC analysis showed a purity of 97%. $^1$H NMR (60 MHz, CDCl$_3$): δ 7.7 (d, 1H), 7.4-6.4 (m, 6H), 6.8 (br s, 1H), 5.0 (s, 2H), 4.1 (d, 2H), 3.7 (s, 3H), 2.5-1.6 (m, 1H), 1.0 (d, 6H) ppm.

3-Methoxy-1-{[1-(2-methylpropyl)-6-propoxybenzimidazol-2-yl]methoxy}benzene (Compound #12)

To a solution of 63a (0.75 g, 0.0023 mol) and propyl iodide (0.78 g, 0.0046 mol) in DMAC (10 mL) was added K$_2$CO$_3$ (0.95 g, 0.0069 mol). The resulting mixture was stirred at rt overnight. H$_2$O (25 mL) was then added, and the mixture was extracted with 50% EtOAc in hexanes (2×30 mL). The combined organic phases were washed with brine (30 mL), filtered through phase separation filter paper, and concentrated in vacuo to give 0.9 g of a viscous oil. The oil was chromatographed on 10 g silica gel with 5 g of anhydrous sodium sulfate on top packed with hexanes. The column was eluted with 50 mL portions of hexanes for fractions 1-2, 15% EtOAc in hexanes for fractions 3-6, and 20% EtOAc in hexanes for fractions 7-10. The pure product was eluted in fractions 4-9 (HPLC analysis) to give 0.75 g (89%) of compound #12 as a colorless oil. HPLC analysis showed a purity of 100%. $^1$H NMR (300 MHz, CDCl$_3$): δ 7.7 (d, 1H), 7.2 (m, 1H), 6.9 (m, 1H), 6.8 (m, 1H), 6.75-6.6 (m, 3H), 5.3 (s, 2H), 4.05-3.95 (m, 4H), 3.8 (s, 3H), 2.35 (m, 1H), 1.85 (m, 2H), 1.1 (t, 3H), 1.0 (d, 6H) ppm.

Compound #13

4-[2-(3-Ethoxyphenoxy)acetylamino]-3-nitrophenyl 2-(3-ethoxyphenoxy)acetate (62b)

A 1 L 3-neck flask fitted with a stir-bar, addition funnel, and an Ar inlet was charged with 4-amino-3-nitrophenol (10.1 g, 65.6 mmol) and CH$_2$Cl$_2$ (250 mL). To the resultant suspension cooled in an ice bath, was added iPr$_2$NEt (33.8 g, 45.6 mL, 262 mmol) forming a deep red solution. Acid chloride 47a (32.4 g, 151 mmol) in CH$_2$Cl$_2$ (250 mL) was then added over 30 min. The mixture stirred overnight at rt. Saturated NaHCO$_3$ (300 mL) was added, and the organic phase was washed with saturated NaHCO$_3$ (300 mL) and brine (200 mL). The solution was filtered through phase separation paper and concentrated in vacuo to 36 g of a yellow-brown solid. The solid was triturated with EtOAc:hexanes 1:1 (150 mL), filtered, pressed with rubber dam, and rinsed with EtOAc:hexanes 1:1 (2×25 mL). The material dried to give 19.4 g of 62b as a yellow solid (58%). $^1$H NMR (300 MHz, CDCl$_3$): δ 11.58 (s, 1H), 8.99 (d, 1H), 8.08 (d, 1H), 7.49 (dd, 1H), 7.33-7.18 (m, 2H), 6.71-6.48 (m, 6H), 4.89 (s, 2H), 4.66 (s, 2H), 4.06 (qt, 2H), 4.03 (qt, 2H), 1.43 (t, 3H), 1.42 (t, 3H) ppm. HPLC analysis (10:10:80 H$_2$O:A1:MeOH) showed a purity of 93% with a retention time of 11.0 min.

2-(3-Ethoxyphenoxy)-N-(4-hydroxy-2-nitrophenyl) acetamide (63b)

A 500 mL 3-neck flask fitted with a stir-bar and an Ar inlet was charged with 52b (19.4 g, 38.0 mmol) and THF (250 mL). To the resultant yellow solution was added LiOH.H$_2$O (1.83 g, 43.7 mmol) in H$_2$O (20 mL), forming a deep red solution. After 3 hr at rt, 1M HCl (50 mL) was added, and the mixture was partitioned with EtOAc (300 mL). The organic phase was washed with saturated NaHCO$_3$ (3×200 mL) and brine (200 mL), filtered through phase separation paper, and concentrated in vacuo to 13.5 g of a yellow solid. The solid was triturated with CH$_2$Cl$_2$:hexanes 2:1 (100 mL), filtered, pressed with rubber dam, and rinsed with CH$_2$Cl$_2$:hexanes 2:1 (2×20 mL). The solid was dried to give 12.1 g of 63b as a bright yellow solid (96%). $^1$H NMR (300 MHz, CDCl$_3$): δ 11.13 (s, 1H), 9.52 (s, 1H), 8.55 (d, 1H), 7.62 (d, 1H), 7.18-7.08 (m, 2H), 6.57-6.47 (m, 3H), 4.52 (s, 2H), 3.96 (qt, 2H), 1.34 (t, 3H) ppm. HPLC analysis (10:10:80 H$_2$O:A1:MeOH) showed a purity of 97% with a retention time of 5.5 min.

N-(2-Amino-4-hydroxyphenyl)-2-(3-ethoxyphenoxy)acetamide (64)

A 2 L hydrogenation vessel was charged with phenol 63b (12.1 g, 36.4 mmol) and THF (240 mL). To the resultant solution was added 10% Pd/C (1.2 g), and the mixture was hydrogenated at 49 psi for 2 hr. The catalyst was filtered off on glass fiber paper, and concentrated to a red oil. The crude oil crystallized with CH$_2$Cl$_2$ and was triturated with CH$_2$Cl$_2$:hexanes 1:1 (100 mL). The crystals were filtered, pressed with rubber dam, and rinsed with CH$_2$Cl$_2$:hexanes 1:1 (2×20 mL). The crystals were dried to give 10.1 g of 64 as yellow crystals (92%). HPLC analysis (10:10:80 H$_2$O:A1:MeOH) showed a purity of greater than 99% with a retention time of 3.1 min.

2-(3-Ethoxyphenoxy)-N-[4-hydroxy-2-(isobutylamino)phenyl]acetamide (65b)

A 500 mL 3-neck flask fitted with a stir-bar, addition funnel, and an Ar inlet was charged with aniline 64 (9.20 g, 30.4 mmol), THF (100 mL), and MeOH (30 mL). To the resultant solution was added isobutyraldehyde (3.07 g, 3.89 mL, 42.6 mmol), and the mixture stirred 10 min at rt. Meanwhile, in a 250 mL flask fitted with a stir-bar and septum with an Ar inlet, $NaCNBH_3$ (1M in THF, 43 mL, 43 mmol) was added to MeOH (80 mL). $ZnCl_2$ (1M in $Et_2O$, 21 mL, 21 mmol) was next added forming a cloudy mixture which was stirred for 10 min. The mixture was then added to the above aniline solution. The reaction stirred overnight at rt. Another 1.0 mL isobutyraldehyde was added, followed by a second portion of 25% of the original amount of the $NaCNBH_3/ZnCl_2$ mixture as made previously. The mixture stirred at rt overnight. Another 0.5 mL of isobutyraldehyde was then added, and the mixture stirred overnight again. The cloudy solution was diluted with EtOAc (300 mL) and washed with saturated $NaHCO_3$ (2×250 mL) and brine (150 mL). The solution was filtered through phase separation paper and concentrated to 12.1 g of a dark oil. The crude oil was chromatographed on silica gel with the product eluting with 25-33% EtOAc in hexanes. The product fractions were concentrated to give 10.2 g of 65b as a tan solid (85%). $^1$H NMR (300 MHz, $CDCl_3$): δ 7.84 (s, 1H), 7.24 (m, 1H), 6.97 (d, 1H), 6.64-6.52 (m, 3H), 6.16 (d, 1H), 6.09 (dd, 1H), 4.67 (s, 2H), 4.05 (qt, 2H), 2.77 (d, 2H), 1.78 (nonet, 1H), 1.43 (t, 3H), 0.92 (d, 6H) ppm. HPLC analysis (10:10:80 $H_2O$:A1:MeOH) showed a purity of 98% with a retention time of 4.3 min.

2-[(3-Ethoxyphenoxy)methyl]-1-isobutylbenzimidazol-6-ol (66b)

A 250 mL flask fitted with a stir-bar and condenser was charged with amine 65b (10.0 g, 27.9 mmol) and AcOH (100 mL). The resultant solution was heated in a 100° C. bath for 1 hr, then concentrated in vacuo to a brown oil. The oil was taken up in EtOAc (200 mL) and washed with saturated $NaHCO_3$ (2×100 mL) and brine (100 mL). Isopropanol (50 mL) and $CH_2Cl_2$ (50 mL) were added to break the emulsion. The organic solution was filtered through phase separation paper and concentrated in vacuo to a red-tan solid. The solid was triturated with hexanes:EtOAc 9:1 (50 mL), filtered, pressed with rubber dam, and rinsed with hexanes:EtOAc 9:1 (2×20 mL). The solid was dried to give 8.3 g of 66b as a tan solid (87%). $^1$H NMR (300 MHz, $CDCl_3$): δ 8.84 (s, 1H), 7.37 (d, 1H), 7.02 (t, 1H), 6.70 (dd, 1H), 6.65 (d, 1H), 6.48 (dd, 1H), 6.44 (t, 1H), 6.37 (dd, 1H), 5.10 (s, 2H), 3.86 (t, 2H), 3.81 (d, 2H), 2.15 (nonet, 1H), 1.23 (t, 3H), 0.78 (d, 6H) ppm. HPLC analysis (0:10:90 $H_2O$:A1:MeOH) showed a purity of 99% with a retention time of 3.5 min.

[2-(3-Ethoxy-phenoxymethyl)-3-isobutyl-3H-benzimidazol-5-yloxy]-acetic acid ethyl ester (Compound #13)

A 100 mL flask fitted with a stir-bar and septum with an Ar inlet was charged with benzimidazole 66b (3.00 g, 8.81 mmol) and DMF (35 mL). To the resultant solution was added $K_2CO_3$ (1.83 g, 13.2 mmol) followed by ethyl bromoacetate (1.62 g, 1.07 mL, 9.69 mmol). The mixture was stirred at rt overnight. The solids were then filtered off and rinsed with EtOAc (2×50 mL). The filtrate was washed with saturated $NH_4Cl$ (2×75 mL), $H_2O$ (2×75 mL), and brine (75 mL) and filtered through phase separation paper. The organic phase was filtered through a plug of silica gel, rinsed with EtOAc (3×100 mL), and concentrated in vacuo to 4.0 g of a brown oil. 1 g of the crude oil was chromatographed on a Biotage MPLC 25+M silica gel column with the product eluting with 30-36% EtOAc in hexanes. The product fractions were concentrated to give 975 mg of Compound #13 as a yellow oil (100%). $^1$H NMR (300 MHz, $CDCl_3$): δ 7.69 (d, 1H), 7.20 (t, 1H), 6.93 (dd, 1H), 6.88 (d, 1H), 6.67 (dd, 1H), 6.63 (t, 1H), 6.54 (dd, 1H), 5.32 (s, 2H), 4.70 (s, 2H), 4.29 (qt, 2H), 4.05 (qt, 2H), 4.04 (d, 2H), 2.34 (nonet, 1H), 1.41 (t, 3H), 1.32 (t, 3H), 0.97 (d, 6H) ppm. HPLC analysis (0:10:90 $H_2O$:A1:MeOH) showed a purity of 99% with a retention time of 3.9 min.

Compound #14

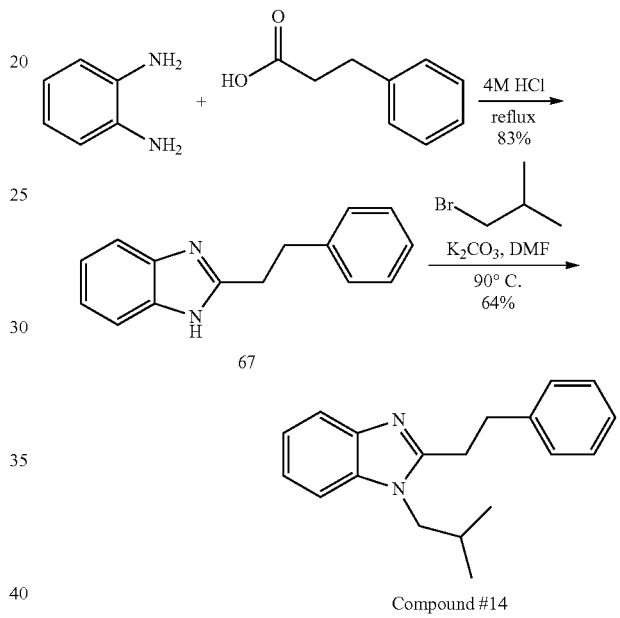

Compound #14

2-(2-Phenylethyl)benzimidazole (67)

A 100 mL flask fitted with a stir-bar and condenser was charged with 1,2-phenylenediamine (2.88 g, 26.6 mmol), hydrocinnamic acid (4.00 g, 26.6 mmol), and 4M HCl (40 mL). The resultant suspension was heated in a 130° C. bath 48 hr. The mixture was cooled, and the precipitate was filtered. The solid was suspended in $H_2O$ (70 mL), and the suspension was brought to pH 11 with 50% aqueous NaOH and stirred overnight. The pH was readjusted from 3 to 11 with 50% NaOH. The solid was filtered, pressed with rubber dam, and rinsed with $H_2O$ (2×10 mL). The material was dried to give 4.9 g of 67 as a white solid (83%). $^1$H NMR (60 MHz, $CDCl_3$): δ 12.3 (s, 1H), 7.6-7.4 (m, 2H), 7.4-6.8 (m, 7H), 3.2 (s, 4H) ppm. HPLC analysis (15:10:75 $H_2O$:A1:MeOH) showed a purity of greater than 99% with a retention time of 3.2 min.

1-Isobutyl-2-(2-phenylethyl)-1H-benzimidazole (Compound #14)

A 100 mL flask fitted with a stir-bar and septum with an Ar inlet was charged with benzimidazole 67 (2.00 g, 9.00 mmol) and $K_2CO_3$ (2.49 g, 18.0 mmol). DMF (25 mL) was added followed by 1-bromo-2-methylpropane (1.84 g, 1.47 mL, 13.5 mmol), and the mixture was heated in a 90° C. bath overnight. Another 1 mL of 1-bromo-2-methylpropane was added and the mixture was heated overnight again. Another addition of 1 mL of 1-bromo-2-methylpropane and 1 g $K_2CO_3$ was executed, and the mixture was heated overnight again. The suspension was cooled, and the solids were filtered off and rinsed with EtOAc (80 mL). The filtrate was washed with saturated $NH_4Cl$ (2×50 mL), $H_2O$ (2×50 mL), and brine (30 mL), filtered through phase separation paper, and concentrated in vacuo to an orange oil. The crude oil was filtered through a plug of silica gel with $CH_2Cl_2$ (100 mL). The filtrate was concentrated in vacuo to give 1.60 g of Compound #14 as a yellow oil (64%). $^1$H NMR (300 MHz, $CDCl_3$): δ 7.80 (m, 1H), 7.35-7.21 (m, 8H), 3.81 (d, 2H), 3.35-3.26 (m, 2H), 3.22-3.13 (m, 2H), 2.16 (nonet, 1H), 0.95 (d, 6H) ppm. HPLC analysis (5:10:85 $H_2O$:A1:MeOH) showed a purity of 96% with a retention time of 4.7 min.

Compound #15

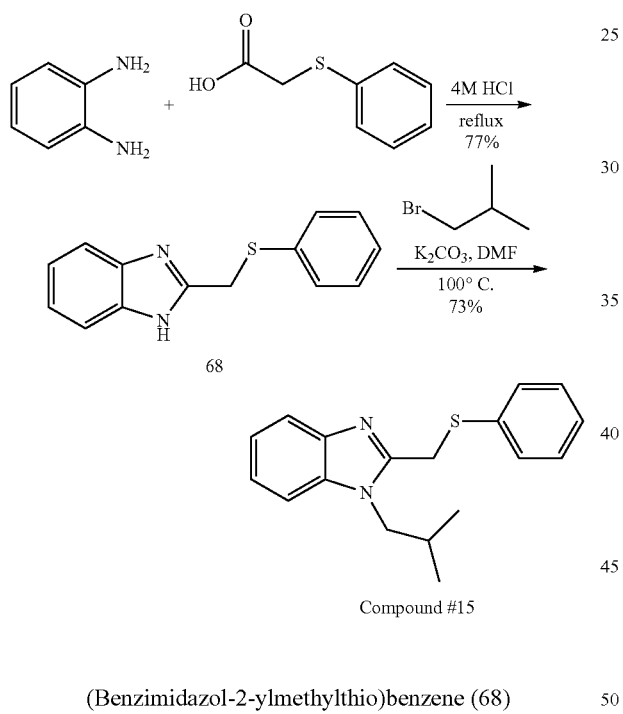

(Benzimidazol-2-ylmethylthio)benzene (68)

A 100 mL flask fitted with a stir-bar and condenser was charged with 1,2-phenylenediamine (2.88 g, 26.6 mmol), (phenylthio)acetic acid (4.00 g, 26.6 mmol), and 4M HCl (40 mL). The resultant suspension was heated in a 130° C. bath 48 hr. The mixture was cooled and concentrated in vacuo to a brown syrup. The syrup was taken up in EtOAc (100 mL) and washed with saturated $NaHCO_3$ (2×75 mL) and brine (50 mL). The solution was filtered through phase separation paper and concentrated in vacuo to a tan solid. The crude solid was triturated with hexanes:EtOAc 6:1 (50 mL), filtered, pressed with rubber dam, and rinsed with hexanes:EtOAc 4:1 (2×10 mL). The material was dried to give 4.4 g of 68 as a tan solid (77%). $^1$H NMR (300 MHz, $CDCl_3$): δ 11.7 (bs, 1H), 7.7-7.4 (m, 2H), 7.4-6.9 (m, 7H), 4.4 (s, 2H) ppm. HPLC analysis (15:10:75 $H_2O$:A1:MeOH) showed a purity of 99% with retention time of 4.0 min.

1-Isobutyl-2-[(phenylthio)methyl]-1H-benzimidazole (Compound #15)

A 100 mL flask fitted with a stir-bar and septum with an Ar inlet was charged with benzimidazole 68 (3.00 g, 12.5 mmol) and $K_2CO_3$ (3.46 g, 25.0 mmol). DMF (35 mL) was added followed by 1-bromo-2-methylpropane (2.56 g, 1.47 mL, 18.7 mmol). The mixture was heated in a 90° C. bath overnight. Another 0.5 mL of 1-bromo-2-methylpropane was added, and the mixture was heated overnight again. The suspension was cooled, and the solids were filtered off and rinsed with EtOAc (100 mL). The filtrate was washed with saturated $NH_4Cl$ (2×75 mL), $H_2O$ (2×75 mL), and brine (50 mL), filtered through phase separation paper, and concentrated in vacuo to a brown oil. The crude oil was filtered through a plug of silica gel with $CH_2Cl_2$ (100 mL). The filtrate was concentrated in vacuo to give 2.70 g of a yellow oil. The oil was crystallized and collected with hexanes to give 2.16 g of Compound #15 as a pale yellow solid (73%). $^1$H NMR (300 MHz, $CDCl_3$): δ 7.75 (m, 1H), 7.44 M, 2H), 7.36-7.21 (m, 6H), 4.42 (s, 2H), 3.99 (d, 2H), 2.27 (nonet, 1H), 0.96 (d, 6H) ppm. HPLC analysis (5:10:85 $H_2O$:A1:MeOH) showed a purity of greater than 99% with a retention time of 5.0 min.

Compound #16

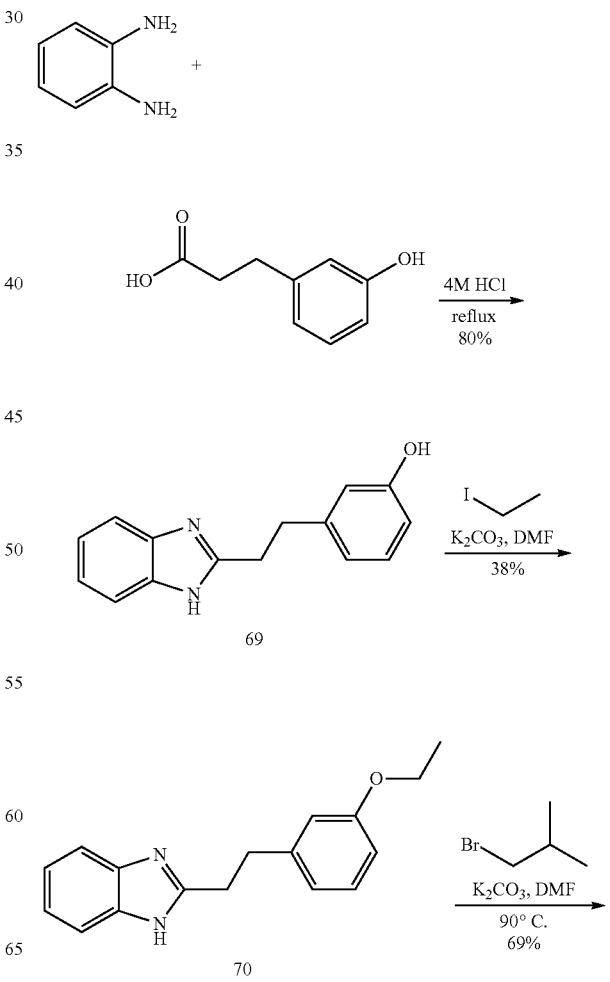

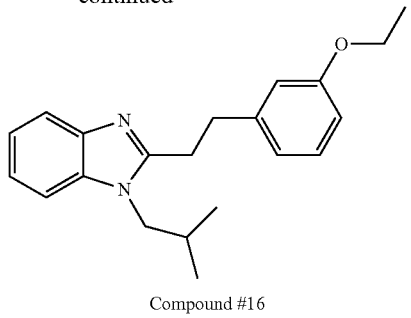

Compound #16

3-(2-Benzimidazol-2-ylethyl)phenol (69)

A 100 mL flask fitted with a stir-bar and a condenser was charged with 1,2-phenylenediamine (3.42 g, 31.6 mmol), 3-hydroxyhydrocinnamic acid (5.25 g, 3.16 mmol), and 4M HCl (50 mL). The mixture was heated in a 135° C. bath overnight. The mixture was cooled in an ice bath, and the precipitate was filtered and rinsed with $H_2O$ (5 mL). The solid was suspended in saturated $NaHCO_3$ (75 mL). 50% aq NaOH was added until pH 11 was attained, and then another portion of saturated $NaHCO_3$ (75 mL) was added. The suspension was stirred overnight. The solid was filtered, pressed with rubber dam, and rinsed with $H_2O$ (2×10 mL). The resultant material was dried to give 6.05 g of 69 as a white solid (80%). $^1$H NMR (60 MHz, $CDCl_3$): δ 7.6-7.4 (m, 2H), 7.4-7.0 (m, 3H), 6.9-6.6 (m, 3H), 5.2 (s, 2H), 3.1 (s, 4H) ppm. HPLC analysis (35:10:55 $H_2O$:A1:MeOH) showed a purity of greater than 99% with a retention time of 3.1 min.

1-(2-Benzimidazol-2-ylethyl)-3-ethoxybenzene (70)

A 100 mL flask fitted with a stir-bar and septum with an Ar inlet was charged with benzimidazole 69 (2.00 g, 8.39 mmol), $K_2CO_3$ (1.74 g, 12.6 mmol), and DMF (20 mL). Ethyl iodide (1.44 g, 0.74 mL, 9.23 mmol) was added, and the mixture stirred at rt overnight. Analysis by HPLC showed a mixture of approximately 1:3:2 starting material:product:diethylbenzimidazole. The solids were filtered off and rinsed with EtOAc (60 mL). The filtrate was washed with saturated aqueous $NH_4Cl$ (2×50 mL), $H_2O$ (2×50 mL), 1% aqueous LiOH (4×50 mL), and brine (25 mL). The solution was filtered through phase separation paper and concentrated to 1.85 g of a yellow oil. The crude oil was chromatographed on silica gel with the product eluting with 25-35% EtOAc in hexanes. The product fractions were concentrated in vacuo to a white solid that was collected with hexanes. The material was dried to give 855 mg of 70 as a white solid (38%). $^1$H NMR (60 MHz, $CDCl_3$): δ 7.8-7.5 (m, 2H), 7.5-7.0 (m, 3H), 6.9-6.6 (m, 3H), 3.8 (qt, 2H), 3.3-2.9 (m, 4H), 1.3 (t, 3H) ppm. HPLC analysis (15:10:75 $H_2O$:A1:MeOH) showed a purity of 99% with a retention time of 3.6 min.

2-[2-(3-Ethoxyphenyl)ethyl]-1-isobutyl-1H-benzimidazole (Compound #16)

A 50 mL flask fitted with a stir-bar and septum with an Ar inlet was charged with benzimidazole 70 (800 mg, 3.00 mmol) and $K_2CO_3$ (829 mg, 6.00 mmol). DMF (10 mL) was added followed by 1-bromo-2-methylpropane (617 mg, 0.489 mL, 4.50 mmol). The mixture was heated in a 90° C. bath overnight. Another 0.5 mL of 1-bromo-2-methylpropane and 300 mg of $K_2CO_3$ were added, and the mixture was heated overnight again. A third addition of 0.5 mL of 1-bromo-2-methylpropane and 300 mg of $K_2CO_3$ were added. The mixture was heated another 4 hr until complete as monitored by HPLC. The suspension was cooled, and the solids were filtered off and rinsed with EtOAc (60 mL). The filtrate was washed with saturated aqueous $NH_4Cl$ (2×50 mL), $H_2O$ (2×50 mL), and brine (30 mL), filtered through phase separation paper, and concentrated in vacuo to an orange-brown oil. The crude oil was filtered through a plug of silica gel with $CH_2Cl_2$ (2×100 mL) and 5% EtOAc in $CH_2Cl_2$ (3×100 mL). The EtOAc/$CH_2Cl_2$ filtrates were concentrated to give 670 mg of Compound #16 as a yellow oil (69%). $^1$H NMR (300 MHz, $CDCl_3$): δ 7.78 (m, 1H), 7.34-7.19 (m, 4H), 6.87-6.76 (m, 3H), 3.98 (qt, 2H), 3.81 (d, 2H), 3.32-3.22 (m, 2H), 3.21-3.11 (m, 2H), 2.17 (nonet, 1H), 1.40 (t, 3H), 0.93 (d, 6H) ppm. HPLC analysis (5:10:85 $H_2O$:A1:MeOH) showed a purity of 99% with a retention time of 5.1 min.

Compound #17

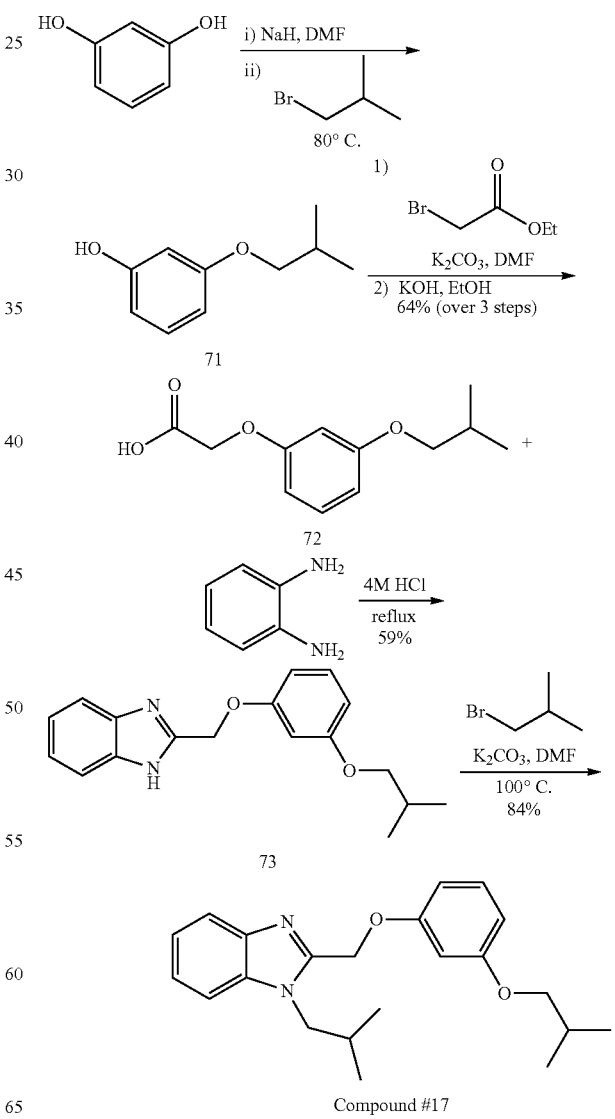

Compound #17

3-Isobutoxyphenol (71)

A 1 L 3-neck flask fitted with a stir-bar, addition funnel, and an Ar inlet was charged with resorcinol (20.0 g, 182 mmol) and DMF (400 mL). To the resultant solution was added NaH (4.82 g, 200 mmol) in two portions, 10 min apart. The mixture stirred at rt 30 min. 1-Bromo-2-methylpropane (37.4 g, 273 mmol) was then added, and the mixture was heated at 80° C. overnight. The mixture was cooled, diluted with EtOAc (300 mL), and washed with $H_2O$ (2×250 mL). The aqueous phases were back-extracted with EtOAc (2×100 mL). The combined organic phases were then diluted with hexanes (500 mL) and washed with half-saturated aqueous $NaHCO_3$ (6×200 mL). The solution was filtered through phase separation paper and concentrated in vacuo to give 13.4 g of 71 as a yellow oil containing 27% dialkylated material as determined by HPLC. The substance was carried on as is. HPLC analysis (5:10:85 $H_2O$:A1:MeOH) showed a purity of 68% with a retention time of 3.9 min and 27% dialkylated material with a retention time of 12.0 min.

2-[3-(Isobutoxy)phenoxy]acetic acid (72)

A 200 mL flask fitted with a stir-bar and a septum with an Ar inlet was charged with phenol 71 (6.00 g, 36.1 mmol, 68% purity), ethyl bromoacetate (6.63 g, 39.7 mmol), and DMF (70 mL). To the resultant solution was added $K_2CO_3$ (7.48 g, 54.1 mmol), and the mixture was stirred at rt 2 hr.

The solids were filtered off and rinsed with EtOAc (100 mL). The filtrate was washed with saturated aqueous $NH_4Cl$ (2×75 mL), $H_2O$ (2×75 mL), and brine (75 mL), filtered through phase separation paper, and concentrated in vacuo to give 9.63 g of ethyl 3-isobutoxyphenoxyacetate as a yellow oil. The material still contained 26% diisobutylated material as detected by HPLC. The substance was carried on as is. HPLC analysis (5:10:85 $H_2O$:A1:MeOH) showed a purity of 71% with a retention time of 5.2 min and 26% dialkylated material with a retention time of 12.0 min.

A 250 mL flask fitted with a stir-bar was charged with ethyl 3-isobutoxyphenoxyacetate (9.11 g, 36.1 mmol, 71% purity) and EtOH (100 mL). To the resultant solution was added KOH (4.05 g, 72.2 mmol) in $H_2O$ (15 mL). The mixture stirred 30 min at rt. 1M HCl was then added until a pH of 2.5 was reached. The mixture was concentrated in vacuo to 75 mL. NaOH (4 g) was added, and the solution was washed with $CH_2Cl_2$ (3×50 mL). 3M HCl was then added until a pH of 3 was attained, and the mixture was extracted with EtOAc (75 mL). The organic phase was washed with brine (50 mL), filtered through phase separation paper, and concentrated in vacuo to give 5.2 g of 72 as an off-white solid (64% from 71). $^1$H NMR (60 MHz, $CDCl_3$): δ 11.4 (s, 1H), 7.3-7.0 (m, 1H), 6.7-6.3 (m, 3H), 4.6 (s, 2H), 3.7 (d, 2H), 2.0 (nonet, 1H), 1.0 (d, 6H) ppm. HPLC analysis (5:10:85 $H_2O$:A1:MeOH) showed a purity of 95% with a retention time of 3.5 min.

1-(Benzimidazol-2-ylmethoxy)-3-isobutoxybenzene (73)

A 250 mL flask fitted with a stir-bar and condenser was charged with 1,2-phenylenediamine (2.46 g, 22.7 mmol), acid 72 (5.10 g, 22.7 mmol), and 4M HCl (50 mL). The resultant suspension was heated in a 125° C. bath for 72 hr. The mixture was cooled, and concentrated in vacuo to a green solid. The solid was triturated with acetone (50 mL), filtered, and rinsed with acetone (2×20 mL). The solid was then triturated with $H_2O$ (50 mL) and filtered. The material was next taken up in MeOH:$H_2O$ 1:1 (75 mL), and the pH was adjusted to 11 with 2M NaOH (10 mL). The mixture was then extracted with EtOAc (100 mL). The organic phase was washed with saturated aqueous $NH_4Cl$ (50 mL) and brine (50 mL), filtered through phase separation paper, and concentrated in vacuo to a light pink glass. The material crystallized to give 3.95 g of 73 as a white solid (59%). $^1$H NMR (60 MHz, $CDCl_3$): δ 7.8-7.6 (m, 2H), 7.5-7.0 (m, 3H), 6.6-6.4 (m, 3H), 5.4 (s, 2H), 3.5 (d, 2H), 1.9 (nonet, 1H), 0.9 (d, 6H) ppm. HPLC analysis (15:10:75 $H_2O$:A1:MeOH) showed a purity of 99% with a retention time of 8.5 min.

2-[(3-Isobutoxyphenoxy)methyl]-1-isobutyl-1H-benzimidazole (Compound #17)

A 100 mL flask fitted with a stir-bar, condenser, and an Ar inlet was charged with benzimidazole 73 (1.73 g, 5.84 mmol) and $K_2CO_3$ (1.62 g, 11.7 mmol). DMF (25 mL) was added followed by 1-bromo-2-methylpropane (1.20 g, 0.95 mL, 8.73 mmol), and the mixture was heated in a 90° C. bath for 5 hr. Another 0.3 mL of 1-bromo-2-methylpropane was added and the mixture was heated overnight. The suspension was cooled, and the solids were filtered off and rinsed with EtOAc (100 mL). The filtrate was washed with saturated aqueous $NH_4Cl$ (2×60 mL), $H_2O$ (2×60 mL), and brine (50 mL), filtered through phase separation paper, and concentrated in vacuo to a yellow oil. The crude oil was chromatographed on silica gel with the product eluting with 10-12% EtOAc in hexanes. The product fractions were concentrated to give 1.73 g of Compound #17 as a colorless oil (84%). $^1$H NMR (300 MHz, $CDCl_3$): δ 7.81 (m, 1H), 7.40 (m, 1H), 7.36-7.24 (m, 2H), 7.20 (t, 1H), 6.71-6.63 (m, 2H), 6.56 (dd, 1H), 5.37 (s, 2H), 4.12 (d, 2H), 3.72 (d, 2H), 2.36 (nonet, 1H), 2.08 (nonet, 1H), 1.03 (d, 6H), 0.98 (d, 6H) ppm. HPLC analysis (5:10:85 $H_2O$:A1:MeOH) showed a purity of 99% with a retention time of 8.0 min.

Compound #18

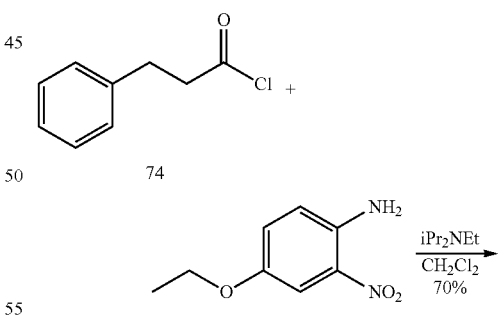

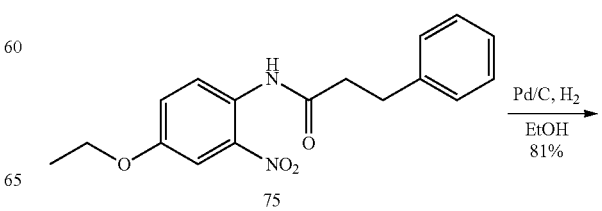

-continued

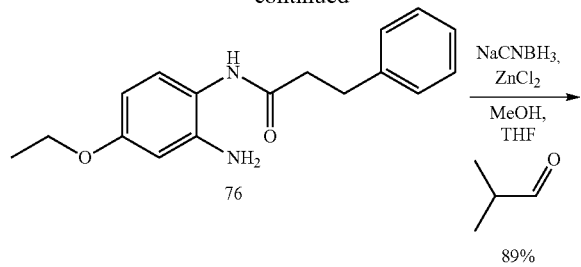

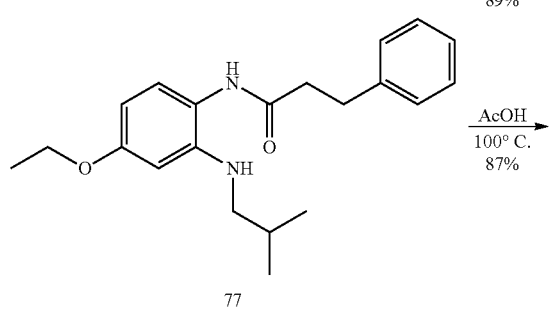

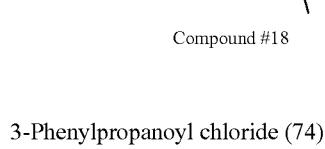

Compound #18

3-Phenylpropanoyl chloride (74)

A 200 mL flask fitted with a stir-bar and septum with an Ar inlet was charged with hydrocinnamic acid (5.00 g, 33.3 mmol), DMF (0.1 mL), and $CH_2Cl_2$ (30 mL). To the resultant solution was added $(COCl)_2$ (2M in $CH_2Cl_2$, 20.0 mL, 40.0 mmol) over 30 min. The mixture stirred overnight at rt, and then was concentrated in vacuo to give 5.9 g of 74 as a yellow oil (100%). HPLC analysis (15:10:75 $H_2O$:A1:MeOH) showed a purity of 99% with a retention time of 5.3 min.

N-(4-Ethoxy-2-nitrophenyl)-3-phenylpropanamide (75)

A 500 mL 3-neck flask fitted with a stir-bar, addition funnel, and an Ar inlet was charged with aniline 46a (4.00 g, 22.0 mmol) and $CH_2Cl_2$ (80 mL). To the resultant solution was added $iPr_2NEt$ (7.10 g, 55.0 mmol) followed by acid chloride 74 (4.27 g, 25.3 mmol) in $CH_2Cl_2$ (40 mL) over 15 min. The mixture stirred at rt overnight. Another 0.75 g of acid chloride 74 was added, and the mixture stirred 2 hr to completion as monitored by HPLC. The solution was diluted with $CH_2Cl_2$ (100 mL) and washed with saturated aqueous $NaHCO_3$ (125 mL) and brine (100 mL). The solution was filtered through phase separation paper and concentrated in vacuo to an oil/solid mix. The solid was collected with hexanes:EtOAc 4:1 (30 mL) and rinsed with hexanes:EtOAc 4:1 (2×10 mL). The material was dried to give 4.85 g of 75 as an orange solid (70%). $^1H$ NMR (60 MHz, $CDCl_3$): δ 9.8 (bs, 1H), 8.8 (d, 1H), 7.9 (d, 1H), 7.6 (s, 5H), 7.4 (d, 1H), 4.2 (qt, 2H), 3.1 (m, 4H), 1.5 (t, 3H) ppm. HPLC analysis (15:10:75 $H_2O$:A1:MeOH) showed a purity of 98% with a retention time of 6.9 min.

N-(2-Amino-4-ethoxyphenyl)-3-phenylpropanamide (76)

A 250 mL hydrogenation vessel was charged with amide 75 (4.80 g, 15.3 mmol) and EtOH (50 mL). To the resultant suspension was added 10% Pd/C (0.5 g), and the mixture was hydrogenated on a Parr shaker at 64 psi for 1.5 hr. The catalyst was filtered off on glass fiber paper and rinsed with MeOH (4×50 mL) to dissolve the precipitated product. The filtrate was then concentrated in vacuo to a yellow solid. The solid was collected with EtOH (15 mL) and rinsed with EtOH (2×3 mL) to give 3.3 g of a yellow solid. A second crop of 0.2 g was also collected to give a total of 3.5 g of 76 as a pale yellow solid (81%). $^1H$ NMR (Two isomers evident ~4:1) (300 MHz, $CDCl_3$): δ 7.39-7.18 (m, 4H), 6.90-6.82 (m, 2H), 6.35-6.22 (m, 2H), 3.95 (qt, 2H), 3.60 (bs, 2H), [3.06 (t, 1.6H), 2.84 (t, 0.4H)], [2.66 (t, 2H), 2.42 (t, 0.4H)], 1.38 (t, 3H) ppm. HPLC analysis (15:10:75 $H_2O$:A1:MeOH) showed a purity of greater than 99% with a retention time of 3.8 min.

N-[4-Ethoxy-2-(isobutylamino)phenyl]-3-phenylpropanamide (77)

A 250 mL 3-neck flask fitted with a stir-bar, addition funnel, and an Ar inlet was charged with aniline 76 (3.30 g, 11.6 mmol), THF (35 mL), and MeOH (10 mL). To the resultant solution was added isobutyraldehyde (1.17 g, 1.48 mL, 16.2 mmol), and the mixture stirred 15 min at rt. Meanwhile, in a 100 mL flask fitted with a stir-bar and septum with an Ar inlet, $NaCNBH_3$ (1M in THF, 16.2 mL, 16.2 mmol) was added to MeOH (10 mL). $ZnCl_2$ (1M in $Et_2O$, 8.1 mL, 8.1 mmol) was added next forming a cloudy mixture. After 15 min, this mixture was added to the above aniline solution. After stirring at rt 2.3 hr, another 0.3 mL isobutyraldehyde was added, followed by a second portion of 20% of the original amount of the $NaCNBH_3/ZnCl_2$ mixture as made previously. The mixture stirred overnight at rt. The cloudy solution was diluted with EtOAc (150 mL) and washed with saturated aqueous $NaHCO_3$ (2×125 mL) and brine (100 mL). The solution was filtered through phase separation paper and concentrated in vacuo to a yellow solid. The solid was triturated with hexanes: EtOAc 20:1 (20 mL), filtered, pressed with a rubber dam, and rinsed with hexanes (2×10 mL) to give 3.5 g of 77 as a yellow solid (89%). $^1H$ NMR (Two isomers evident ~3:2) (300 MHz, $CDCl_3$): δ 7.38-7.18 (m, 5H), [6.87 (d, 0.6H), 6.78 (d, 0.4H)], [6.62 (s, 0.6H), 6.48 (s, 0.4H)], 6.24-6.12 (m, 2H), [4.02 (qt, 1.2H), 4.00 (qt, 0.8H)], [3.07 (t, 1.2H), 2.92 (t, 0.8H)], [2.86 (d, 1.2H), 2.84 (d, 0.8H)], [2.71 (t, 1.2H), 2.40 (t, 0.8H)], [1.85 (nonet, 0.4H), 1.84 (nonet, 0.6H)], [1.41 (t, 1.2H), 1.38 (t, 1.8H)], 0.94 (d, 6H) ppm. HPLC analysis (5:10:85 $H_2O$: A1:MeOH) showed a purity of 98% with a retention time of 4.5 min.

2-[2-(3-Ethoxyphenyl)ethyl]-1-isobutyl-1H-benzimidazole (Compound #18)

A 50 mL flask fitted with a stir-bar and condenser was charged with amine 77 (1.50 g, 4.41 mmol) and AcOH (15 mL). The resultant solution was heated in a 100° C. bath for 1.5 hr to completion as monitored by HPLC. The solution was then concentrated in vacuo to an orange oil. The crude oil was taken up in EtOAc (75 mL) and washed with saturated aqueous $NaHCO_3$ (2×40 mL) and brine (30 mL). The solution was filtered through phase separation paper and concentrated in vacuo to an orange oil. The oil was filtered through a plug of silica gel with $CH_2Cl_2$ (4×100 mL). The fractions were concentrated to give 500 mg of an orange oil. The silica plug was flushed with EtOAc and concentrated to give another 840 mg. The combined material gave 1.34 g of Compound #18 as an orange oil (87%). $^1$H NMR (300 MHz, CDCl$_3$): δ 7.65 (d, 1H), 7.36-7.20 (m, 5H), 6.92 (dd, 1H), 6.77 (d, 1H), 4.11 (qt, 2H), 3.72 (d, 2H), 3.28 (m, 2H), 3.13 (m, 2H), 2.15 (nonet, 1H), 1.46 (t, 3H), 0.92 (d, 6H) ppm. HPLC analysis (5:10:85 H$_2$O:A1:MeOH) showed a purity of 99% with a retention time of 4.9 min.

Any compound of the invention whose synthesis is not explicitly exemplified herein can either be prepared by following the procedure of structurally similar compounds that have been exemplified herein or is available from commercial vendors or companies that sell compounds for screening. For example, the compound of formula

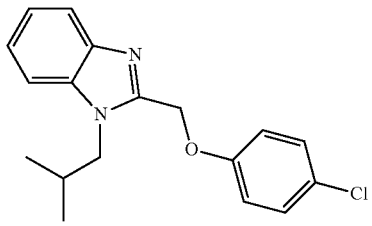 [SMILES: CC(C)Cn1c(COc2ccc(Cl)cc2)nc2ccccc21]

(RN: 433701-27-0) is available from Chemical Block Ltd., and from Enamine Historical HTS Collection. Similarly the compound of formula

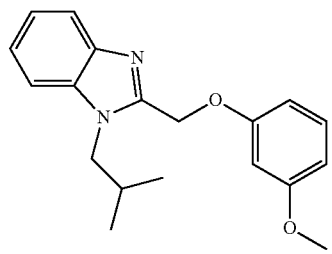 [SMILES: COc1cccc(OCc2nc3ccccc3n2CC(C)C)c1]

(RN: 891037-68-6) is available from Aurora Fine Chemicals. The compound of formula

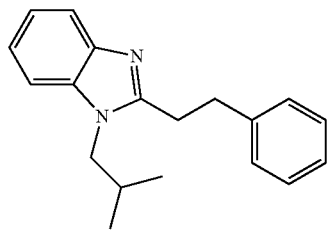 [SMILES: CC(C)Cn1c(CCc2ccccc2)nc2ccccc21]

(RN: 882351-68-0) is available from Akos Consulting. The compound of formula

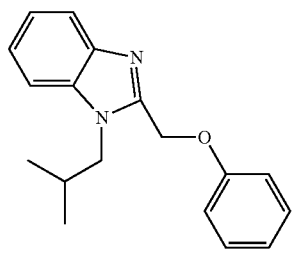 [SMILES: CC(C)Cn1c(COc2ccccc2)nc2ccccc21]

(RN: 378766-45-1) is available from Interbioscreen. Compound #3 (RN: 891037-75-5) whose synthesis has been shown above is also available from Aurora Fine Chemical.

Assays and Results:

To identify compounds that block persistent sodium currents, they were tested in a sodium depletion/repletion assay in which changes in the fluorescence of voltage-sensitive dyes measured in a Fluorometric Imaging Plate Reader (FLIPR) were used to infer the effects of the compounds on persistent sodium currents. The compounds were first tested in a single concentration HTS protocol. Those compounds that produced more than 80% inhibition of the control response were further tested in a 8-point concentration-response format, and the compound's antagonism of persistent current is expressed as its IC$_{50}$ (see Table 1 below).

TABLE 1

| Structure | FLIPR IC50 (μM) | IW IC50 (μM) | HTS % Block |
|---|---|---|---|
| Compound #3 | 0.081 | >30.00 | |

TABLE 1-continued

| Structure | FLIPR IC50 (μM) | IW IC50 (μM) | HTS % Block |
|---|---|---|---|
| benzimidazole-CH2-O-(3-OMe-phenyl), N-vinyl | 1.260 | >30 | 89.5 |
| benzimidazole-CH2-O-(3-OMe-phenyl), N-isobutyl | 1.340 | >30.00 | 88.4 |
| benzimidazole-CH2-O-(3-OMe-phenyl), N-isopentyl | 2.887 | >30.00 | 60.1 |
| benzimidazole-CH2-O-(3-OMe-phenyl), N-propyl | 8.029 | >30.00 | 80.5 |
| benzimidazole-CH(Et)-O-phenyl, N-ethyl | 8.456 | >30.00 | 88.9 |

To determine the selectivity of effects of these compounds on the persistent current, the inhibition of transient sodium currents using an automated patch clamp was also tested for the compounds. For direct measurement of Na+ currents the IonWorks automated patch clamp system was used. The Ion-Works system is a high-throughput electrophysiological instrument that performs whole-cell voltage clamp recordings in a 384-well plate format. Results are shown in Table 2.

TABLE 2
| Structure | $I_p$ (FLIPR IC50) (μM) | $I_t$ (IW IC50) (μM) |
|---|---|---|
| 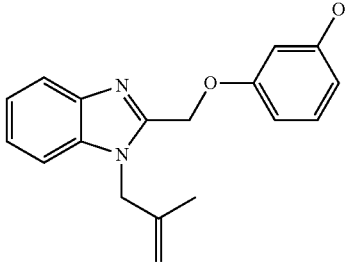<br>Compound #3 | 0.7-0.9 | >30 |
| 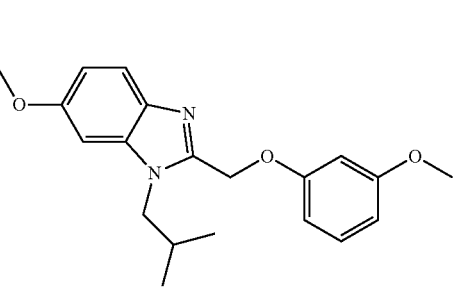<br>Compound #2 | 0.4 | >30 |
| 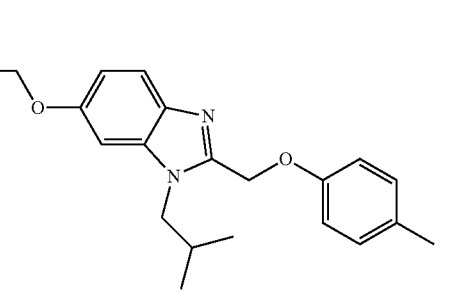 | 0.6 | >30 |
| 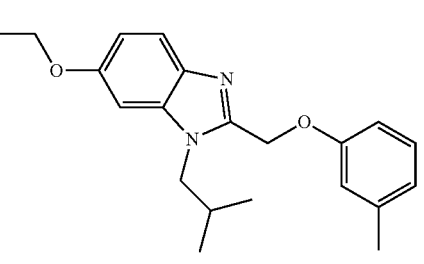 | 0.4 | >30 |
| 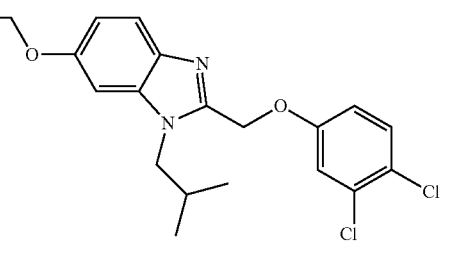 | 5.2 | >30 |

TABLE 2-continued

| Structure | I$_p$ (FLIPR IC50) (μM) | I$_t$ (IW IC50) (μM) |
|---|---|---|
| [benzimidazole structure with isobutoxy, isobutyl, and 4-(trifluoromethyl)phenoxymethyl substituents] | 6.9 | >30 |
| [benzimidazole structure with isobutoxy, isobutyl, and 3-(trifluoromethyl)phenoxymethyl substituents] | 0.1 | >30 |
| [benzimidazole structure with isobutoxy, isobutyl, and 2-naphthyloxymethyl substituents] | 2.5 | >30 |

Despite their utility in screening and identifying compounds, the FLIPR and IonWorks assays possess some disadvantages. The FLIPR assay cannot regulate cellular membrane potential and does not directly measure current conductance of VGSCs. In contrast, the IonWorks assay addresses these shortcomings, but does not produce the necessary gigohm seals to evaluate persistent current. Therefore, the efficacy and selectivity of the identified persistent current antagonists were verified using conventional gigohm-seal manual patch-clamp (MPC).

MPC experiments were conducted on human embroynic kidney (HEK) cells stably transfected with sodium channels were plated on coverslips. Cells were patch clamped using standard patch-clamp techniques (Hamill, O. P., A. Marty, et al., 1981 Pflugers Arch. 391:85-100). Once sufficient persistent current was established, buffer was introduced into the chamber at a constant flow rate of 0.5-1 minute/mL until the persistent current stabilized. Subsequent concentration-response experiments were conducted using this same flow rate. After application of the compound, current amplitude was monitored until equilibrium was established. The data recorded at equilibrium was normalized to the control current measured during perfusion with control buffer in the absence of a test compound. Adequate solution perfusion and gigohm seal stability were monitored throughout the experiment. The compound's antagonism of persistent or transient sodium currents is expressed as the IC50 of block for the respective current (see Table 1). Selectivity for block of the persistent current was calculated as the ratio of the IC50 for the transient current divided by the IC50 for the persistent current.

Direct measurement of the sodium current in cells expressing either Na$_v$1.3 or Na$_v$1.6 channels using gigohm seal MPC clearly demonstrated a strong selectivity of block. As shown for the exemplary compound (compound #3) in FIG. 1, low to submicromolar concentrations of these compounds were effective in blocking 50% of the persistent current while the effective dose for blocking the transient current greatly exceeded 30 μM.

Activity of the compounds on the rate of spontaneous firing of neurons was assessed in hippocampal neurons. Hippocampal cells from P-2 rats were cultured for 10-14 days prior to use. Cells were plated on laminin-coated cover slips that could be transferred to a perfusion chamber for conventional whole cell electrophysiological studies. Conventional whole cell current clamp methods were used to record steady state and spontaneous action potentials. Cells were held at their resting potential (Iclamp=0 pA) and spontaneous action potentials were recorded and followed over time. Healthy cells had low rates of spontaneous firing. Spontaneous firing rate increased with metabolic insults to cells, e.g. $Mg^{2+}$-depletion or with aging. Spontaneous firing appeared to occur more often in older cell cultures (10-14 days).

Compounds successful in the assay have been shown to be successful in preventing seizure activity in animal models of epilepsy and human disease. For example Compound #2 demonstrates an EC50 of 50.7 mg/kg when tested the 6 Hz seizure model in mice (Table 3 below) with a predicted TD50 of >500 mg/kg.

TABLE 3

Effect of Compound #2 in preventing seizures induced by a 6 Hz alternating current in mice. The compound was dosed one half-hour prior to application of a 6 Hz 32 milliamp current to the mice

| Test | Time (hr) | Dose (mg/kg) | Deaths | Protected/ Tested |
|---|---|---|---|---|
| 6 Hz | 0.50 | 12.5 | 0 | 1/8 |
| 6 Hz | 0.50 | 25.0 | 0 | 3/8 |
| 6 Hz | 0.50 | 50.0 | 0 | 3/8 |
| 6 Hz | 0.50 | 100.0 | 0 | 5/8 |
| 6 Hz | 0.50 | 200.0 | 0 | 8/8 |

Figure 2:
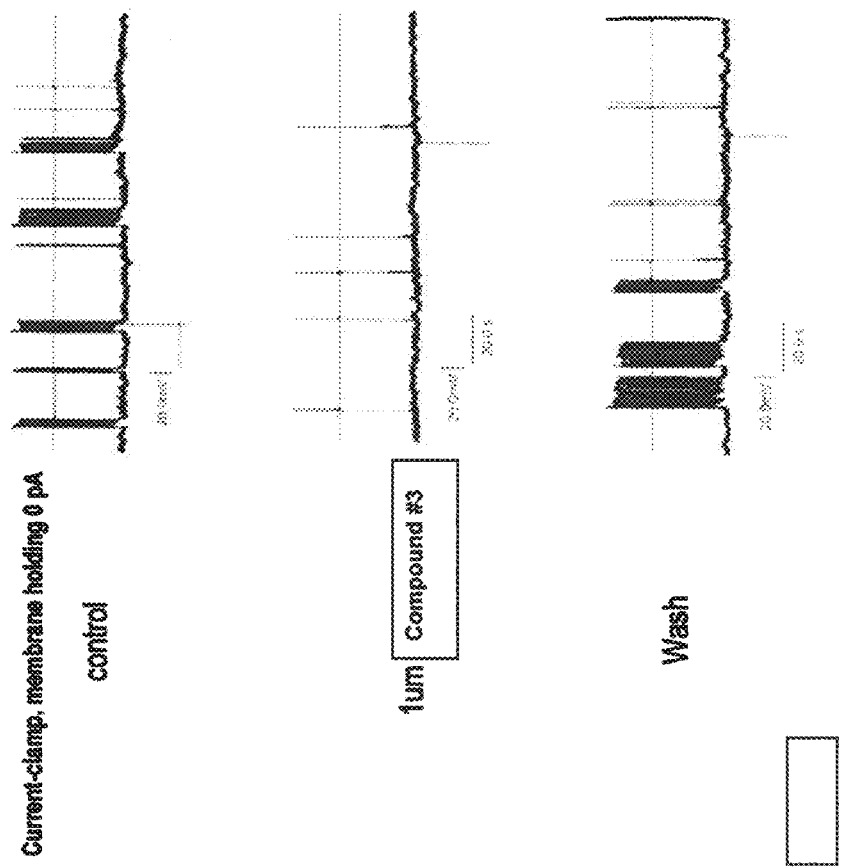
FIG. 2 shows the effects of compound #3 on the frequency of spontaneous discharge and bursting in rat cultured hippocampal pyramidal neurons. Hippocampal neurons were studied in the current-clamp configuration. The cell represented in this figure produced a profile of activity that included spontaneous bursts of action potentials (control). When 1 μM compound #3 was applied to the cell, bursting activity was reduced. The effects of compound #3 were reversible upon washing the chamber with control solution.

FIG. 2 shows the efficacy of selective persistent current blocker compound #3 in controlling neuronal hyperexcitability as studied in hippocampal neurons by examining the effects of the compound on action potential firing rates. The "current clamp" mode was employed to measure frequency of spontaneous discharge and action potential bursting in the absence and presence of compound #3 (1 µM). These data show that this compound potently decreased the spontaneous discharge of action potentials at a concentration that inhibits persistent currents, but does not affect transient currents. The results of these experiments contribute to the efficacy profile of the compounds of the present invention.

FIGS. 3-8 show methods for evaluating compounds for efficacy in treating outer retinal diseases, particularly age related macular degeneration (ARMD) and geographic atrophy (GA)

Figure 3:
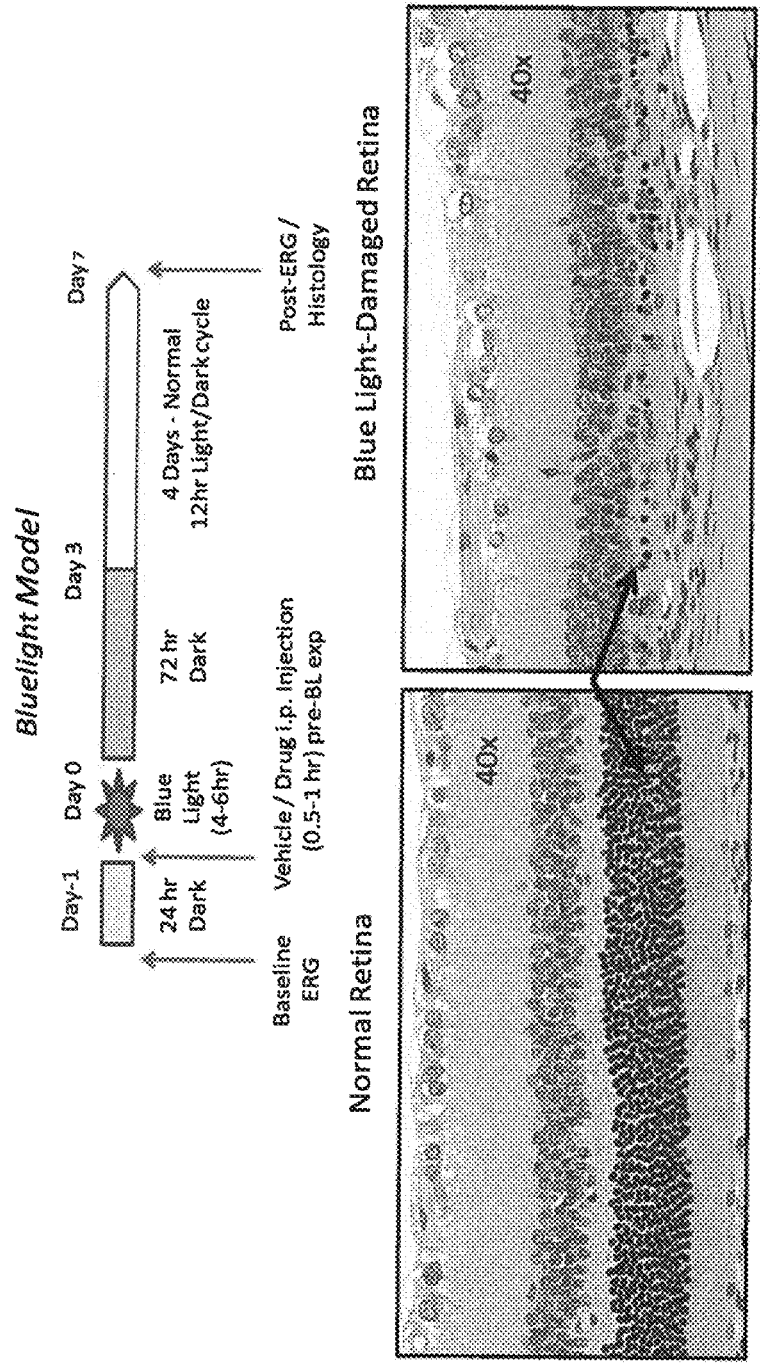
FIG. 3 shows blue light induced photoreceptor injury as a model for ARMD and GA. Exposure to blue light results in a loss of photoreceptor cells in the outer retina (arrows).

FIG. 3 shows blue light induced photoreceptor injury as a model for ARMD and GA. Exposure to blue light results in a loss of photoreceptor cells in the outer retina (arrows).

Figure 4:
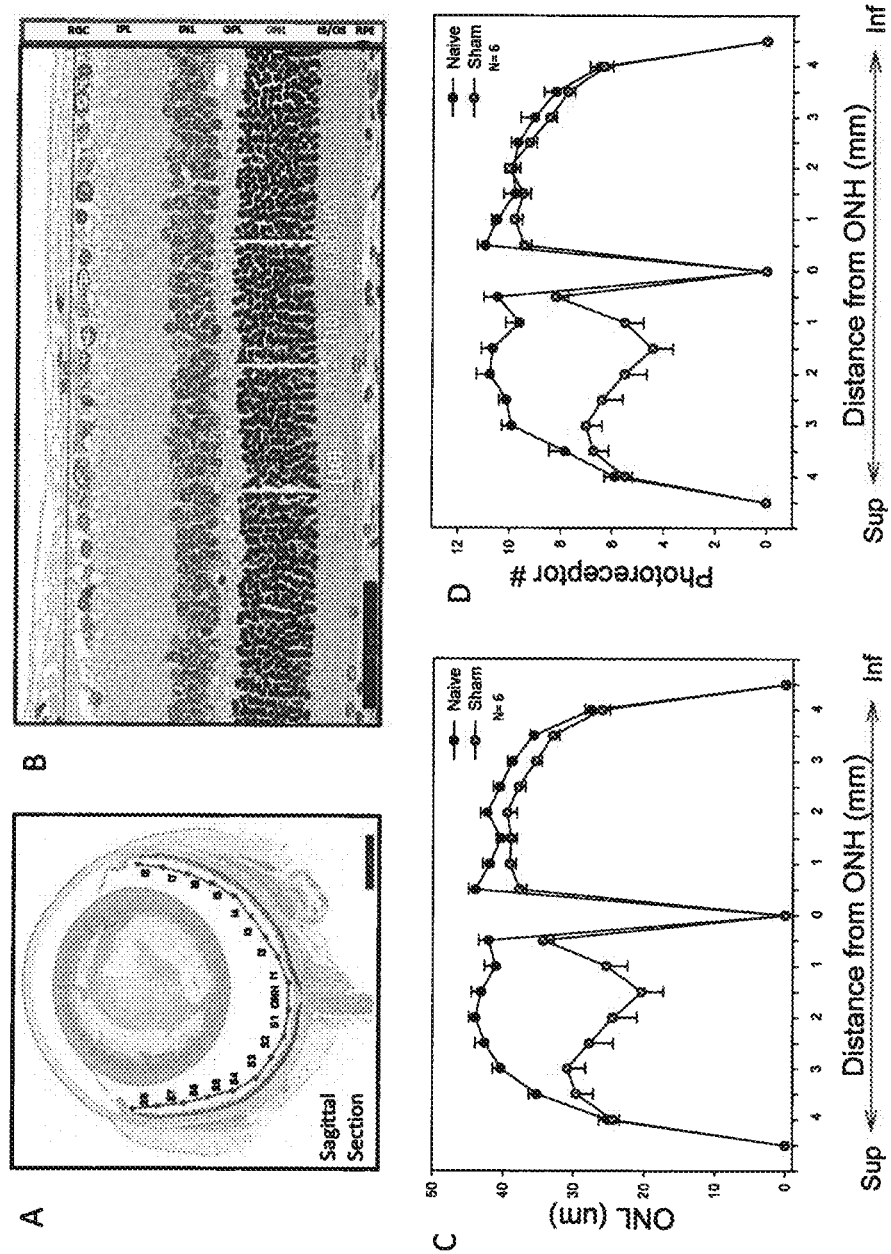
FIG. 4 shows methods for quantifying photoreceptor injury. Hemotoxylin and Eosin stained retinal sections are imaged and outer nuclear layer (ONL) thickness and cell count is evaluated in 8 consecutive regions on either side of the optic nerve head (ONH) (A). In Sprague Dawley rat the typical ONL thickness and photoreceptor cell counts adjacent to the ONH are approximately 40 microns and 10 cells, respectively (B). The cell counts and thicknesses from a retinal section taken from the vertical meridian reveal that in naïve retinae they are stable from just adjacent to ONH in to the ora serata (C,D). Following blue light exposure the cell number and layer thickness are reduced in the inferior retina (red symbols, C&D).

FIG. 4 shows methods for quantifying photoreceptor injury. Hemotoxylin and Eosin stained retinal sections are imaged and outer nuclear layer (ONL) thickness and cell count is evaluated in 8 consecutive regions on either side of the optic nerve head (ONH) (A). In Sprague Dawley rat the typical ONL thickness and photoreceptor cell counts adjacent to the ONH are approximately 40 microns and 10 cells, respectively (B). The cell counts and thicknesses from a retinal section taken from the vertical meridian reveal that in naïve retinae they are stable from just adjacent to ONH in to the ora serata (C,D). Following blue light exposure the cell number and layer thickness are reduced in the inferior retina (red symbols, C&D).

Figure 5:
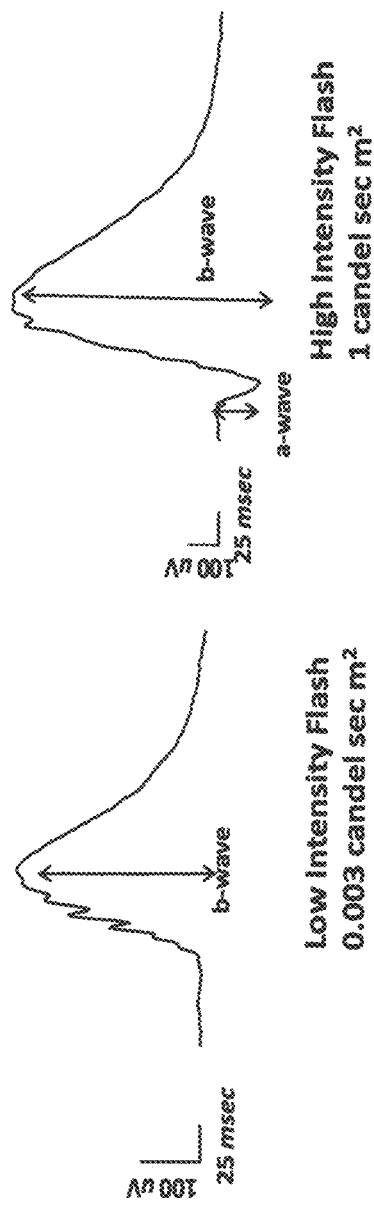
FIG. 5 shows that measurements of the electroretinogram (ERG) can be used to demonstrate retinal function in response to light stimulation.

FIG. 5 shows that measurements of the electroretinogram (ERG) can be used to demonstrate retinal function in response to light stimulation; i.e., ERG can be used to assess functional damage to retina induced by blue light.

Figure 6:
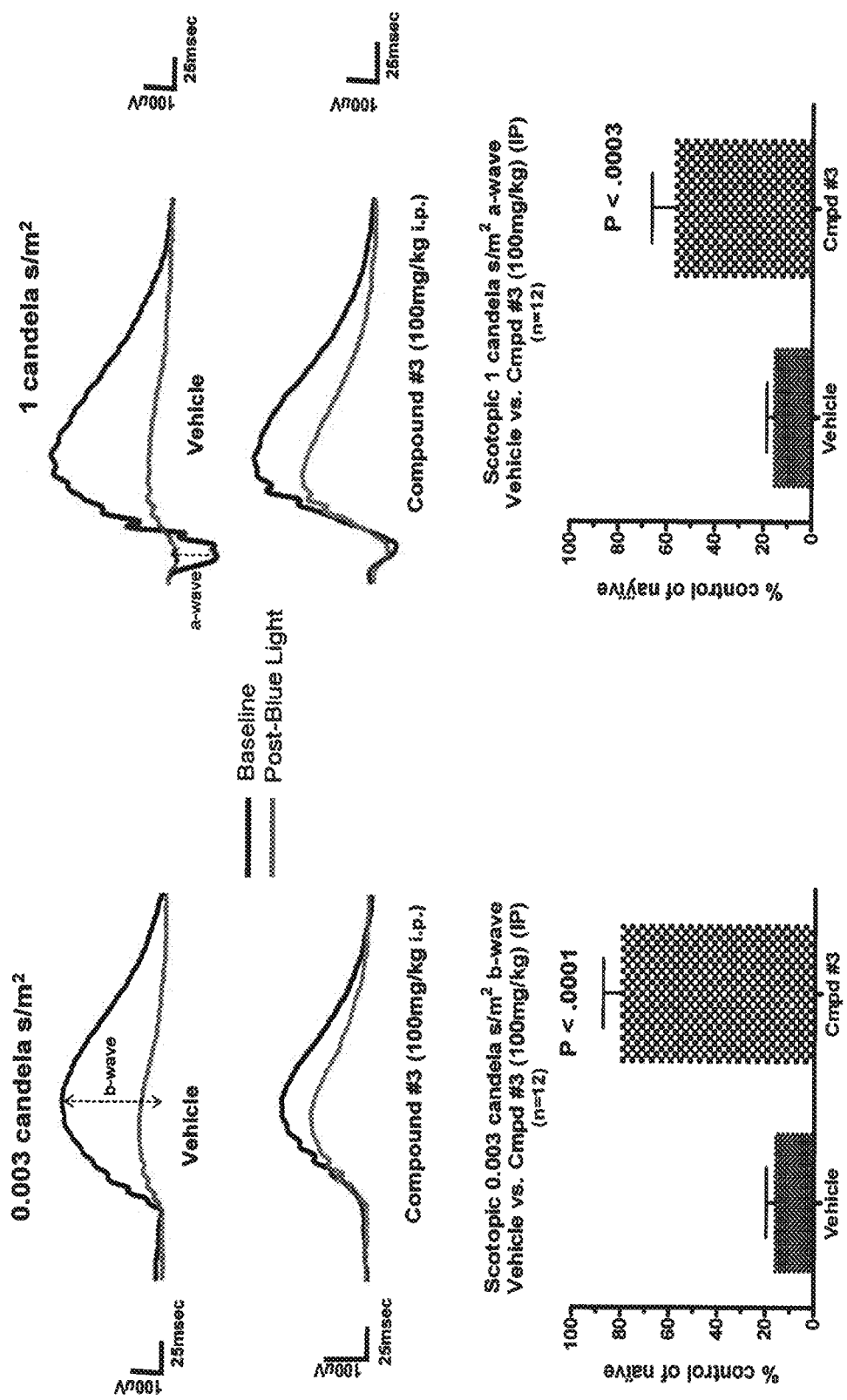
FIG. 6 shows that the compound #3 (100 mg/kg) i.p. preserves retinal function as determined by ERG. The top figures show representative ERG recorded traces of vehicle vs. compound #3 treated eyes, pre-(baseline) and post-blue light exposure. Notice both the B-wave and A-wave on conserved after compound #3 treatment vs. vehicle. The bottom graphs show the summary data for the scotopic 0.003 and 1 candela s/m² b-wave and a-wave amplitude measurements, respectively (n=12).

FIG. 6 shows that the compound #3 (100 mg/kg) i.p. preserves retinal function as determined by ERG. The top figures show representative ERG recorded traces of vehicle vs. compound #3 treated eyes, pre-(baseline) and post-blue light exposure. Notice both the B-wave and A-wave on conserved after compound #3 treatment vs. vehicle. The bottom graphs show the summary data for the scotopic 0.003 and 1 candela $s/m^2$ b-wave and a-wave amplitude measurements, respectively (n=12). In short, compound #3 significantly preserves retinal function after blue light exposure.

Figure 7:
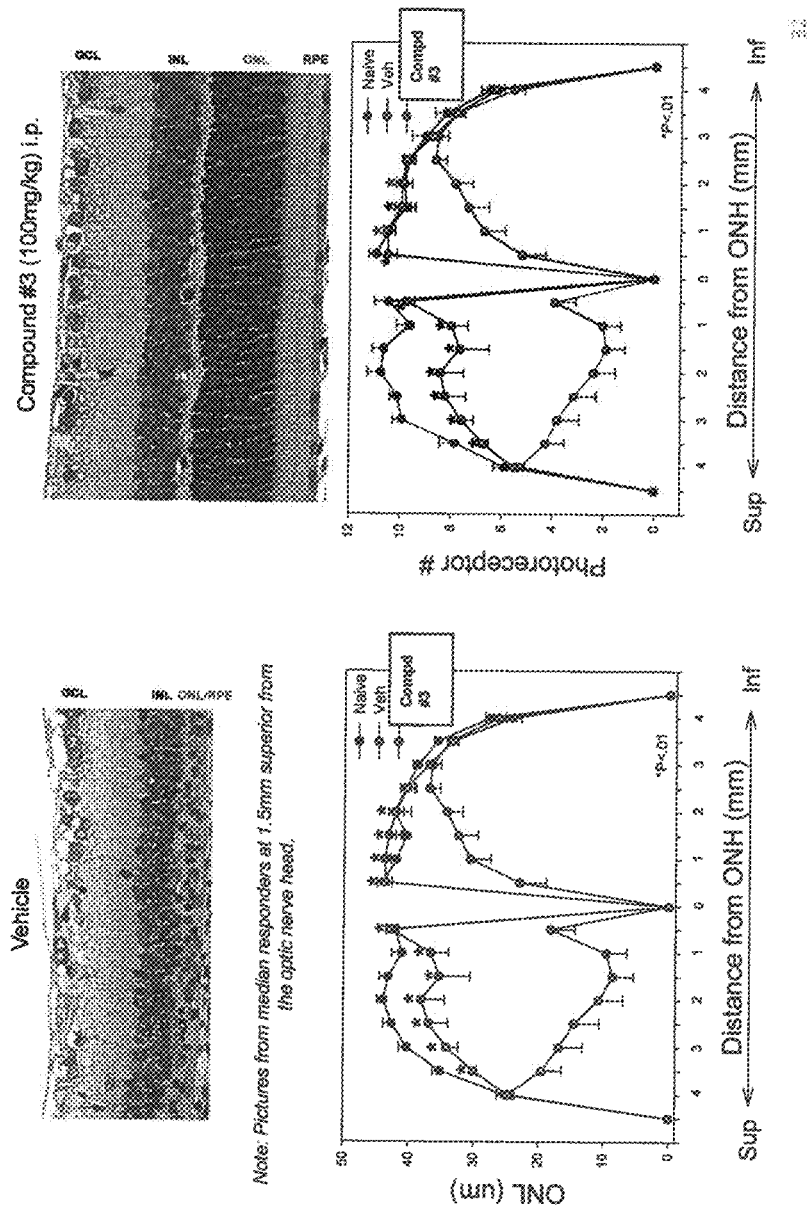
FIG. 7 shows that compound #3 protects photoreceptors from blue-light induced toxicity. The top figures show representative retinal images from vehicle and compound #3-treated median responders at 1.5 mm superior from the optic nerve head, the area of most damage after blue light exposure. The bottom graphs show a spider plot summary of the retinal outer nuclear layer (ONL) thickness and photoreceptor count for the number of eyes (n=12) used in the experiment. Image Legend Ganglion Cell Layer (GCL), Inner Nuclear Layer (INL), Outer Nuclear Layer (ONL), Retinal Pigment Epithelium (RPE).

FIG. 7 shows that consistent with the ERG functional data, compound #3 (100 mg/kg) i.p. preserved the structural integrity of the retina as determined by histology. The top figures show representative retinal images from vehicle and compound #3-treated median responders at 1.5 mm superior from the optic nerve head, the area of most damage after blue light exposure. The bottom graphs show a spider plot summary of the retinal outer nuclear layer (ONL) thickness and photoreceptor count for the number of eyes (n=12) used in the experiment (See details below on how spider plots were generated). Image Legend: Ganglion Cell Layer (GCL), Inner Nuclear Layer (INL), Outer Nuclear Layer (ONL), Retinal Pigment Epithelium (RPE).

Figure 8:
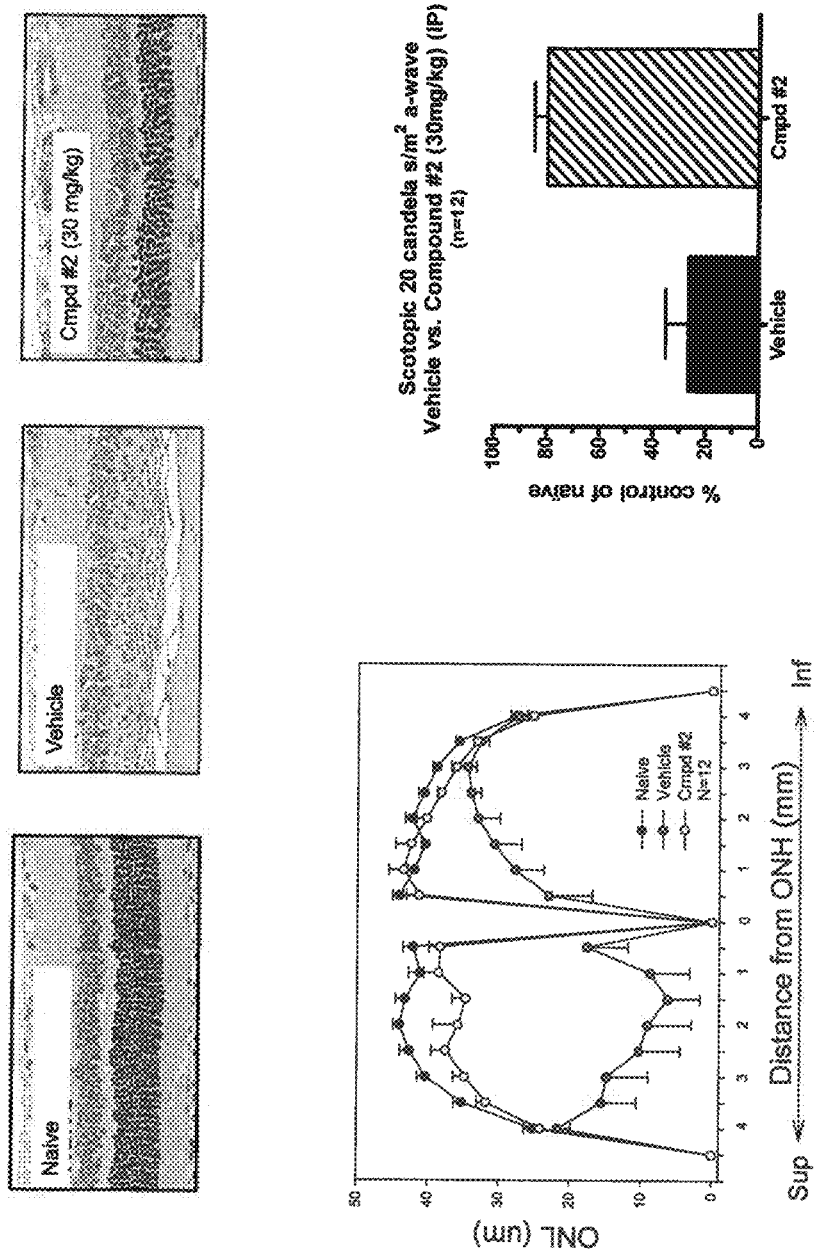
FIG. 8 shows that compound #2 (30 mg/kg) i.p. preserves retinal function and structure as determined by ERG and histology. The top figures show representative histological retinal images from naïve, vehicle and compound #2-treated median responders at 1.5 mm superior from the ONH, the area of most damage after blue light exposure. The bottom figures show a spider plot summary of the retinal outer nuclear layer (ONL) thickness and summary functional ERG data for the scotopic 20 candela s/m² a-wave amplitude measurements respectively (n=12). Taken together, the ERG and histology data suggests that compound #2 (30 mg/kg) i.p. significantly preserves retinal function after 6 hour blue light exposure.

FIG. 8 shows that compound #2 (30 mg/kg) i.p. preserves retinal function and structure as determined by ERG and histology. The top figures show representative histological retinal images from naïve, vehicle and compound #2-treated median responders at 1.5 mm superior from the ONH, the area of most damage after blue light exposure. The bottom figures show a spider plot summary of the retinal outer nuclear layer (ONL) thickness and summary functional ERG data for the scotopic 20 candela $s/m^2$ a-wave amplitude measurements respectively (n=12). Taken together, the ERG and histology data suggests that compound #2 (30 mg/kg) i.p. significantly preserves retinal function after 6 hour blue light exposure.

Details on Spider Plot Generation

Rat eyes were cut parallel to the vertical meridian through the optic nerve head and several sections were collected. Within each section, retina were divided into 500 mm regions, eight on either superior or inferior side of the optic nerve head. Within each 500 mm region, 3 measurements, 50 mm apart, were conducted, averaged and reported as ONL thickness (um). The number of rod and cone nuclei spanning the outer nuclear layer at each measurement site were counted manually and tabulated as photoreceptor #. For each animal, two to three sections were analyzed and averaged to give a final quantifiable value.

In Vivo Pain Assays: Reduction of Mechanical Allodynia and Thermal Hyperalgesia.

To assess the actions of the presently claimed benzimdazole compounds in neuropathic pain their efficacy in reversing the mechanical allodynia produced by spinal nerve ligation (Chung Model) and reducing the thermal hyperalgesia produced by subcutaneous injection of capsaicin was determined.

In the Chung spinal nerve ligation model, rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat temperature lamp.

Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Compounds to be tested were prepared as suspension in vehicle containing 2% sodium carboxymethylcellulose (CMC) and 1% Pluronic FI 27 by vigorous homogenization. On the day of the experiment, at least seven days after the surgery, six rats per test group were administered the test compounds/drugs or vehicle by intraperitoneal (i.p.) injection. Tactile allodynia was measured prior to and at increments of 15, 30, 60 and 90 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair.

Figure 9:
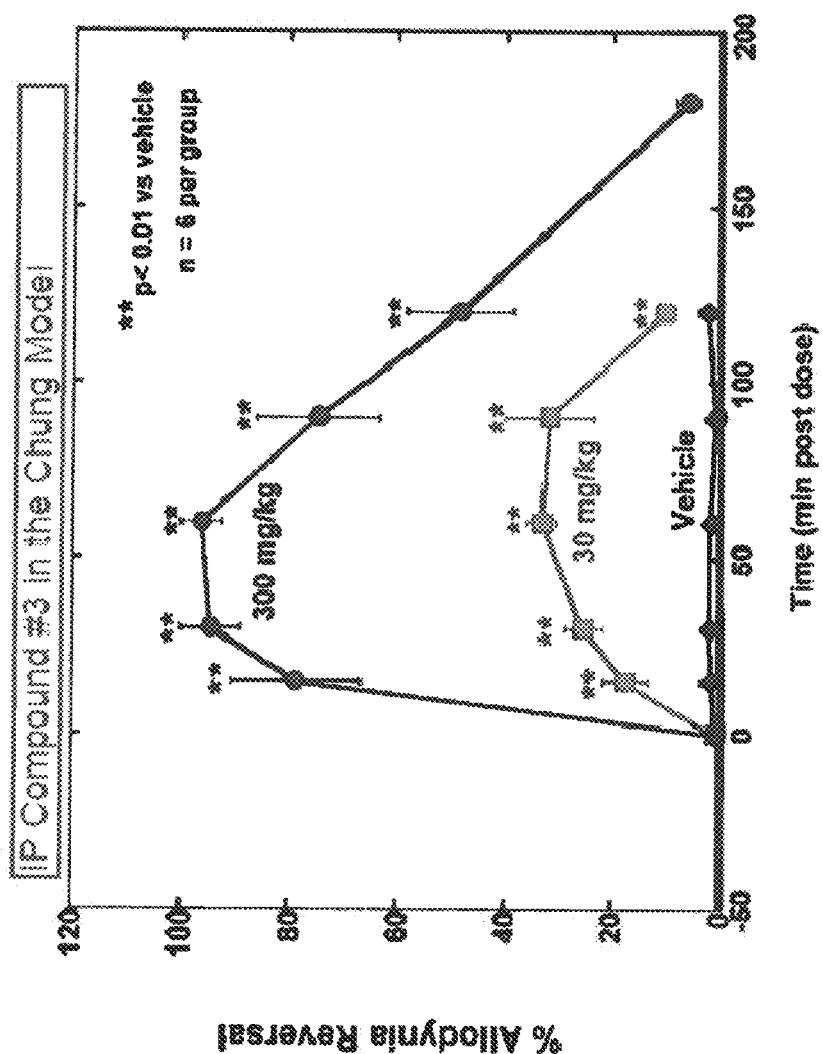
FIG. 9 shows the reversal of mechanical allodynia by of compound #3 following spinal nerve ligation. At doses of 30 and 300 mg/kg, compound #3 significantly reduced.

FIG. 9 shows that compound #3 displays reversal of mechanical allodynia following spinal nerve ligation. At doses of 300 mg/kg, compound #3 significantly reduced allodynia with respect to vehicle injected controls.

A second method for evaluating of 1,2 substituted benzimidazoles on neuropathic pain was to determine their effects on capsaicin-induced thermal hyperalgesia in the rat.

Peripherally administered capsaicin (the active agent in chili peppers) induces an acute, local, inflammatory response through actions on nociceptive sensory nerve endings ("pain fibers"). In rats, intraplantar injection of capsaicin produces decease in withdrawal latency to radiant heat (thermal hyperalgesia). This primary hyperalgesia, observed at the site of injury, is characterized by sensitization to thermal and mechanical stimulation. Primary hyperalgesia, especially that elicited by noxious thermal stimulus, is mediated, in part, by sensitization of C-fiber mechanoheat (polymodal) receptors (Kennis, 1982; Konietzny and Hensel, 1983; Simone, et al, 1987). This rat model has been used to identify small molecule therapeutics, including VR-1 and CB1 receptor antagonists. The purpose of this study was to determine the pharmacological efficacy of the present compounds in this model of thermal hyperalgesia.

Intraplantar injection of capsaicin (30 pg) was used to induce thermal hyperalgesia, as described previously (Gilchrist et al., 1996). The plantar test was used to assess capsaicin-induced thermal hyperalgesia (n=6/group). For this test, hind paw withdrawal latencies (PWLs) to a noxious thermal stimulus were determined using the technique described by Hargreaves et al. (1988) using a plantar test apparatus (PAW Thermal Analgesia Meter instrument Department of Anesthesiology, UCSD, San Diego, Calif.). Time to remove paw from heat source is measured and expressed as the paw withdrawal latency. Cut-off was set at 20.48 seconds, and any directed paw withdrawal from the heat source was taken as the endpoint. The glass plate temperature was set at 25° C. and the light intensity at 4.8 Amperes.

Compounds to be tested were prepared as suspension in vehicle containing 2% sodium carboxymethylcellulose (CMC) and 1% Pluronic FI 27 by vigorous homogenization. On the day of the experiment, six rats per test group were administered the test drugs or vehicle by intraperitoneal (i.p.) injection 30 minutes prior to intraplantar injection of capsaicin. Post-capsaicin paw withdrawal latency were assessed 30 minutes after capsaicin challenge. Pre-capsaicin and post-capsaicin values were compared using a repeated measures one-way ANOVA and pairwise Multiple Comparison Procedures (Dunns method).

Figure 10:
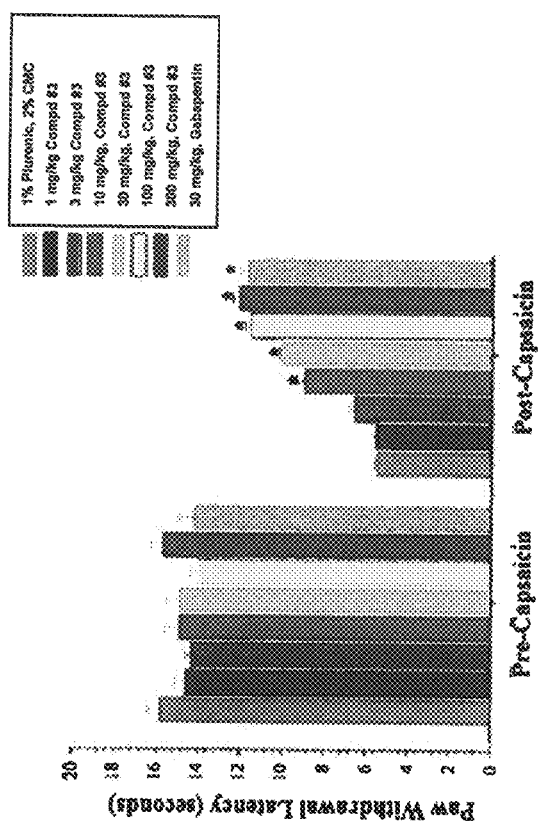
FIG. 10 shows that compound #3 at doses 10 mg/kg and above significantly reduces capsaicin-induced thermal hyperalgesia.

FIG. 10 shows that the exemplary compound, compound #3 at doses 10 mg/kg and above significantly reduces capsaicin-induced thermal hyperalgesia in this model. The effects of compound #3 were similar to those of gabapentin, which is indicated for the treatment of pain resulting from postherpetic neuralgia.

Figure 11:
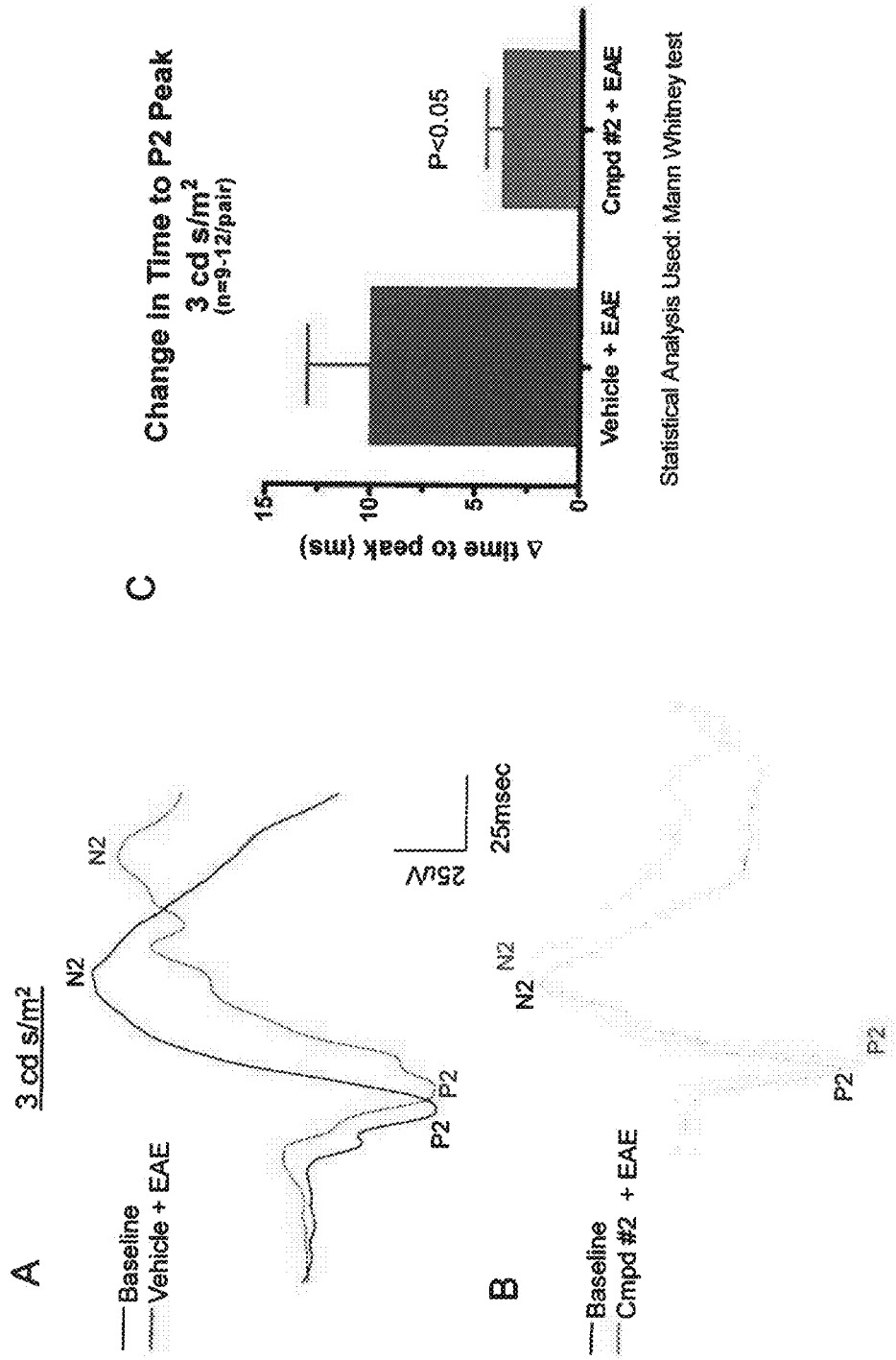
FIG. 11 shows that Compound #2 at a dose of 30 mg/kg significantly reduces the initial clinical sign of paralysis in rats with Experimental Autoimmune Encephalomyelitis (EAE). (A) Representative flash Visual Evoked Potential (VEP) traces from baseline and following the induction of EAE. Three distinct peaks, N1, P2, N2 are labeled in the traces, with P2 being the most reproducible. Note that following the induction of EAE the latency to the P2 peak is increased. This is associated with a poor visual outcome in Optic Neuritis in humans. (B) Dosing with 50 mg/kg preserves VEP latency in EAE. (C) This graph shows summarizes the protection of the P2 peak by Cmpd #2 at 50 mg/kg. The maximum clinical score is the score associated with the most severe paralysis each animal experienced during the daily observation period. The graph indicates that animals treated with Compound #2 displayed a significantly (P<0.01) average lower clinical score than those treated with vehicle, suggesting this compound may have utility in reducing paralysis resulting from multiple sclerosis.

FIG. 11 shows that Compound #2 at a dose of 30 mg/kg significantly reduces the initial clinical sign of paralysis in rats with Experimental Autoimmune Encephalomyelitis (EAE). (A) Representative flash Visual Evoked Potential (VEP) traces from baseline and following the induction of EAE. Three distinct peaks, N1, P2, N2 are labeled in the traces, with P2 being the most reproducible. Note that following the induction of EAE the latency to the P2 peak is increased. This is associated with a poor visual outcome in Optic Neuritis in humans. (B) Dosing with 50 mg/kg preserves VEP latency in EAE. (C) This graph shows summarizes the protection of the P2 peak by Cmpd #2 at 50 mg/kg. The maximum clinical score is the score associated with the most severe paralysis each animal experienced during the daily observation period. The graph indicates that animals treated with Compound #2 displayed a significantly ($P<0.01$) average lower clinical score than those treated with vehicle, suggesting this compound may have utility in reducing paralysis resulting from multiple sclerosis.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered orally, subcutaneously, intravenously, intrathecally or some suitable combination(s) thereof.

In addition to the common dosage forms set out above, the compounds of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are incorporated herein by reference.

For use where a composition for intravenous administration is employed, a suitable daily dosage range for antiinflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

Preferably, the pharmaceutical preparation is in a unit dosage form. In such form, the preparation is subdivided into suitably sized unit doses containing appropriate quantities of the active component, e.g., an effective amount to achieve the desired purpose.

The magnitude of prophylactic or therapeutic dose of a compound of this invention will, of course, vary with the nature of the severity of the condition to be treated and with the particular compound and its route of administration. It will also vary according to the age, weight and response of the individual patient. It is understood that a specific daily dosage amount can simultaneously be both a therapeutically effective amount, e.g., for treatment to slow progression of an existing condition, and a prophylactically effective amount, e.g., for prevention of condition.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the compounds of the present invention. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

In one aspect, the present invention provides a kit comprising a therapeutically effective amount of at least one compound of the present invention, or a pharmaceutically acceptable salt of said compound and a pharmaceutically acceptable carrier, vehicle or diluents, and directions for the use of said kit.

Each and every reference disclosed in the specification, whether non-patent (e.g., scientific, journal references) or patent (e.g., granted patents or published patent applications) is incorporated herein by reference in its entirety for all purposes.

The foregoing descriptions details specific methods and compositions that can be employed to practice the present invention, and represents the best mode comtemplated. It should not be construed as limiting the overall scope hereof; rather, the ambit of the present invention is to be governed only by the lawful construction of the appended claims.

What is claimed is:

1. A compound selected from the group consisting of:

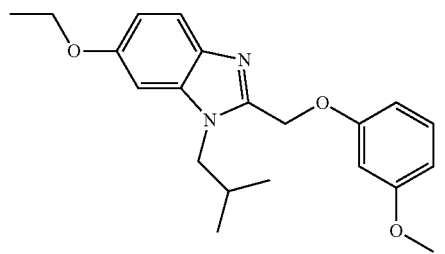

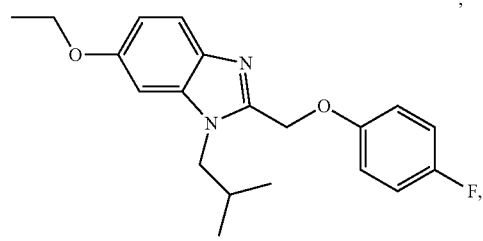

75
-continued
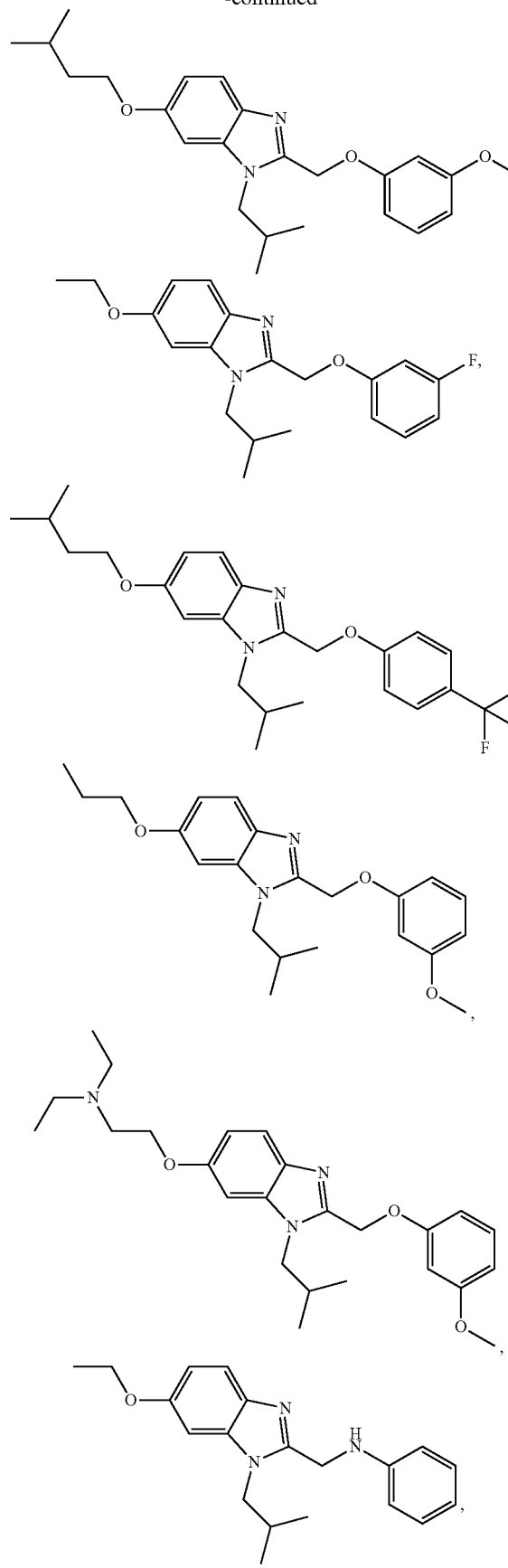
76
-continued
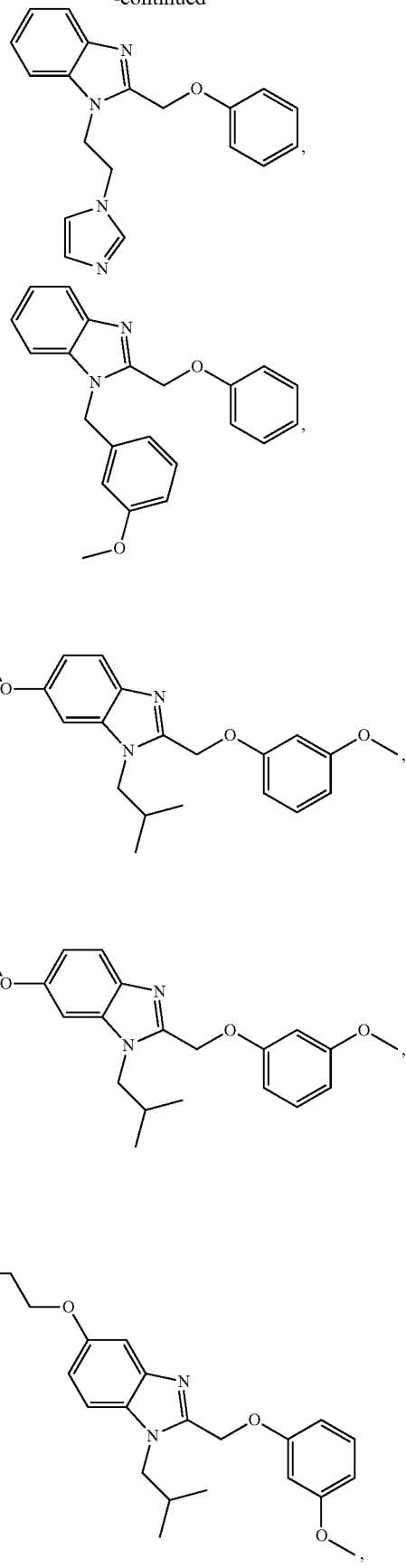

77
-continued
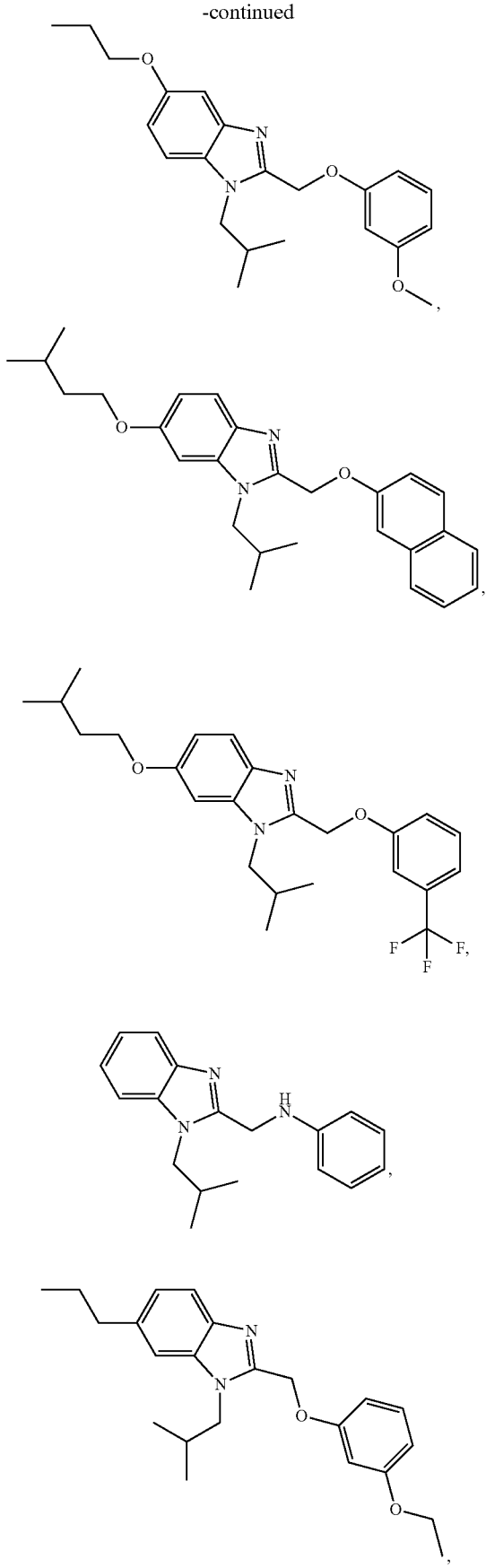
78
-continued
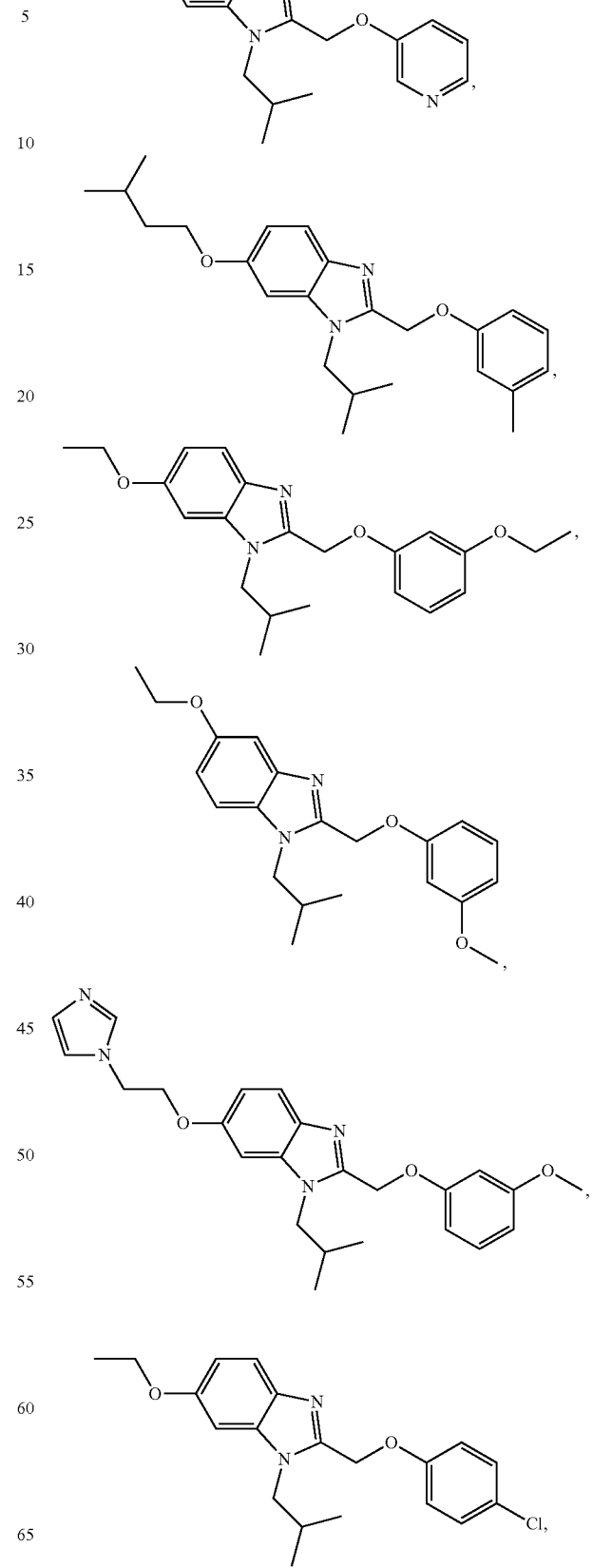

-continued

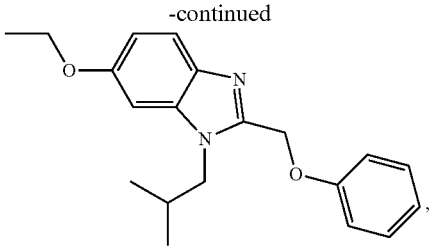

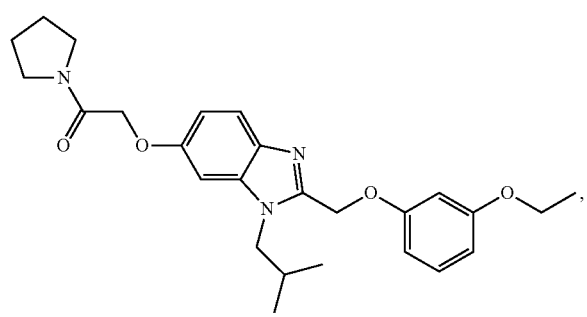

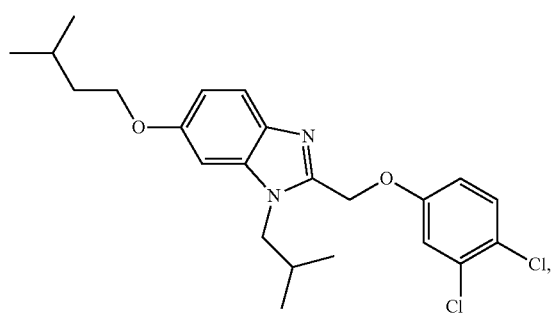

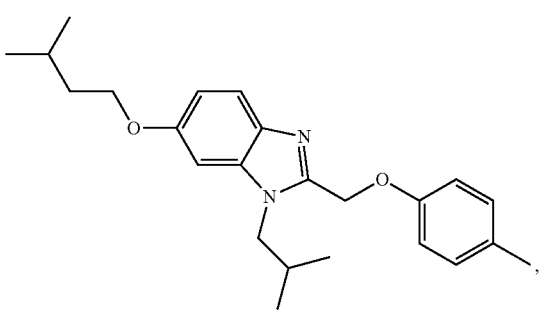

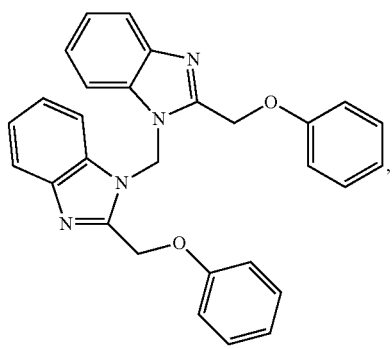

-continued

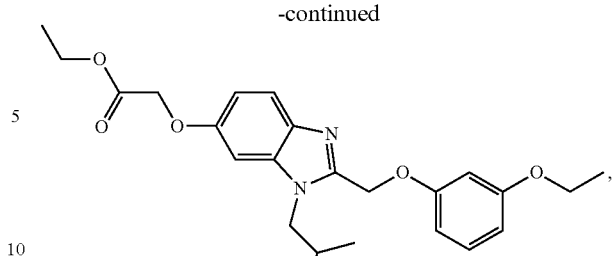

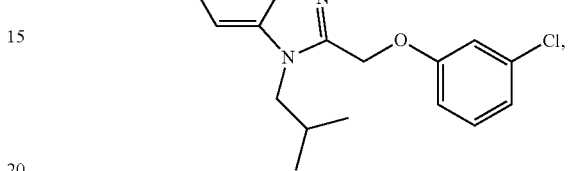

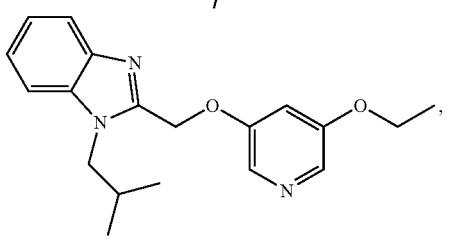

and

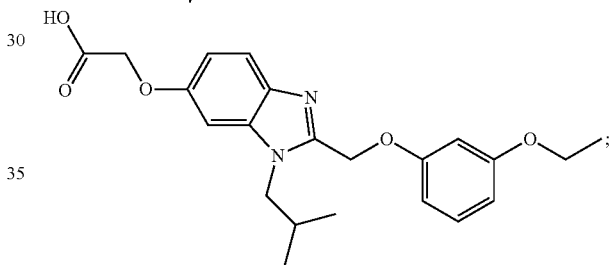

or a pharmaceutically acceptable salt thereof.

2. A pharmaceutical composition comprising at least one compound of claim 1, or a pharmaceutically acceptable salt thereof, and at least one pharmaceutically acceptable carrier.

3. A method of blocking persistent sodium current without affecting transient current in a mammal comprising administering to said mammal in need thereof a therapeutically effective amount of at least one compound of claim 1 or a pharmaceutically acceptable salt thereof.

4. A method of treating a disease or condition in a mammal, wherein said disease or condition is selected from the group consisting of chronic pain, ocular disorder, multiple sclerosis, and seizure disorder, comprising administering to said mammal in need thereof an effective amount of at least one compound of claim 1 or a pharmaceutically acceptable salt thereof.

5. The method of claim 4, wherein the ocular disorder is selected from the group consisting of age related macular degeneration, geographic atrophy (GA), retinitis pigmentosa, Stargardt's disease cone dystrophy, and pattern dystrophy of the retinal pigmented epithelium, macular edema, retinal detachment, retinal trauma, retinal tumors congenital hypertrophy of the retinal pigmented epithelium, acute posterior multifocal placoid pigment epitheliopathy, optic neuritis, acute retinal pigment epithelitis, optic neuropathies and glaucoma; the chronic pain is selected from the group consisting of neuropathic pain, inflammatory pain, visceral pain, postoperative pain, pain resulting from cancer or cancer treatment, headache pain, irritable bowel syndrome pain, fibromyalgia pain, and pain resulting from diabetic neuropathy; and the seizure disorder is selected from the group consisting of epilepsy and chemically-induced seizure disorder.

6. A compound of the formula:

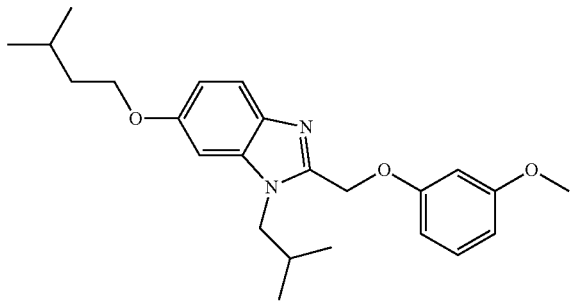 [SMILES: COc1cccc(OCc2nc3ccc(OCCC(C)C)cc3n2CC(C)C)c1]

or a pharmaceutically acceptable salt thereof.

7. A pharmaceutical composition comprising the compound of claim 6, or a pharmaceutically acceptable salt thereof, and at least one pharmaceutically acceptable carrier.

8. A method of blocking persistent sodium current without affecting transient current in a mammal comprising administering to said mammal in need thereof a therapeutically effective amount of the compound of claim 6, or a pharmaceutically acceptable salt thereof.

9. A method of treating a disease or condition in a mammal, wherein said disease or condition is selected from the group consisting of chronic pain, ocular disorder, multiple sclerosis, and seizure disorder, comprising administering to said mammal in need thereof an effective amount of the compound of claim 6, or a pharmaceutically acceptable salt thereof.

10. The method of claim 9, wherein the ocular disorder is selected from the group consisting of age related macular degeneration, geographic atrophy (GA), retinitis pigmentosa, Stargardt's disease cone dystrophy, and pattern dystrophy of the retinal pigmented epithelium, macular edema, retinal detachment, retinal trauma, retinal tumors congenital hypertrophy of the retinal pigmented epithelium, acute posterior multifocal placoid pigment epitheliopathy, optic neuritis, acute retinal pigment epithelitis, optic neuropathies and glaucoma; the chronic pain is selected from the group consisting of neuropathic pain, inflammatory pain, visceral pain, postoperative pain, pain resulting from cancer or cancer treatment, headache pain, irritable bowel syndrome pain, fibromyalgia pain, and pain resulting from diabetic neuropathy; and the seizure disorder is selected from the group consisting of epilepsy and chemically-induced seizure disorder.

* * * * *